US007601332B2

(12) United States Patent
Vlahov et al.

(10) Patent No.: US 7,601,332 B2
(45) Date of Patent: Oct. 13, 2009

(54) VITAMIN RECEPTOR BINDING DRUG DELIVERY CONJUGATES

(75) Inventors: Iontcho R. Vlahov, Lafayette, IN (US); Christopher P. Leamon, West Lafayette, IN (US); Matthew A. Parker, San Diego, CA (US); Stephen J. Howard, West Lafayette, IN (US); Hari Krishna Santhapuram, West Lafayette, IN (US); Apparao Satyam, Mumbai (IN); Joseph Anand Reddy, West Lafayette, IN (US)

(73) Assignee: Endocyte, Inc., West Lafayette, IN (US)

( * ) Notice: Subject to any disclaimer, the term of this patent is extended or adjusted under 35 U.S.C. 154(b) by 478 days.

(21) Appl. No.: 10/765,336

(22) Filed: Jan. 27, 2004

(65) Prior Publication Data

US 2005/0002942 A1 Jan. 6, 2005

Related U.S. Application Data

(60) Provisional application No. 60/442,845, filed on Jan. 27, 2003, provisional application No. 60/492,119, filed on Aug. 1, 2003, provisional application No. 60/516,188, filed on Oct. 31, 2003.

(51) Int. Cl.
*A61K 51/00* (2006.01)
*A61M 36/14* (2006.01)

(52) U.S. Cl. ............... 424/1.73; 424/1.11; 424/1.65; 424/9.1

(58) Field of Classification Search ............ 424/1.11, 424/1.37, 1.65, 1.49, 1.69, 1.73, 1.81, 9.1, 424/1.33, 9.2, 9.3, 9.4, 9.5, 9.6, 9.7, 9.8; 534/7, 10–16; 568/824; 544/251, 327; 546/301; 549/315; 552/653, 299; 548/400
See application file for complete search history.

(56) References Cited

U.S. PATENT DOCUMENTS

| | | | |
|---|---|---|---|
| 2,816,110 A | 12/1957 | Sletzinger et al. | |
| 4,691,024 A | 9/1987 | Sirahata | |
| 4,713,249 A | 12/1987 | Schroder | |
| 5,140,104 A | 8/1992 | Coughlin et al. | |
| 5,266,333 A | 11/1993 | Cady | |
| 5,417,982 A | 5/1995 | Modi | |
| 5,552,545 A | 9/1996 | Pearce et al. | |
| 5,672,486 A | 9/1997 | Soulillou | |
| 5,998,603 A | 12/1999 | Cook | |
| 6,030,941 A * | 2/2000 | Summerton et al. | 514/2 |
| 6,056,973 A | 5/2000 | Allen | |
| 6,077,499 A | 6/2000 | Griffiths | |
| 6,335,434 B1 | 1/2002 | Guzaev et al. | |
| 6,596,757 B1 * | 7/2003 | Chari et al. | 514/449 |
| 7,067,111 B1 * | 6/2006 | Yang et al. | 424/9.1 |
| 7,128,893 B2 * | 10/2006 | Leamon et al. | 424/9.1 |

FOREIGN PATENT DOCUMENTS

| | | |
|---|---|---|
| WO | WO 99/61055 * | 12/1999 |
| WO | WO 00/35422 | 6/2000 |
| WO | PCT/US2008/054189 | 2/2008 |
| WO | PCT/US2008/056824 | 3/2008 |
| WO | PCT/US2008068093 | 6/2008 |

OTHER PUBLICATIONS

Lu et al, Cancer Immunology Immunotherapy, Mar. 2002, vol. 51, No. 3, pp. 153-162.*
Punj, Vasu; Graves, Jewell M.; Mehta, Rajeshwari R.; "Effect of Vitamin D Analog (1α Hydroxy D5) Immunoconjugated to Her-2 Antibody on Breast Cancer," Int. J. Cancer, 108, 922-929, 2004.
Anderson et al., "Potocytosis: Sequestration and transport of small molecules by caveolae," Science 255: 410-411 (1992).
Antony, A. C., "Folate receptors," Annu Rev Nutr, 16: 501-21 (1996).
Antony, A. C., "The biological chemistry of folate receptors," Blood 79(11):2807-2820 (1992).
Barnett et al., "Structure-Activity Relationships of Dimeric Catharanthus Alkaloids. 1. Deacetylvinblastine Amide (Vindesine) Sulfate," J. Med. Chem. 21: 88-96 (1978).
Boger, D.L., et al., "1,2,9,9a-Tetrahydrocyclopropa[ c ]benz[ e]indol-4-one (CBI): A Simplified Analogue of the CC-1065 Alkylation Subunit," J. Org. Chem. 57: 2873-2876 (1992).
Campbell et al., "Folate-binding protein is a marker for ovarian cancer," Cancer Res. 51: 5329-5338 (1991).
Cho et al., "Single-chain Fv/folate conjugates mediate efficient lysis of folate-receptor-positive tumor cells," Bioconjug. Chem. 8(3): 338-346 (1997).
Christensen et al., "Membrane receptors for endocytosis in the renal proximal tubule," Int. Rev. Cytol. 180: 237-284 (1998).
Citro, et al., "Inhibition of leukemia cell proliferation by folic acid—polylysine-mediated introduction of c-*myb* antisense oligodeoxynucelotides into HL-60 cells," Br. J. Cancerl, 69, 463-467, (1994).
Frankel, A.E., "Immunotoxin therapy of cancer," Oncology 7: 69 (1993).

(Continued)

Primary Examiner—D. L Jones
(74) Attorney, Agent, or Firm—Barnes & Thornburg LLP

(57) ABSTRACT

The invention describes a vitamin receptor binding drug delivery conjugate, and preparations therefor. The drug delivery conjugate consists of a vitamin receptor binding moiety, a bivalent linker (L), and a drug. The vitamin receptor binding moiety includes vitamins, and vitamin receptor binding analogs and derivatives thereof, and the drug includes analogs and derivatives thereof. The vitamin receptor binding moiety is covalently linked to the bivalent linker, and the drug, or the analog or the derivative thereof, is covalently linked to the bivalent linker, wherein the bivalent linker (L) includes components such as spacer linkers, releasable linkers, and heteroatom linkers, and combinations thereof. Methods and pharmaceutical compositions for eliminating pathogenic cell populations using the drug delivery conjugate are also described.

73 Claims, 8 Drawing Sheets

Garin-Chesa et al., "Trophoblast and ovarian cancer antigen LK26. Sensitivity and specificity in immunopathology and molecular identification as a folate-binding protein," *Am. J. Pathol.* 142(2): 557-562 (1993).

Gottschalk, S., et al., "Folate receptor mediated DNA delivery into tumor cells: potosomal disruption results in enhanced gene expression," *Gene Therapy* 1(3): 185-191 (1994).

Hofland et al., "Folate-targeted gene transfer in vivo," *Mol Ther* 5(6): 739-744 (2002).

Holladay et al., "Riboflavin-mediated delivery of a macromolecule into cultured human cells," *Biochim Biophys Acta* 1426(1): 195-204 (1999).

Holm, J., et al., "Folate receptors in malignant and benign tissues of human female genital tract," *BioSci. Rep.* 17(4): 415-427 (1997).

Holm, J., et al., "High-affinity folate binding in human choroid plexus. Characterization of radioligand binding, immunoreactivity, molecular heterogeneity and hydrophobic domain of the binding protein," *Biochem J.* 280(1): 267-271 (1991).

Kamen et al., "Delivery of folates to the cytoplasm fo MA104 cells is mediated by a surface receptor that recycles," *J. Biol. Chem.* 263: 13602-13609 (1988).

Kamen, B. A. and Capdevila, A., "Receptor-mediated folate accumulation is regulated by the cellular folate content," *Proc. Natl. Acad. Sci. USA* 83: 5983-5987 (1986).

Kamen et al., "The folate receptor works in tandem with a probenecid-sensitive carrier in MA104 cells in vitro," *J. Clin. Invest.* 87(4): 1442-1449 (1991).

Kane et al., "The influence of extracellular folate concentration on methotrexate uptake by human KB cells. Partial characterization of a membrane-associated methotrexate binding protein," *J. Biol. Chem.* 261: 44-49 (1986).

Kranz et al., "Conjugates of folate and anti-T-cell-receptor antibodies specifically target folate-receptor-positive tumor cells for lysis," *Proc. Natl. Acad. Sci. USA* 92(20), 9057-9061 1995.

Ladino et al., "Folate-maytansinoids: target-selective drugs of low molecular weight," *Int. J. Cancer* 73(6): 859 864 (1997).

Leamon, C. P. and Low, P. S., "Folate-mediated targeting: from diagnostics to drug and gene delivery," *Drug Discovery Today* 6: 36-43 (2001).

Leamon, C. P. and Low, P. S, "Cytotoxicity of momordin-folate conjugates in cultured human cells," *J. Biol. Chem.* 267(35): 24966-24971 (1992).

Leamon, C. P. and Low, P. S, "Delivery of macromolecules into living cells: a method that exploits folate receptor endocytosis," *Proc. Natl. Acad. Sci. USA* 88(13): 5572-5573 (1991).

Leamon, C. P. and Low, P. S, "Membrane folate-binding proteins are responsible for folate-protein conjugate endocytosis into cultured cells," *Biochem. J.* 291: 855-860 (1993).

Leamon, C. P. and Low, P. S, "Selective targeting of malignant cells with cytotoxin-folate conjugates," *J. Drug Target.* 2(2): 101-112 (1994).

Leamon et al., "Folate-mediated drug delivery: effect of alternative conjugation chemistry," *J. Drug Target* 7(3): 157-169 (1999).

Leamon et al., "Synthesis and Biological Evaluation of EC20: A New Folate-Derived, (99m)Tc-Based Radiopharmaceutical," *Bioconjug. Chem.* 13(6): 1200-1210 (2002).

Leamon et al, "Cytotoxicity of folate-Pseudomonas exotoxin conjugates toward tumor cells. Contribution of translocation domain," *J. Biol. Chem.* 268(33): 24847-24854 (1993).

Lee et al., "Synthesis and evaluation of taxol-folic acid conjugates as targeted antineoplastics," *Bioorg Med Chem.* 10(7): 2397-2414, (2002).

Lee, R. J. and Huang, L., "Folate-Targeted, Anionic Liposome-Entrapped Polylysine-Condensed Dna For Tumor Cell-Specific Gene Transfer," *J. Biol. Chem.* 271(14): 8481-8487 (1996).

Lee, R. J. and Low, P. S., "Folate-mediated tumor cell targeting of liposome-entrapped doxorubicin in vitro," *Biochim. Biophys. Acta* 1233: 134-144 (1995).

Lee, R. J. and Low, P. S, "Delivery of liposomes into cultured KB cells via folate receptor-mediated endocytosis," *J. Biol. Chem.* 269(5): 3198-3204 (1994).

Lee et al, "Measurement of Endosome pH Following Folate Receptor-Mediated Endocytosis," *Biochim. Biophys. Acta* 1312(3): 237-242 (1996).

Lewis et al., "Receptor-mediated folate uptake is positively regulated by disruption of actin cytoskeleton," *Cancer Res.* 58(14): 2952-2956 (1998).

Liu et al., "Targeted Drug Delivery to Chemoresistant Cells: Folic Acid Derivatization of FdUMP[10] Enhances Cytotoxicity Toward 5-FU-Resistant Human Colorectal Tumor Cells," *J. Org. Chem.* 66: 5655-5663 (2001).

Lu, J. Y. and Low, P. S., "Folate targeting of haptens to cancer cell surfaces mediates immunotherapy of syngeneic murine tumors," *Cancer Immunol Immunother* 51: 153-162 (2002).

Lu et al., "Folate-targeted enzyme prodrug cancer therapy utilizing penicillin-V amidase and a doxorubicin prodrug," *J. Drug Target* 7(1): 43-53 (1999).

Lu, J. Y. and Low, P. S., "Folate-mediated delivery of macromolecular anticancer therapeutic agents," *Adv. Drug Del Rev* 54(5); 675-693-(2002).

Luo et al., "Efficient syntheses of pyrofolic acid and pteroyl azide, reagents for the production of carboxyl-differentiated derivatives of folic acid," *J. Am. Chem. Soc.* 119: 10004-10013 (1997).

Mathais et al., "Synthesis of [(99m)Tc]DTPA-folate and its evaluation as a folate-receptor-targeted radiopharmaceutical," *Bioconjug Chem.* 11(2): 253-257 (2000).

Mathais et al., "Receptor-mediated targeting of 67Ga-deferoxamine-folate to folate-receptor-positive human KB tumor xenografts," *Nucl Med Biol* 26(1): 23-25 (1999).

Mathias, C. J. and Green, M. A., "A kit formulation for preparation of [(111)In]In-DTPA-folate, a folate-receptor-targeted radiopharmaceutical," *Nucl. Med. Biol.* 25(6): 585-587 (1998).

Mathias et al., "Tumor-Selective Radiopharmaceutical Targeting Via Receptor-Mediated Endocytosis of Gallium-67-Deferoxamine-Folate," *J. Nucl. Med.* 37(6): 1003-1008 (1996).

Mathias et al., "Indium-111-DTPA-Folate as a potential folate-receptor-targeted radiopharmaceutical," *J. Nucl. Med.* 39(9): 1579-1585 (1998).

Matsui et al., "Studies on mitomycins. 3. The synthesis and properties of mitomycin derivatives," *J Antibiot 21*: 189-198 (1968).

Melani et al., "Targeting of interleukin 2 to human ovarian carcinoma by fusion with a single-chain Fv of antifolate receptor antibody," *Cancer Res.* 58(18): 4146-4154 (1998).

Melby et al., "Entry of protein toxins in polarized epithelial cells," *Cancer Res.* 53(8): 1755-1760 (1993).

Mislick et al., "Transfection of folate-polylysine DNA complexes: evidence for lysosomal delivery," *Bioconjug. Chem.* 6(5): 512-515 (1995).

Morshed et al., "Folate transport proteins mediate the bidirectional transport of 5-methyltetrahydrofolate in cultured human proximal tubule cells," *J. Nutr.* 127(6): 1137-1147 (1997).

Olsnes, et al., "Immunotoxins—entry into cells and mechanisms of action," *Immunol. Today* 10: 291-295 (1989).

Patrick et al., "Folate Receptors As Potential Therapeutic Targets in Choroid Plexus Tumors of Sv40 Transgenic Mice," *J. Neurooncol.* 32(2): 111-123 (1997).

Patrick et al., "Intracerebral bispecific ligand-antibody conjugate increases survival of animals bearing endogenously arising brain tumors," *Int. J. Cancer* 78(4): 470-79 (1998).

Prasad et al., "Functional coupling between a bafilomycin A1-sensitive proton pump and a probenecid-sensitive folate transporter in human placental choriocarcinoma cells," *Biochim. Biophys. Acta* 1222(2): 309 (1994).

Reddy et al., "Retargeting of viral vectors to the folate receptor endocytic pathway, J Control Release," 74(1-3): 77-82 (2001).

Reddy et al., "Optimization of folate-conjugated liposomal vectors for folate receptor-mediated gene therapy," *J. Pharm. Sci* 88(11): 1112-1118 (1999).

Rijnboutt et al., "Endocytosis of GPI-linked membrane folate receptor-alpha," *J. Cell Biol.* 132(1-2): 35-47 (1996).

Ross et al., "Differential regulation of folate receptor isoforms in normal and malignant tissues in vivo and in established cell lines. Physiologic and clinical implications," *Cancer* 73(9): 2432-2443, (1994).

Rothberg et al, "Cholesterol controls the clustering of the glycophospholipid-anchored membrane receptor for 5-methyltetrahydrofolate," *J. Cell Biol.* 111(6): 2931-2938 (1990).

Rothberg et al., "The glycophospholipid-linked folate receptor internalizes folate without entering the clathrin-coated pit endocytic pathway," *J. Cell Biol.* 110(3): 637-649 (1990).

Roy et al., "Targeting T cells against brain tumors with a bispecific ligand-antibody conjugate," *Int. J. Cancer* 76(5): 761-66 (1998).

Sadasivan et al., "The complete amino acid sequence of a human folate binding protein from KB cells determined from the cDNA," *J. Biol. Chem.* 264: 5806-5811, (1989).

Senter et al., "Development of a Drug-Release Strategy Based on the Reductive Fragmentation of Benzyl Carbamate Disulfides," *J. Org. Chem.* 55: 2975-2978 (1990).

Smart et al., "Protein kinase C activators inhibit receptor-mediated potocytosis by preventing internalization of caveolae," *J. Cell Biol.* 124(3): 307-313 (1994).

Smart et al., "Clustered folate receptors deliver 5-methyltetrahydrofolate to cytoplasm of MA104 cells," *J. Cell Biol.* 134(5): 1169-1177 (1996).

Li et al "Targeted delivery of antisense oligodeoxynucleotides by LPDII," *J. Liposome Res.* 7(1): 63 (1997).

Steinberg, G. and Borch, R. F., "Synthesis and Evaluation of Pteroic Acid-Conjugated Nitroheterocyclic Phosphoramidates as Folate Receptor-Targeted Alkylating Agents," *J. Med. Chem.* 44: 69-73 (2001).

Toffoli et al., "Overexpression of folate binding protein in ovarian cancers," *Int. J. Cancer* 74(2): 193-198 (1997).

Turek et al., "Endocytosis of folate-protein conjugates: ultrastructural localization in KB cells," *J. Cell Sci.* 106: 423-430 (1993).

Turk et al., "Characterization of a novel pH-sensitive peptide that enhances drug release from folate-targeted liposomes at endosomal pHs," *Biochim Biophys Acta* 1559(1): 56-68 (2002).

Varma, R. and Mayor, S., "GPI-anchored proteins are organized in submicron domains at the surface," *Nature* 394(6695): 798-801 (1998).

Vyas, D., et al., "A practical synthesis of mitomycin A and its analogs," *J Org Chem* 31:4307-4309 (1986).

Vogel et al., "Peptide-Mediated Release of Folate-Targeted Liposome Contents From Endosomal Compartments," *J. Am. Chem. Soc.* 118(7): 1581-1586 (1996).

Wang, S. and Low, P. S., "Folate-mediated targeting of antineoplastic drugs, imaging agents, and nucleic acids to cancer cells," *J. Control Rel* 53(1-3): 39-48 (1998).

Wang et al., "Delivery of antisense oligodeoxyribonucleotides against the human epidermal growth factor receptor into cultured KB cells with liposomes conjugated to folate via polyethylene glycol," *Proc. Natl. Acad. Sci. USA* 92(8): 3318-3322 (1995).

Wang et al., "Synthesis, purification, and tumor cell uptake of 67Ga-deferoxamine—folate, a potential radiopharmaceutical for tumor imaging," *Bioconj. Chem.* 7(1): 56-62 (1996).

Wang et al., "Design and synthesis of [111In]DTPA-folate for use as a tumor-targeted radiopharmaceutical," *Bioconjug Chem.* 8(5): 673-679 (1997).

Weitman et al., Distribution of the folate receptor GP38 in normal and malignant cell lines and tissues, Cancer Res., 52(12), 3396-3401, 1992.

Weitman et al., "Cellular localization of the folate receptor: potential role in drug toxicity and folate homeostasis," *Cancer Res.* 52(23): 6708-6711 (1992).

Wiener et al., "Targeting dendrimer-chelates to tumors and tumor cells expressing the high-affinity folate receptor," *Invest. Radiol.* 32(12): 748-54 (1997).

Wu et al., "Clustering of GPI-anchored folate receptor independent of both cross-linking and association with caveolin," *J. Membr. Biol.* 159(2): 137-147 (1997).

Zimmerman, J., "Folic acid transport in organ-cultured mucosa of human intestine. Evidence for distinct carriers," *Gastroenterol.* 99(4): 964-972 (1990).

Taiwan Patent Application No. 093101735 Search Report dated Jul. 14, 2007, 1 page.

Akihiro Hosomi, Makoto Arita, Yuji Sato, Chikako Kiyose, Tadahiko Ueda, Osamu Igarashi, Hiroyuki Arai, Keizo Inoue; "Affinity for a-tocopherol transfer protein as a determinant of the biological activities of vitamen E analogs," journal article, Federation of European Biochemical Societies, 1997, vol. 409, pp. 105-108.

Kazui Shimizu, Akira Kawase, Tsuyoshi Haneishi, Yasuharu Kato, Takamitsu Kobayashi, Nobuo Sekiguchi, Tessai Yamamoto, Masaki Ishigai, Kazuo Tokuda, Tomochika Matsushita, Shin Shimaoka, and Kazumi Morikawa; "Novel vitamin D3 antipsoriatic antedrugs: 16-En-22-oxa-1a,25-(OH)2D3 analogs," Bioorganic & Medicinal Chemistry 14, 2006, pp. 1838-1850.

Hisashi Takasu, Atsuko Sugita, Yasushi Uchiyama, Nobuyoshi Katagiri, Makoto Okazaki, Etsuro Ogata, Kyoji Ikeda; "c-Fos protein as a target of anti-osteoclastogenic action of vitamin D, and synthesis of new analogs," journal article, The Journal of Clinical Investigation, vol. 116, No. 2, Feb. 2006, pp. 528-535.

Masato Shimizu, Yukiko Miyamoto, Emi Kobayashi, Mika Shimazaki, Keiko Yamamoto, Wolfgang Reischl, Sachiko Yamada; "Synthesis and biological activities of new 1a,25-dihydroxy-19-norvitamin D3 analogs with modifications in both the A-ring and the side chain," journal article, Biorganic & Medicinal Chemistry, 2006, eighteen pages.

E. S. Agoston, M. A. Hatcher, T. W. Kensler, G. H. Posner; Vitamin D Analogs as Anti-Carcinogenic Agents, journal article, Anti-Cancer Agents in Medicinal Chemistry, 2006, pp. 53-71.

G. Robbin Westerhof, Jan C. Schornagel, Ietje Kathmann, Ann L. Jackman, Andre Rosowsky, Ronald A. Forsch, John B. Hynes, F. Thomas Boyle, Godefridus J. Peters, Herbert M. Pinedo, and Gerrit Jansen; "Carrier-and Receptor-Mediated Transport of Folate Antagonists Targeting Folate-Dependent Enzymes: Correlates of Molecular-Structure and Biological Activity," journal article, Molecular Pharmacology, 1995, vol. No. 48, pp. 459-471.

Eugene C. Roberts and Y. Fulmer Shealy, "Folic Acid Analogs. Modifications in the Benzene-Ring Region. 3. Neohomofolic and Neobishomofolic Acids. An Improved Synthesis of Folic Acid and Its Analogs.", journal article, Journal of Medicinal Chemistry, 1973, vol. 16, No. 6, pp. 697-699.

Eugene C. Roberts and Y. Fulmer Shealy, "Folic Acid Analogs. Modifications in the Benzene-Ring Region. 2. Thiazole Analogs," journal article, Journal of Medicinal Chemistry, 1972, vol. 15, No. 12, pp. 1310-1312.

Eugene C. Roberts and Y. Fulmer Shealy, "Folic Acid Analogs. Modifications in the Benzene-Ring Region. 1. 2'- and 3'-Azafolic Acids," journal article, Journal of Medicinal Chemistry, 1971, vol. 14, No. 2, pp. 125-130.

Louis T. Weinstock, Bernard F. Grabowski, and C. C. Cheng, "Folic Acid Analogs. II. p-{[2,6-Diamino-8-purinyl)methyl]amino}-benzoyl-L-glutamic Acid and Related Compounds," journal article, Journal of Medicinal Chemistry, 1970, vol. 13, No. 5, pp. 995-997.

Lothar Bock, George H. Miller, Klaus-J. Schaper, and Joachim K. Seydel, "Sulfonamide Structure-Activity Relationships in a Cell-Free System. 2. Proof for the Formation of a Sulfonamide-Containing Folate Analog.," journal article, Journal of Medicinal Chemistry, 1974, vol. 17, No. 1, pp. 23-28.

Eugene C. Roberts and Y. Fulmer Shealy, "Folic Acid Analogs. Modifications in the Benzene-Ring Region. 4. 3'- Ethyl- and 3'-Isopropylfolic Acids," journal article, Journal of Medicinal Chemistry, 1974, vol. 17, No. 2, pp. 219-222.

William W. Lee, Abelardo P. Martinez, and Leon Goodman, "Folic Acid Antagonists. Methotrexate Analogs Containing Spurious Amino Acids. Dichlorohomofolic Acid.", journal article, Journal of Medicinal Chemistry, 1974, vol. 17, No. 3, pp. 326-330.

Y. H. Kim, Y. Gaumont, R. L. Kisliuk, and H. G. Mautner, "Synthesis and Biological Activity of 10-Thia-10-deaza Analogs of Folic Acid, Pteroic Acid, and Related Compounds," journal article, Journal of Medicinal Chemistry, 1975, vol. 18, No. 8, pp. 776-780.

M. G. Nair and Patricia T. Campbell, "Folate Analogues Altered in the C9-N10 Bridge Region. 10-Oxafolic Acid and 10-Oxaaminopterin," journal article, Journal of Medicinal Chemistry, 1976, vol. 19, No. 6, pp. 825-829.

Laurence T. Plante, Elizabeth J. Crawford, and Morris Friedkin; "Polyglutamyl and Polylysyl Derivatives of the Lysine Analogues of Folic Acid and Homofolic Acid," journal article, Journal of Medicinal Chemistry, 1976, vol. 19, No. 11, pp. 1295-1299.

John B. Hynes, Donald E. Eason, Claudia M. Garrett, and Perry L. Colvin, Jr., "Quinazolines as Inhibitors of Dihydrofolate Reductase. 4. Classical Analogues of Folic and Isofolic Acids," journal article, Journal of Medicinal Chemistry, 1977, vol. 20, No. 4, pp. 588-591.

John E. Oatis, Jr. and John B. Hynes, "Synthesis of Quinazoline Analogues of Folic Acid Modified at Position 10," journal article, Journal of Medicinal Chemistry, 1977, vol. 20, No. 11, pp. 1393-1396.

M. G. Nair, P. Colleen O'Neal, C. M. Baugh, Roy L. Kisliuk, Y. Gaumont, and Michael Rodman; "Folate Analogues Altered in the C9-N10 Bridge Region: N10-Tosylisohomofolic Acid and N10-Tosylisohomoaminopterin," journal article, Journal of Medicinal Chemistry, 1978, vol. 21, No. 7, pp. 673-677.

M. G. Nair, Shiang-Yuan Chen, Roy L. Kisliuk, Y. Gaumont, and D. Strumpf; "Folate Analogues Altered in the C9-N10 Bridge Region: 11-Thiohomofolic Acid," journal article, Journal of Medicinal Chemistry, 1979, vol. 22, No. 7, pp. 850-855.

M. G. Nair, Colleen Saunders, Shiang-Yuan Chen, Roy L. Kisliuk, and Y. Gaumont; "Folate Analogues Altered in the C9-N10 Bridge Region. 14. 11-Oxahomofolic Acid, a Potential Antitumor Agent," journal article, J. Med. Chem., 1980, vol. 23, pp. 59-65.

M. G. Nair, Timothy W. Bridges, Timothy J. Henkel, Roy L. Kisliuk, Y. Gaumont, and F. M. Sirotnak; "Folate Analogues Altered in the C9-N10 Bridge Region. 18. Synthesis and Antitumor Evaluation of 11-Oxahomoaminopterin and Related Compounds," journal article, J. Med. Chem., 1981, vol. 24, pp. 1068-1073.

Carroll Temple, Jr., L. Lee Bennett, Jr., Jerry D. Rose, Robert D. Elliott, John A. Montgomery, and John H. Mangum; "Synthesis of Pseudo Cofactor Analogues as Potential Inhibitors of the Folate Enzymes," journal article, J. Med. Chem., 1982, vol. 25, pp. 161-166.

M. G. Nair, Eldrige B. Otis, Roy L. Kisliuk, and Y. Gaumont, "Folate Analogues. 20. Synthesis and Antifolate Activity of 1, 2, 3, 4, 5, 6,-Hexahydrohomofolic Acid," journal article, J. Med. Chem., 1983, vol. 26, pp. 135-140.

M. G. Nair, David C. Salter, R. L. Kisliuk, Y. Gaumont, G. North, and F. M. Sirotnak; "Folate Analogues. 21. Synthesis and Antifolate and Antitumor Activities of N10-(Cyanomethyl)-5,8-dideazafolic Acid," journal article, J. Med. Chem., 1983, vol. 26, pp. 605-607.

M. G. Nair, Otha, C. Salter, Roy L. Kisliuk, Y. Gaumont, and G. North; "Folate Analogues. 22. Synthesis and Biological Evaluation of Two Analogues of Dihydrofolic Acid Processing a 7,8- Dihydro-8-oxapterin Ring System," journal article, J. Med. Chem., 1983, vol. 26, pp. 1164-1168.

Derrick Lonsdale, "A Review of the Biochemistry, Metabolism and Clinical Benefits of Thiamin(e) and Its Derivatives," publication, Advance Access Publication, vol. 3, Feb. 2006, pp. 49-59.

K. Nosaka, H. Nishimura, and A. Iwashima; "Separate Determination of Anticoccidial Thiamine Analogs by High-performance Liquid Chromatography," journal article, ActaA Vitaminol. Et Enzymol, 1984, vol. 6 (2), pp. 137-142.

Charles T. Kandiko, Daniel Smith, and Brian K. Yamamoto; "Inhibition of Rat Brain Pyruvate Dehydrogenase by Thiamine Analogs," journal article, Biochemical Pharmacology, vol. 37, No. 22, pp. 4375-4380, 1988.

Christina Spry, Christina L. L. Chai, Kiaran Kirk, and Kevin J. Saliba, "A Class of Pantothenic Acid Analogs Inhibits Plasmodium Falciparum Pantothenate Kinase and Represses the Proliferation of Malaria Parasites," journal article, Antimicrobial Agents and Chemotherapy, Nov. 2005, pp. 4649-4657.

Dale R. Sargent, G. Gil Clifton, Sarah R. Bryant, and Charles G. Skinner; "Antimetabolites of Pantothenic Acid, Ureido- and Carbamoyl-Derivatives," journal article, Texas Reports on Biology and Medicine, 1975, vol. 33, No. 3, pp. 433-443.

Abstract, Acta Vitaminol Enzymol, 1982, vol. 4 (1-2), pp. 87-97.

Hiroyuki Kagechika and Koichi Shudo, "Synthetic Retinoids: Recent Developments Concerning Structure and Clinical Utility," journal article, Journal of Medicinal Chemistry, Sep. 22, 2005, vol. 48, No. 19, pp. 5875-5883.

Y. Fulmer Shealy, "Synthesis and Evaluation of Some New Retinoids for Cancer Chemoprevention," Preventive Medicine, 1989, vol. 18, pp. 624-645.

Walter Landuer and Ellen M. Clark, "The Interaction in Teratogenic Activity of the Two Niacin Analogs 3-acetylpyridine and 6-aminonicotinamide," Storrs Agricultural Experiment Station, University of Connecticut, undated, pp. 253-258.

Paul Renz, Inka Pfitzner, Birgit Endres, and Oliver Hasselwander, "Synthesis of 4-Aza-5, 6-diethylbenzimidazole and Biosynthetic Preparation of 4- and 7-Aza-5, 6-dimethylbenzimidazolylcobamide," journal article, Z. Naturforsch, 1997, vol. 52c, pp. 287-291.V.

William A. Ayers, "Effect of Vitamin B12 and Analogs on the Respiration of a Marine Bacterium," journal article, Archives of Biochemistry and Biophysics, vol. 96, 1962, pp. 210-215.

Tetsuo Toraya and Saburo Fukui, "Immobilized Derivatives of Vitamin B12 Coenzyme and Its Analogs," journal article, Methods in Enzymology, vol. 67, pp. 57-66.

Masatoshi Ueda and Kazuhisa Taketa, "Effect of Vitamin B12 Derivatives on Urinary Excretion of Methylmalonic Acid in Liver Diseases," journal article, Acta Med. Okayama, vol. 24, 1970, pp. 365-372.

Tetsuo Toraya and Saburo Fukui, "The Synthesis of Several Immobilized Derivatives of Vitamin B12 Coenzyme and Their Use as Affinity Adsorbents for a Study of Interactions of Diol Dehydrase with the Coenzyme," The Journal of Biological Chemistry, vol. 255, No. 8., Issue of Apr. 25, 1980, pp. 3520-3525.

Yusuke Takahata, Ari Nishizawa, Ichiro Kojima, Mamoru Yamanishi, and Tetsuo Toraya, "Synthesis, Properties and Microbiological Activity of Hydrophobic Derivatives of Vitamin B12," journal article, J. Nutr. Sci. Vitaminol., vol. 41, 1995, pp. 515-526.

Maya Kamao, Yoshitomo Suhara, Naoko Tsugawa, Toshio Okano, "Determination of Plasma Vitamin K by High Performance Liquid Chromatography with Fluorescence Detection Using Vitamin K Analogs as Internal Standards," journal article, Journal of Chromatography B, vol. 816, 2005, pp. 41-48.

Yuji Nishikawa, Brian I. Carr, Meifang Wang, Siddhartha Kar, Frances Finn, Paul Dowd, Zhizhen N. Zheng, Jeffrey Kerns, and Sriram Naganathan, "Growth Inhibition of Hepatoma Cells Induced by Vitamin K and Its Analogs," journal article, The Journal of Biological Chemistry, vol. 270, No. 47, Issue of Nov. 24, 1995, pp. 28304-28310.

Donald O. Mack, Max Wolfensberger, Jean-Marie Girardot, Julie A Miller, and B. Connor Johnson, "The Carboxylation Activity of Vitamin K Analogs with Substitutions at Position 2, 3, or 5," The Journal of Biological Chemistry, vol. 254, Issue of Apr. 25, 1979, pp. 2656-2664.

Donald M. Mock and Greg M. Heird, "Urinary Biotin Analogs Increase in Humans During Chronic Supplementation: the Analogs are Biotin Metabolites," The American Physiological Society, 1997, pp. 83-85.

Timothy M. Shoup, Alan J. Fischman, Shreen Jaywook, John W. Babich, H. William Strauss, and David R. Elmaleh; "Synthesis of Fluorine-18-Labeled Biotin Derivatives: Biodistribution and Infection Localization," journal article, J. Nucl. Med. 1994, vol. 35, pp. 1685-1690.

David L. Vesely, Henry C. Wormser, and Hanley N. Abramson, "Biotin Analogs Activate Guanylate Cyclase," journal article, Molecular and Cellular Biochemistry, vol. 60, 1984, pp. 109-114.

J. P. Lambooy, "Riboflavin Analogs Utilized for Metabolism by a Lactobacillus Casei Mutant," Int. J. Biochem., vol. 16, No. 2, 1984, pp. 231-234.

Peter Nielsen, Peter Rauschenbach, and Adelbert Bacher, "Phosphates of Riboflavin and Riboflavin Analogs: A Reinvestigation by High-Performance Liquid Chromatography," journal article, Analytical Biochemistry, vol. 130, 1983, pp. 359-368.

Arya, et al., "Design and Synthesis of Analogs of Vitamin E: Antiproliferative Activity Against Human Breast Adenocarcinoma Cells," journal article, Bioorganic & Medicinal Chemistry Letters, vol. 8, 1998, pp. 2433-2438.

Daniel Trachewsky, "Antihypertensive Effect of Riboflavin Analogs in Rats with Mineralocorticoid-Induced Hypertension," journal article, Hypertension, vol. 3, No. 1, Jan.-Feb. 1981, pp. 75-80.

W.A. Skinner, R. M. Parkhurst, and J. Scholler, "Structure-Activity Relations in the Vitamin E Series. II. Derivatives of a-Tocopherol Substituted at the 5-Methyl Group," journal article, Skinner, Parkhurst, Scholler, and Schwarz, vol. 12, pp. 64-66.

J. Neuzil, K. Kagedal, L. Andrea, C. Weber, and U.T. Brunk, "Vitamin E Analogs: A New Class of Multiple Action Agents with Anti-Neoplastic and Anti-Atherogenic Activity," Apoptosis, vol. 7, 2002, pp. 179-187.

I. Politis, A. Voudouri, I. Bizelis, and G. Zervas, "The Effect of Various Vitamin E Derivatives on the Urokinase-Plasminogen Activator System of Ovine Macrophages and Neutrophils," British Journal of Nutrition, vol. 89, 2003, pp. 259-265.

Xiu-Fang Wang, Paul K. Witting, Brian A. Salvatore, and Jiri Neuzil, "Vitamin E Analogs Trigger Apoptosis in HER2/erbB2-Overexpressing Breast Cancer Cells by Signaling Via the Mitochondrial Pathway," Biochemical and Biophysical Research Communication, vol. 326, 2005, pp. 282-289.

U.S. Appl. No. 10/513,372, filed Nov. 3, 2004, Vlahov et al.
U.S. Appl. No. 11/632,895, filed Jan. 19, 2007, Vlahov et al.
U.S. Appl. No. 11/908,695, filed Sep. 13, 2007, Xu et al.
U.S. Appl. No. 12/064,163, filed Feb. 19, 2008, Leamon et al.
U.S. Appl. No. 12/064,191, filed Feb. 19, 2008, Vlahov et al.

Douglas, J. T., Rogers, B. E., Rosenfeld, M. E., Michael, S. I., Fend, M., Curiel, D. T., "Targeted Gene Delivery by Tropism-Modified Adenoviral Vectors," Nat. Biotechnol., vol. 14, 1996, pp. 1574-1578.

Reddy, J. A., Low, P. S., "Folate-Mediated Targeting of Therapeutic and Imaging Agents to Cancers," Crit. Rev. Ther. Drug Carrier Syst., vol. 15, No. 6, 1998, pp. 587-627.

* cited by examiner

VITAMIN RECEPTOR BINDING DRUG DELIVERY CONJUGATES

CROSS-REFERENCE TO RELATED APPLICATIONS

This application claims priority under 35 U.S.C. § 119(e) to U.S. patent application Ser. No. 60/442,845, entitled "Vitamin-Receptor Binding Drug Delivery Conjugates," filed Jan. 27, 2003, U.S. patent application Ser. No. 60/492,119, entitled "Vitamin-Receptor Binding Drug Delivery Conjugates," filed Aug. 1, 2003, and U.S. patent application Ser. No. 60/516,188, entitled "Vitamin-Receptor Binding Drug Delivery Conjugates," filed Oct. 31, 2003. The entirety of the disclosures of each of these applications are incorporated herein by reference.

FIELD OF THE INVENTION

The present invention relates to compositions and methods for use in targeted drug delivery. More particularly, the invention is directed to vitamin receptor binding drug delivery conjugates for use in treating disease states caused by pathogenic cell populations and to a method and pharmaceutical composition therefor.

BACKGROUND

The mammalian immune system provides a means for the recognition and elimination of tumor cells, other pathogenic cells, and invading foreign pathogens. While the immune system normally provides a strong line of defense, there are many instances where cancer cells, other pathogenic cells, or infectious agents evade a host immune response and proliferate or persist with concomitant host pathogenicity. Chemotherapeutic agents and radiation therapies have been developed to eliminate, for example, replicating neoplasms. However, many of the currently available chemotherapeutic agents and radiation therapy regimens have adverse side effects because they work not only to destroy pathogenic cells, but they also affect normal host cells, such as cells of the hematopoietic system. The adverse side effects of these anticancer drugs highlight the need for the development of new therapies selective for pathogenic cell populations and with reduced host toxicity.

Researchers have developed therapeutic protocols for destroying pathogenic cells by targeting cytotoxic compounds to such cells. Many of these protocols utilize toxins conjugated to antibodies that bind to antigens unique to or overexpressed by the pathogenic cells in an attempt to minimize delivery of the toxin to normal cells. Using this approach, certain inmmunotoxins have been developed consisting of antibodies directed to specific antigens on pathogenic cells, the antibodies being linked to toxins such as ricin, Pseudomonas exotoxin, Diptheria toxin, and tumor necrosis factor. These inmunotoxins target pathogenic cells, such as tumor cells, bearing the specific antigens recognized by the antibody (Olsnes, S., *Immunol. Today*, 10, pp. 291-295, 1989; Melby, E. L., *Cancer Res.*, 53(8), pp. 1755-1760, 1993; Better, M. D., PCT Publication Number WO 91/07418, published May 30, 1991).

Another approach for targeting populations of pathogenic cells, such as cancer cells or foreign pathogens, in a host is to enhance the host immune response against the pathogenic cells to avoid the need for administration of compounds that may also exhibit independent host toxicity. One reported strategy for immunotherapy is to bind antibodies, for example, genetically engineered multimeric antibodies, to the surface of tumor cells to display the constant region of the antibodies on the cell surface and thereby induce tumor cell killing by various immune-system mediated processes (De Vita, V. T., *Biologic Therapy of Cancer*, 2d ed. Philadelphia, Lippincott, 1995; Soulillou, J. P., U.S. Pat. No. 5,672,486). However, these approaches have been complicated by the difficulties in defining tumor-specific antigens.

SUMMARY OF THE INVENTION

In an attempt to develop effective therapies specific for pathogenic cells and with minimized toxicity for normal cells, vitamin receptor binding drug delivery conjugates have been developed. The present invention is applicable to populations of pathogenic cells that cause a variety of pathologies in host animals. The pathogenic cells that can be treated with the drug delivery conjugates of the present invention include tumor cells, infectious agents such as bacteria and viruses, bacteria- or virus-infected cells, and any other type of pathogenic cells that uniquely express, preferentially express, or overexpress vitamin receptors or receptors that bind vitamin analogs or derivatives.

In one embodiment there is provided a vitamin receptor binding drug delivery conjugate. The drug delivery conjugate comprises a vitamin receptor binding moiety, a bivalent linker, and a drug. As used herein, "V" refers to a vitamin receptor binding moiety and includes vitamins, and vitamin receptor binding analogs or derivatives thereof, and the term "vitamin or analog or derivative thereof" refers to vitamins and analogs and derivatives thereof that are capable of binding vitamin receptors. As used herein, "D" refers to drugs and includes analogs or derivatives thereof. The vitamin, or the analog or the derivative thereof, is covalently bound to the bivalent linker (L), and the drug, or the analog or the derivative thereof, is also covalently bound to the bivalent linker (L). The bivalent linker (L) can comprise multiple linkers. For example, the bivalent linker (L) can comprise one or more components selected from spacer linkers ($l_s$), releasable linkers ($l_r$), and heteroatom linkers ($l_H$), and combinations thereof, in any order.

Drug delivery conjugates that illustrate this embodiment include:

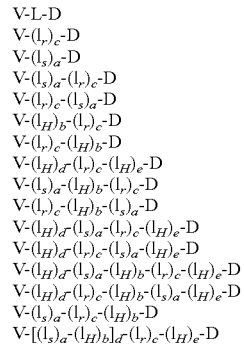

wherein a, b, c, d, and e are each independently 0, 1, 2, 3, or 4, ($l_s$), ($l_H$), and ($l_r$) are as defined herein, V is a vitamin, or analog or derivative thereof, and D is a drug, or analog or derivative thereof, and where the bivalent L encompasses one or a variety of ($l_s$), ($l_H$), and ($l_r$), in any order and in any combination. It is understood that the foregoing examples of the bivalent linker L are intended to illustrate, and not limit, the wide variety of assemblies of $(l_H)$, $(l_s)$, and $(l_r)$ that the bivalent linker encompasses.

It is understood that each of the spacer, heteroatom, and releasable linkers are bivalent. It should be further understood that the connectivity between each of the various spacer, heteroatom, and releasable linkers, and between the various spacer, heteroatom, and releasable linkers and D and/or V, as defined herein, may occur at any atom found in the various spacer, heteroatom, and releasable linkers, and is not necessarily at any apparent end of any of the various spacer, heteroatom, or releasable linkers. For example, in the illustrative embodiment where the bivalent linker is:

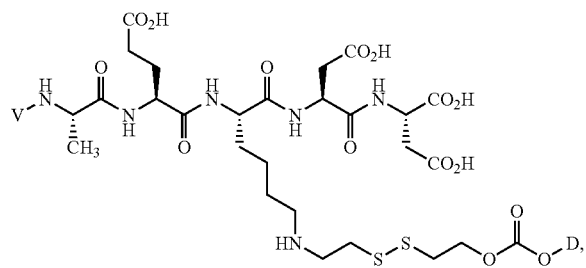

i.e. where the bivalent linker L is $-(l_H)-(l_s)_5-(l_r-l_H)_2-D$, where $(l_H)$ is nitrogen, $(l_s)_5$ is Ala-Glu-Lys-Asp-Asp, and $(l_r-l_H)_2$ is —$(CH_2)_2$—S—S—$(CH_2)_2$—O—C(O)—O—, respectively, the $(l_r-l_H)_2$ linker is connected to middle portion of the $(l_s)_5$ linker.

In another embodiment there is provided a vitamin receptor binding drug delivery conjugate. The drug delivery conjugate comprises a vitamin receptor binding moiety, a bivalent linker (L), and a drug, and the bivalent linker (L) comprises one or more heteroatom linkers $(l_H)$. The vitamin receptor binding moiety is covalently bound to the bivalent linker (L) through a first heteroatom linker $(l_H)_d$ and the drug is covalently bound to the bivalent linker (L) through a second heteroatom linker $(l_H)_e$. The bivalent linker (L) also comprises one or more spacer linkers and releasable linkers, wherein the spacer linkers and the releasable linkers may be covalently linked to each other through a third heteroatom linker $(l_H)_b$. A drug delivery conjugate that illustrates this embodiment is as follows:

$$V-(l_H)_d-(l_s)_a-(l_H)_b-(l_r)_c-(l_H)_e-D$$

wherein a, b, c, d, and e are each independently 0, 1, 2, 3, or 4, $(l_s)$, $(l_H)$, and $(l_r)$, and V and D are as defined herein, and where the bivalent linker L encompasses $(l_s)$, $(l_H)$, and $(l_r)$ as illustrated.

In another embodiment there is provided a vitamin receptor binding drug delivery conjugate. The drug delivery conjugate comprises a vitamin receptor binding moiety, a bivalent linker (L), and a drug, and the bivalent linker (L) comprises an heteroatom linker $(l_H)$. The vitamin receptor binding moiety is a vitamin, or an analog or a derivative thereof, and the drug includes analogs or derivatives thereof. The vitamin, or the analog or the derivative thereof, is covalently bound to the bivalent linker (L) and the drug, or the analog or the derivative thereof, is covalently bound to the bivalent linker (L). The bivalent linker (L) also comprises spacer linkers and releasable linkers, and the spacer linkers and the releasable linkers may be covalently bound to each other through the heteroatom linker. A drug delivery conjugate that illustrates this embodiment is as follows:

$$V-(l_s)_a-(l_H)_b-(l_r)_c-D$$

wherein a, b, and c are each independently 0, 1, 2, 3, or 4, $(l_s)$, $(l_H)$, and $(l_r)$, and V and D are as defined herein, and where the bivalent linker L encompasses $(l_s)$, $(l_H)$, and $(l_r)$ as illustrated.

In another embodiment, a vitamin receptor binding drug delivery conjugate of the general formula V-L-D is provided. In this embodiment, L is constructed from one or more linkers $(l_r)_c$, $(l_s)_a$, and $(l_H)_b$, and combinations thereof, in any order, where $(l_r)$ is a releasable linker, $(l_s)$ is a spacer linker, $(l_H)$ is an heteroatom linker, and a, b, and c are each independently 0, 1, 2, 3, or 4, V is a vitamin, or an analog or a derivative thereof, and D is a drug, or an analog or a derivative thereof. It is appreciated that the drug delivery conjugates described herein may include a bivalent linker that has more than one spacer linker, releasable linker, or heteroatom linker. For example, bivalent linkers that include two or more releasable linkers $(l_r)$ are contemplated. Further, configurations of such releasable linkers include bivalent linkers where the releasable linkers are covalently linked to each other, and where the releasable linkers are separated from each other by one or more heteroatom linkers and/or spacer linkers.

In another embodiment, a vitamin receptor binding drug delivery conjugate of the general formula V-L-D is described, wherein L is a bivalent linker comprising $(l_s)_a$ and $(l_H)_b$, and combinations thereof in any order, wherein $(l_s)_a$ and $(l_H)_b$, and V and D are as defined herein. In this embodiment, the drug in the drug delivery conjugate can be a hapten such as, but not limited to, fluorescein, dinitrophenyl, and the like.

In another embodiment, a vitamin receptor binding drug delivery conjugate of the general formula V-L-D is described, wherein L is a bivalent linker comprising $(l_s)_a$, $(l_H)_b$, and $(l_r)_c$, and combinations thereof in any order, wherein $(l_s)_a$ and $(l_H)_b$, and V and D are as defined herein, and where at least one of $(l_r)$ is not a disulfide. It is appreciated that bivalent linkers in this embodiment having more than one $(l_r)$, i.e. where c is greater than 1, may include a disulfide releasable linker in addition to another or other releasable linkers.

In one aspect of the various vitamin receptor binding drug delivery conjugates described herein, the bivalent linker comprises an heteroatom linker, a spacer linker, and a releasable linker taken together to form 3-thiosuccinimid-1-ylalkyloxymethyloxy, where the methyl is optionally substituted with alkyl or substituted aryl.

In another aspect, the bivalent linker comprises an heteroatom linker, a spacer linker, and a releasable linker taken together to form 3-thiosuccinimid-1-ylalkylcarbonyl, where the carbonyl forms an acylaziridine with the drug, or analog or derivative thereof.

In another aspect, the bivalent linker comprises an heteroatom linker, a spacer linker, and a releasable linker taken together to form 1-alkoxycycloalkylenoxy.

In another aspect, the bivalent linker comprises a spacer linker, an heteroatom linker, and a releasable linker taken together to form alkyleneaminocarbonyl(dicarboxylarylene) carboxylate.

In another aspect, the bivalent linker comprises a releasable linker, a spacer linker, and a releasable linker taken together to form dithioalkylcarbonylhydrazide, where the hydrazide forms an hydrazone with the drug, or analog or derivative thereof.

In another aspect, the bivalent linker comprises an heteroatom linker, a spacer linker, and a releasable linker taken together to form 3-thiosuccinimid-1-ylalkylcarbonylhydrazide, where the hydrazide forms an hydrazone with the drug, or analog or derivative thereof In another aspect, the bivalent linker comprises an heteroatom linker, a spacer linker, an heteroatom linker, a spacer linker, and a releasable linker taken together to form 3-thioalkylsulfonylalkyl(disubstituted silyl)oxy, where the disubstituted silyl is substituted with alkyl or optionally substituted aryl.

In another aspect, the bivalent linker comprises a plurality of spacer linkers selected from the group consisting of the naturally occurring amino acids and stereoisomers thereof.

In another aspect, the bivalent linker comprises a releasable linker, a spacer linker, and a releasable linker taken together to form 3-dithioalkyloxycarbonyl, where the carbonyl forms a carbonate with the drug, or analog or derivative thereof.

In another aspect, the bivalent linker comprises a releasable linker, a spacer linker, and a releasable linker taken together to form 3-dithioarylalkyloxycarbonyl, where the carbonyl forms a carbonate with the drug, or analog or derivative thereof, and the aryl is optionally substituted.

In another aspect, the bivalent linker comprises an heteroatom linker, a spacer linker, a releasable linker, a spacer linker; and a releasable linker taken together to form 3-thiosuccinimid-1-ylalkyloxyalkyloxyalkylidene, where the alkylidene forms an hydrazone with the drug, or analog or derivative thereof, each alkyl is independently selected, and the oxyalkyloxy is optionally substituted with alkyl or optionally substituted aryl.

In another aspect, the bivalent linker comprises a releasable linker, a spacer linker, and a releasable linker taken together to form 3-dithioalkyloxycarbonylhydrazide.

In another aspect, the bivalent linker comprises a releasable linker, a spacer linker, and a releasable linker taken together to form 3-dithioalkylamino, where the amino forms a vinylogous amide with the drug, or analog or derivative thereof.

In another aspect, the bivalent linker comprises a releasable linker, a spacer linker, and a releasable linker taken together to form 3-dithioalkylamino, where the amino forms a vinylogous amide with the drug, or analog or derivative thereof, and the alkyl is ethyl.

In another aspect, the bivalent linker comprises a releasable linker, a spacer linker, and a releasable linker taken together to form 3-dithioalkylaminocarbonyl, where the carbonyl forms a carbamate with the drug, or analog or derivative thereof.

In another aspect, the bivalent linker comprises a releasable linker, a spacer linker, and a releasable linker taken together to form 3-dithioalkylaminocarbonyl, where the carbonyl forms a carbamate with the drug, or analog or derivative thereof, and the alkyl is ethyl.

In another aspect, the bivalent linker comprises a releasable linker, a spacer linker, and a releasable linker taken together to form 3-dithioarylalkyloxycarbonyl, where the carbonyl forms a carbamate or a carbamoylaziridine with the drug, or analog or derivative thereof.

In one aspect, the releasable, spacer, and heteroatom linkers may be arranged in such a way that subsequent to the cleavage of a bond in the bivalent linker, released functional groups chemically assist the breakage or cleavage of additional bonds, also termed anchimeric assisted cleavage or breakage. An illustrative embodiment of such a bivalent linker or portion thereof includes compounds having the formula:

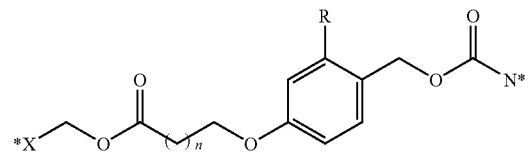

where X is an heteroatom, such as nitrogen, oxygen, or sulfur, n is an integer selected from 0, 1, 2, and 3, R is hydrogen, or a substituent, including a substituent capable of stabilizing a positive charge inductively or by resonance on the aryl ring, such as alkoxy, and the like, and the symbol (*) indicates points of attachment for additional spacer, heteroatom, or releasable linkers forming the bivalent linker, or alternatively for attachment of the drug, or analog or derivative thereof, or the vitamin, or analog or derivative thereof It is appreciated that other substituents may be present on the aryl ring, the benzyl carbon, the alkanoic acid, or the methylene bridge, including but not limited to hydroxy, alkyl, alkoxy, alkylthio, halo, and the like. Assisted cleavage may include mechanisms involving benzylium intermediates, benzyne intermediates, lactone cyclization, oxonium intermediates, beta-elimination, and the like. It is further appreciated that, in addition to fragmentation subsequent to cleavage of the releasable linker, the initial cleavage of the releasable linker may be facilitated by an anchimerically assisted mechanism.

In another embodiment, a vitamin receptor binding drug delivery conjugate intermediate is provided. The intermediate comprises a vitamin receptor binding moiety, a bivalent linker, having a first end and a second end, and a coupling group. The vitamin receptor binding moiety is a vitamin, or an analog or a derivative thereof, and the coupling group is a nucleophile, an electrophile, or a precursor thereof The vitamin receptor binding moiety is covalently attached to the bivalent linker at the first end of the bivalent linker, and the coupling group is covalently attached to the bivalent linker at the second end of the bivalent linker, and the bivalent linker comprises one or more spacer linkers, releasable linkers, and heteroatom linkers, and combinations thereof, in any order.

In another embodiment, a vitamin receptor binding drug delivery conjugate intermediate is described. The intermediate comprises a bivalent linker, having a first end and a second end, a drug, or an analog or a derivative thereof, and a coupling group. The bivalent linker comprises one or more components selected from spacer linkers, releasable linkers, and heteroatom linkers, as described herein. The coupling group is covalently attached to the bivalent linker at the first end of the bivalent linker, and the drug or analog or derivative thereof is covalently attached to the bivalent linker at the second end of the bivalent linker. Further, the coupling group is a nucleophile, an electrophile, or a precursor thereof, capable of forming a covalent bond with a vitamin receptor binding moiety, where the vitamin receptor binding moiety is a vitamin, or an analog or a derivative thereof.

In another illustrative embodiment of the vitamin receptor binding drug delivery conjugate intermediate described herein, the coupling group is a Michael acceptor, and the bivalent linker includes a releasable linker having the formula —C(O)NHN=, —NHC(O)NHN=, or —CH$_2$C(O)NHN=. In one illustrative aspect of the vitamin receptor binding drug delivery conjugate intermediate described herein, the coupling group and the bivalent linker are taken together to form a compound having the formula:

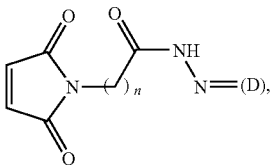

or a protected derivative thereof, where D is the drug, or an analog or a derivative thereof, capable of forming a hydrazone as illustrated herein; and n is an integer such as 1, 2, 3, or 4. In another illustrative aspect of the vitamin receptor binding drug delivery conjugate intermediate described herein, the vitamin, or an analog or a derivative thereof, includes an alkylthiol nucleophile.

In another illustrative embodiment of the vitamin receptor binding drug delivery conjugate intermediate described, herein, the coupling group is a heteroatom, such as nitrogen, oxygen, or sulfur, and the bivalent linker includes one or more heteroatom linkers and one or more spacer linkers covalently connecting the vitamin or analog or derivative thereof to the coupling group. In one illustrative aspect, the vitamin receptor binding drug delivery conjugate intermediate described herein includes a compound having the formula:

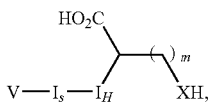

or a protected derivative thereof, where X is oxygen, nitrogen, or sulfur, and m is an integer such as 1, 2, or 3, and where V, $l_s$, and $l_H$ are as defined herein.

In another illustrative aspect, the vitamin receptor binding drug delivery conjugate intermediate described herein includes a compound having the formula:

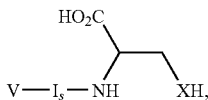

or a protected derivative thereof, where X is nitrogen or sulfur, where V and $l_s$ are as defined herein.

In another illustrative aspect, the vitamin receptor binding drug delivery conjugate intermediate described herein includes a compound having the formula:

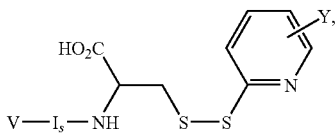

or a protected derivative thereof, where Y is hydrogen or a substituent, illustratively an electron withdrawing substituent, including but not limited to nitro, cyano, halo, alkylsulfonyl, a carboxylic acid derivative, and the like, and where V and $l_s$ are as defined herein.

In another illustrative embodiment of the vitamin receptor binding drug delivery conjugate intermediate described herein, the coupling group is a Michael acceptor, and the bivalent linker includes one or more heteroatom linkers and one or more spacer linkers covalently connecting the vitamin or analog or derivative thereof to the coupling group. In one illustrative aspect of the vitamin receptor binding drug delivery conjugate intermediate described herein, the coupling group and the bivalent linker are taken together to form a compound having the formula:

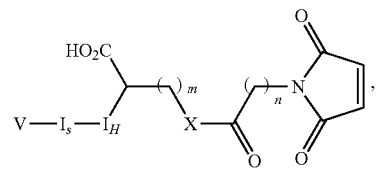

or a protected derivative thereof, where X is oxygen, nitrogen, or sulfur, and m and n are independently selected integers, such as 1, 2, or 3, and where V, $l_s$, and $l_H$ are as defined herein. In another illustrative aspect of the vitamin receptor binding drug delivery conjugate intermediate described herein, the drug, or an analog or a derivative thereof, includes an alkylthiol nucleophile.

In another illustrative aspect of the vitamin receptor binding drug delivery conjugate intermediate described herein, the intermediate includes compounds having the formulae:

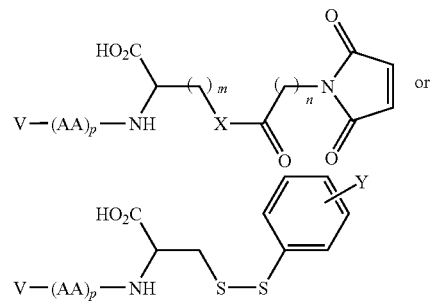

or protected derivatives thereof, where V is the vitamin, or an analog or a derivative thereof, AA is an amino acid, illustratively selected from the naturally occurring amino acids, or stereoisomers thereof, X is nitrogen, oxygen, or sulfur, Y is hydrogen or a substituent, illustratively an electron withdrawing substituent, including but not limited to nitro, cyano, halo, alkylsulfonyl, a carboxylic acid derivative, and the like, n and m are independently selected integers, such as 1, 2, or 3, and p is an integer such as 1, 2, 3, 4, or 5. AA can also be any other amino acid, such as any amino acid having the general formula:

where R is hydrogen, alkyl, acyl, or a suitable nitrogen protecting group, R' and R" are hydrogen or a substiuent, each of which is independently selected in each occurance, and q is an integer such as 1, 2, 3, 4, or 5. Illustratively, R' and/or R" independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above-described formula includes all stereoisomeric variations. For example, the amino acid may be selected from asparagine, aspartic acid, cysteine, glutamic acid, lysine, glutamine, arginine, serine, ornitine, threonine, and the like. In another illustrative aspect of the vitamin receptor binding drug delivery conjugate intermediate described herein, the drug, or an analog or a derivative thereof, includes an alkylthiol nucleophile.

In another embodiment, a process is described for preparing a compound having the formula:

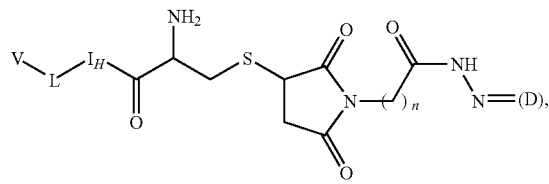

or a protected derivative thereof, where L is a linker comprising $(l_r)_c$, $(l_s)_a$, and $(l_H)_b$, and combinations thereof; and D is a drug, or an analog or a derivative thereof, capable of forming a hydrazone, where $(l_r)_c$, $(l_s)_a$, and $(l_H)_b$, and V are as defined herein, the process comprising the steps of:

(a) reacting a compound having the formula:

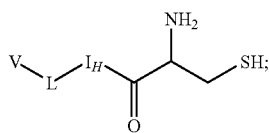

or a protected derivative thereof, with a compound having the formula:

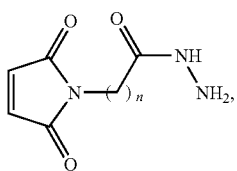

or a protected derivative thereof to form a thiosuccinimide derivative; and (b) forming a hydrazone derivative of the drug, or an analog or a derivative thereof, with the thiosuccinimide derivative.

In another embodiment, a process is described for preparing a compound having the formula:

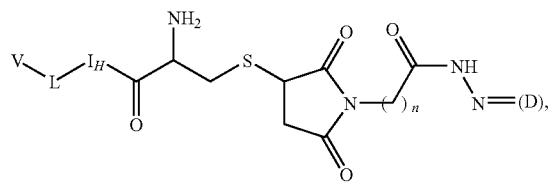

where L is a linker comprising $(l_r)_c$, $(l_s)_a$, and $(l_H)_b$, and combinations thereof; and where D is the drug, or an analog or a derivative thereof, capable of forming a hydrazone, and $(l_r)_c$, $(l_s)_a$, and $(l_H)_b$, and V are as defined herein, the process comprising the step of:

reacting a compound having the formula:

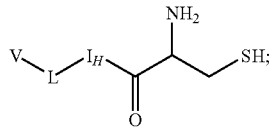

or a protected derivative thereof, with a compound having the formula:

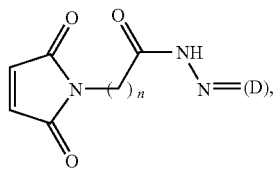

or a protected derivative thereof.

In another embodiment a pharmaceutical composition is described. The pharmaceutical composition comprises a drug delivery conjugate in accordance with the invention, and a pharmaceutically acceptable carrier therefor.

In another embodiment there is described a method for eliminating a population of pathogenic cells in a host animal harboring the population of pathogenic cells wherein the members of the pathogenic cell population have an accessible binding site for a vitamin, or an analog or derivative thereof, and wherein the binding site is uniquely expressed, overexpressed, or preferentially expressed by the pathogenic cells. The method comprises the step of administering to the host a drug delivery conjugate, or a pharmaceutical composition thereof, in accordance with the invention.

DETAILED DESCRIPTION OF THE INVENTION

Figure 1:
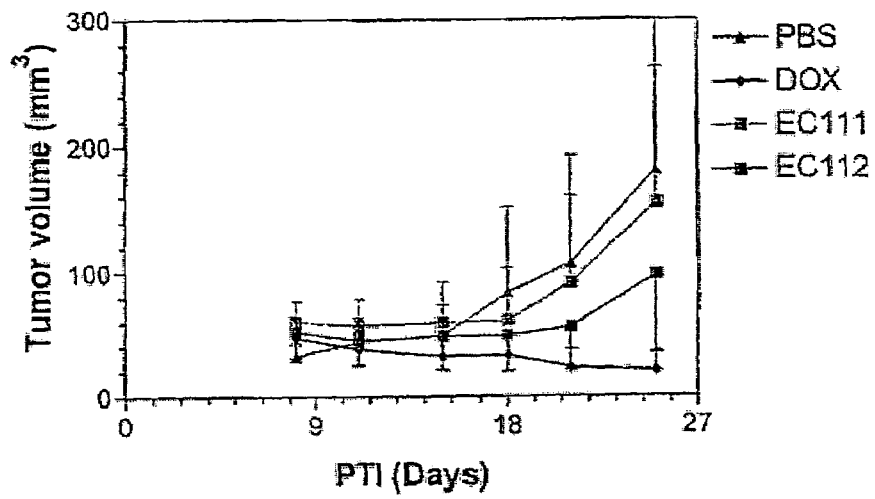
FIG. 1 shows the inhibition of M109 tumor growth by EC112 (Example 9c).

The present invention relates to a vitamin receptor binding drug delivery conjugate comprising a vitamin receptor binding moiety, a bivalent linker (L), and a drug wherein the vitamin receptor binding moiety and the drug are each bound to the bivalent linker (L), optionally through an heteroatom linker. The bivalent linker (L) comprises one or more spacer linkers, heteroatom linkers, and releasable (i.e., cleavable) linkers, and combinations thereof, in any order.

The term "releasable linker" as used herein refers to a linker that includes at least one bond that can be broken under physiological conditions (e.g., a pH-labile, acid-labile, oxidatively-labile, or enzyme-labile bond). It should be appreciated that such physiological conditions resulting in bond breaking include standard chemical hydrolysis reactions that occur, for example, at physiological pH, or as a result of compartmentalization into a cellular organelle such as an endosome having a lower pH than cytosolic pH.

It is understood that a cleavable bond can connect two adjacent atoms within the releasable linker and/or connect other linkers or V and/or D, as described herein, at either or both ends of the releasable linker. In the case where a cleavable bond connects two adjacent atoms within the releasable linker, following breakage of the bond, the releasable linker is broken into two or more fragments. Alternatively, in the case where a cleavable bond is between the releasable linker and another moiety, such as an heteroatom linker, a spacer linker, another releasable linker, the drug, or analog or derivative thereof, or the vitamin, or analog or derivative thereof, following breakage of the bond, the releasable linker is separated from the other moiety.

The lability of the cleavable bond can be adjusted by, for example, substitutional changes at or near the cleavable bond, such as including alpha branching adjacent to a cleavable disulfide bond, increasing the hydrophobicity of substituents on silicon in a moiety having silicon-oxygen bond that may be hydrolyzed, homologating alkoxy groups that form part of a ketal or acetal that may be hydrolyzed, and the like.

In accordance with the invention, the vitamin receptor binding drug delivery conjugates can be used to treat disease states characterized by the presence of a pathogenic cell population in the host wherein the members of the pathogenic cell population have an accessible binding site for a vitamin, or analog or derivative thereof, wherein the binding site is uniquely expressed, overexpressed, or preferentially expressed by the pathogenic cells. The selective elimination of the pathogenic cells is mediated by the binding of the vitamin moiety of the vitamin receptor binding drug delivery conjugate to a vitamin receptor, transporter, or other surface-presented protein that specifically binds the vitamin, or analog or derivative thereof, and which is uniquely expressed, overexpressed, or preferentially expressed by the pathogenic cells. A surface-presented protein uniquely expressed, overexpressed, or preferentially expressed by the pathogenic cells is a receptor not present or present at lower concentrations on non-pathogenic cells providing a means for selective elimination of the pathogenic cells.

For example, surface-expressed vitamin receptors, such as the high-affinity folate receptor, are overexpressed on cancer cells. Epithelial cancers of the ovary, mammary gland, colon, lung, nose, throat, and brain have all been reported to express elevated levels of the folate receptor. In fact, greater than 90% of all human ovarian tumors are known to express large amounts of this receptor. Accordingly, the drug delivery conjugates of the present invention can be used to treat a variety of tumor cell types, as well as other types of pathogenic cells, such as infectious agents, that preferentially express vitamin receptors and, thus, have surface accessible binding sites for vitamins, or vitamin analogs or derivatives.

In addition to the vitamins described herein, it is appreciated that other ligands may be coupled with the drugs and linkers described and contemplated herein to form ligand-linker-drug conjugates capable of facilitating delivery of the drug to a desired target. These other ligands, in addition to the vitamins and their analogs and derivatives described, may be used to form drug delivery conjugates capable of binding to target cells. In general, any ligand of a cell surface receptor may be advantageously used as a targeting ligand to which a linker-drug conjugate can be prepared. Illustrative other ligands contemplated herein include peptide ligands identified from library screens, tumor cell-specific peptides, tumor cell-specific aptamers, tumor cell-specific carbohydrates, tumor cell-specific monoclonal or polyclonal antibodies, Fab or scFv (i.e., a single chain variable region) fragments of antibodies such as, for example, an Fab fragment of an antibody directed to EphA2 or other proteins specifically expressed or uniquely accessible on metastatic cancer cells, small organic molecules derived from combinatorial libraries, growth factors, such as EGF, FGF, insulin, and insulin-like growth factors, and homologous polypeptides, somatostatin and its analogs, transferrin, lipoprotein complexes, bile salts, selecting, steroid hormones, Arg-Gly-Asp containing peptides, retinoids, various Galectins, δ-opioid receptor ligands, cholecystokinin A receptor ligands, ligands specific for angiotensin AT1 or AT2 receptors, peroxisome proliferator-activated receptor λ ligands, β-lactam antibiotics such as penicillin, small organic molecules including antimicrobial drugs, and other molecules that bind specifically to a receptor preferentially expressed on the surface of tumor cells or on an infectious organism, antimicrobial and other drugs designed to fit into the binding pocket of a particular receptor based on the crystal structure of the receptor or other cell surface protein, ligands of tumor antigens or other molecules preferentially expressed on the surface of tumor cells, or fragments of any of these molecules. An example of a tumor-specific antigen that could function as a binding site for ligand-immunogen conjugates include extracellular epitopes of a member of the Ephrin family of proteins, such as EphA2. EphA2 expression is restricted to cell-cell junctions in normal cells, but EpbA2 is distributed over the entire cell surface in metastatic tumor cells. Thus, EphA2 on metastatic cells would be accessible for binding to, for example, an Fab fragment of an antibody conjugated to an immunogen, whereas the protein would not be accessible for binding to the Fab fragment on normal cells, resulting in a ligand-immunogen conjugate specific for metastatic cancer cells.

The invention further contemplates the use of combinations of ligand-linker-drug conjugates to maximize targeting of the pathogenic cells for elimination.

Illustrative drug delivery conjugates are as follows:

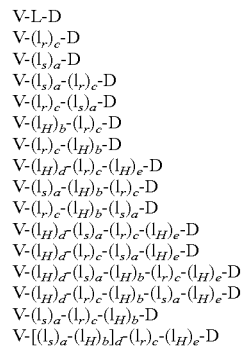

wherein a, b, c, d, and e are each independently 0, 1, 2, 3, or 4, $(l_s)$ is a spacer linker, $(l_H)$ is an heteroatom linker, and $(l_r)$ is a releasable linker, V is a vitamin, or analog or derivative thereof, and D is a drug, or analog or derivative thereof, and where the bivalent L encompasses a one or a variety of $(l_s)$, $(l_H)$, and $(l_r)$, in any order and in any combination. It is understood that the foregoing examples of the bivalent linker L are intended to illustrate, and not limit, the wide variety of assemblies of $l_H$, $l_s$, and $l_r$ that the bivalent linker encompasses.

In one embodiment of the drug delivery conjugate V-L-D, wherein V is the vitamin folic acid; L is not ethylenediamine, according to the formula:

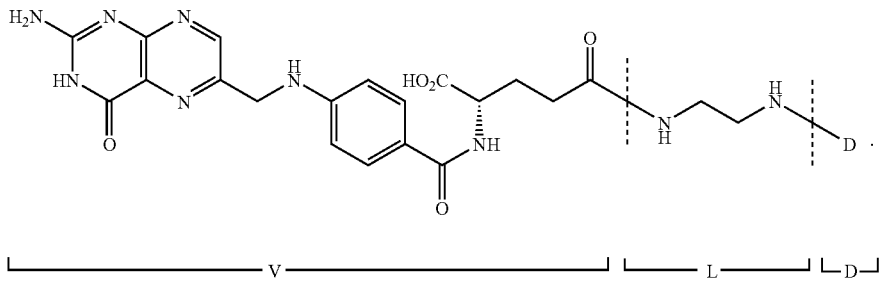

In another embodiment of the drug delivery conjugate V-L-D, wherein V is the vitamin folic acid, and D is the drug mitomycin C; L is not L-Cys-(S-thioethyl), according to the formula:

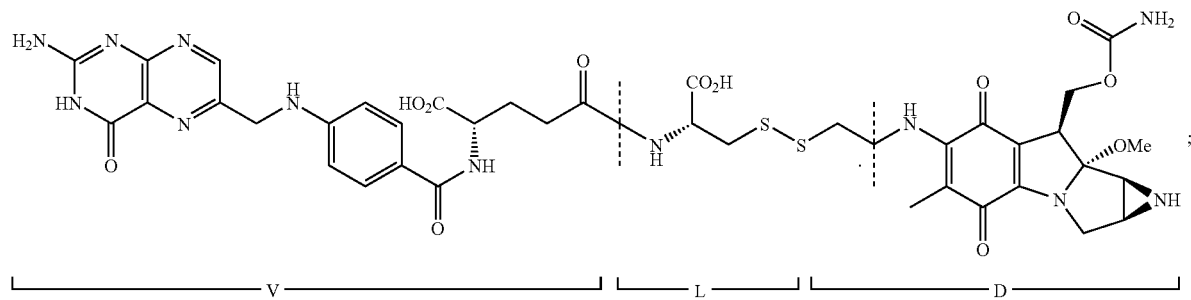

L is not L-Asp-L-Arg-L-Asp-L-Cys-(S-thioethyl), according to the formula:

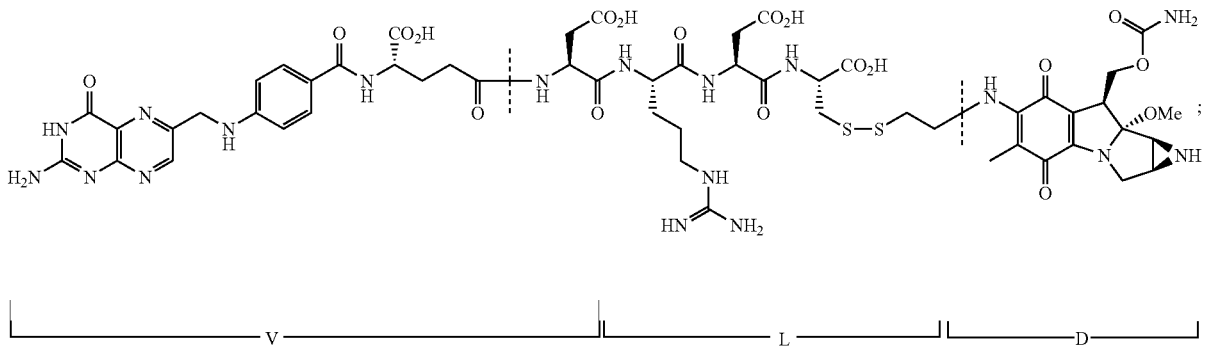

and L is not L-Arg-L-Cys-(S-thioethyl)-L-Ala-L-Gly-OH, according to the formula:

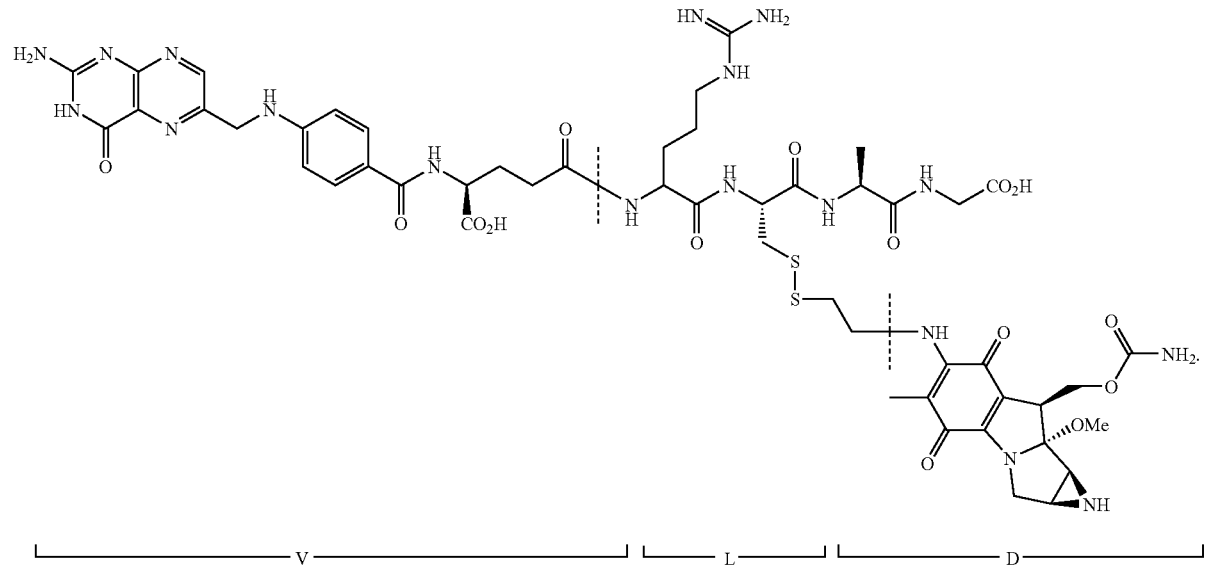

Also contemplated in accordance with the present invention are drug delivery conjugates where the vitamin, or analog or derivative thereof, is attached to a releasable linker which is attached to the drug through a spacer linker. Furthermore, both the drug and the vitamin, or analog or derivative thereof, can each be attached to spacer linkers, where the spacer linkers are attached to each other through a releasable linker. In addition, both the drug and the vitamin, or analog or derivative thereof, can each be attached to releasable linkers, where the releasable linkers are attached to each other through a spacer linker. The heteroatom linker may be placed between any two linkers, or between any linker and the vitamin, or analog or derivative, or between any linker and the drug, or analog or derivative. All other possible permutations and combinations are also contemplated.

In one embodiment, the present invention provides a vitamin receptor binding drug delivery conjugate. The drug delivery conjugate consists of a vitamin receptor binding moiety, bivalent linker (L), and a drug. The vitamin receptor binding moiety is a vitamin, or an analog or a derivative thereof, capable of binding to vitamin receptors, and the drug includes analogs or derivatives thereof exhibiting drug activity. The vitamin, or the analog or the derivative thereof, is covalently attached to the bivalent linker (L), and the drug, or the analog or the derivative thereof, is also covalently attached to the bivalent linker (L). The bivalent linker (L) comprises one or more spacer linkers, releasable linkers, and heteroatom linkers, and combinations thereof, in any order. For example, the heteroatom linker can be nitrogen, and the releasable linker and the heteroatom linker can be taken together to form a divalent radical comprising alkyleneaziridin-1-yl, alkylenecarbonylaziridin-1-yl, carbonylalkylaziridin-1-yl, alkylenesulfoxylaziridin-1-yl, sulfoxylalkylaziridin-1-yl, sulfonylalkylaziridin-1-yl, or alkylenesulfonylaziridin-1-yl, wherein each of the releasable linkers is optionally substituted with a substituent $X^2$, as defined below. Alternatively, the heteroatom linkers can be nitrogen, oxygen, sulfur, and the formulae —(NHR$^1$NHR$^2$)—, —SO—, —(SO$_2$)—, and —N(R$^3$)O—, wherein R$^1$, R$^2$, and R$^3$ are each independently selected from hydrogen, alkyl, aryl, arylalkyl, substituted aryl, substituted arylalkyl, heteroaryl, substituted heteroaryl, and alkoxyalkyl. In another embodiment, the heteroatom linker can be oxygen, the spacer linker can be 1-alkylenesuccinimid-3-yl, optionally substituted with a substituent $X^1$, as defined below, and the releasable linkers can be methylene, 1-alkoxyalkylene, 1-alkoxycycloalkylene, 1-alkoxyalkylenecarbonyl, 1-alkoxycycloalkylenecarbonyl, wherein each of the releasable linkers is optionally substituted with a substituent $X^2$, as defined below, and wherein the spacer linker and the releasable linker are each bonded to the heteroatom linker to form a succinimid-1-ylalkyl acetal or ketal.

The spacer linkers can be carbonyl, thionocarbonyl, alkylene, cycloalkylene, alkylenecycloalkyl, alkylenecarbonyl, cycloalkylenecarbonyl, carbonylalkylcarbonyl, 1-alkylenesuccinimid-3-yl, 1-(carbonylalkyl)succinimid-3-yl, alkylenesulfoxyl, sulfonylalkyl, alkylenesulfoxylalkyl, alkylenesulfonylalkyl, carbonyltetrahydro-2H-pyranyl, carbonyltetrahydrofuranyl, 1-(carbonyltetrahydro-2H-pyranyl)succinimid-3-yl, and 1-(carbonyltetrahydrofuranyl)succinimid-3-yl, wherein each of the spacer linkers is optionally substituted with a substituent $X^1$, as defined below. In this embodiment, the heteroatom linker can be nitrogen, and the spacer linkers can be alkylenecarbonyl, cycloalkylenecarbonyl, carbonylalkylcarbonyl, 1-(carbonylalkyl)succinimid-3-yl, wherein each of the spacer linkers is optionally substituted with a substituent $X^1$, as defined below, and the spacer linker is bonded to the nitrogen to form an amide. Alternatively, the heteroatom linker can be sulfur, and the spacer linkers can be alkylene and cycloalkylene, wherein each of the spacer linkers is optionally substituted with carboxy, and the spacer linker is bonded to the sulfur to form a thiol. In another embodiment, the heteroatom linker can be sulfur, and the spacer linkers can be 1-alkylenesuccinimid-3-yl and 1-(carbonylalkyl)succinimid-3-yl, and the spacer linker is bonded to the sulfur to form a succinimid-3-ylthiol.

In an alternative to the above-described embodiments, the heteroatom linker can be nitrogen, and the releasable linker and the heteroatom linker can be taken together to form a divalent radical comprising alkyleneaziridin-1-yl, carbonylalkylazindin-1-yl, sulfoxylalkylaziridin-1-yl, or sulfonylalkylaziridin-1-yl, wherein each of the releasable linkers is optionally substituted with a substituent $X^2$, as defined below. In this alternative embodiment, the spacer linkers can be carbonyl, thionocarbonyl, alkylenecarbonyl, cycloalkylenecarbonyl, carbonylalkylcarbonyl, 1-(carbonylalkyl)succinimid-3-yl, wherein each of the spacer linkers is optionally substituted with a substituent $X^1$, as defined below, and wherein the spacer linker is bonded to the releasable linker to form an aziridine amide.

The substituents $X^1$ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl; $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides. In this embodiment the heteroatom linker can be nitrogen, and the substituent $X^1$ and the heteroatom linker can be taken together with the spacer linker to which they are bound to form an heterocycle.

The releasable linkers can be methylene, 1-alkoxyalkylene, 1-alkoxycycloalkylene, 1-alkoxyalkylenecarbonyl, 1-alkoxycycloalkylenecarbonyl, carbonylarylcarbonyl, carbonyl(carboxyaryl)carbonyl, carbonyl(biscarboxyaryl)carbonyl, haloalkylenecarbonyl, alkylene(dialkylsilyl), alkylene(alkylarylsilyl), alkylene(diarylsilyl), (dialkylsilyl)aryl, (alkylarylsilyl)aryl, (diarylsilyl)aryl, oxycarbonyloxy, oxycarbonyloxyalkyl, sulfonyloxy, oxysulfonylalkyl, iminoalkylidenyl, carbonylalkylideniminyl, iminocycloalkylidenyl, carbonylcycloalkylideniminyl, alkylenethio, alkylenearylthio, and carbonylalkylthio, wherein each of the releasable linkers is optionally substituted with a substituent $X^2$, as defined below.

In the preceding embodiment, the heteroatom linker can be oxygen, and the releasable linkers can be methylene, 1-alkoxyalkylene, 1-alkoxycycloalkylene, 1-alkoxyalkylenecarbonyl, and 1-alkoxycycloalkylenecarbonyl, wherein each of the releasable linkers is optionally substituted with a substituent $X^2$, as defined below, and the releasable linker is bonded to the oxygen to form an acetal or ketal. Alternatively, the heteroatom linker can be oxygen, and the releasable linker can be methylene, wherein the methylene is substituted with an optionally-substituted aryl, and the releasable linker is bonded to the oxygen to form an acetal or ketal. Further, the heteroatom linker can be oxygen, and the releasable linker can be sulfonylalkyl, and the releasable linker is bonded to the oxygen to form an alkylsulfonate.

In another embodiment of the above releasable linker embodiment, the heteroatom linker can be nitrogen, and the releasable linkers can be iminoalkylidenyl, carbonylalkylideniminyl, iminocycloalkylidenyl, and carbonylcycloalkylideniminyl, wherein each of the releasable linkers is optionally substituted with a substituent $X^2$, as defined below, and the releasable linker is bonded to the nitrogen to form an hydrazone. In an alternate configuration, the hydrazone may be acylated with a carboxylic acid derivative, an orthoformate derivative, or a carbamoyl derivative to form various acylhydrazone releasable linkers.

Alternatively, the heteroatom linker can be oxygen, and the releasable linkers can be alkylene(dialkylsilyl), alkylene(alkylarylsilyl), alkylene(diarylsilyl), (dialkylsilyl)aryl, (alkylarylsilyl)aryl, and (diarylsilyl)aryl, wherein each of the releasable linkers is optionally substituted with a substituent $X^2$, as defined below, and the releasable linker is bonded to the oxygen to form a silanol.

In the above releasable linker embodiment, the drug can include a nitrogen atom, the heteroatom linker can be nitrogen, and the releasable linkers can be carbonylarylcarbonyl, carbonyl(carboxyaryl)carbonyl, carbonyl(biscarboxyaryl)carbonyl, and the releasable linker can be bonded to the heteroatom nitrogen to form an amide, and also bonded to the drug nitrogen to form an amide.

In the above releasable linker embodiment, the drug can include an oxygen atom, the heteroatom linker can be nitrogen, and the releasable linkers can be carbonylarylcarbonyl, carbonyl(carboxyaryl)carbonyl, carbonyl(biscarboxyaryl)carbonyl, and the releasable linker can be bonded to the heteroatom linker nitrogen to form an amide, and also bonded to the drug oxygen to form an ester.

The substituents $X^2$ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides. In this embodiment the heteroatom linker can be nitrogen, and the substituent $X^2$ and the heteroatom linker can be taken together with the releasable linker to which they are bound to form an heterocycle.

The heterocycles can be pyrrolidines, piperidines, oxazolidines, isoxazolidines, thiazolidines, isothiazolidines, pyrrolidinones, piperidinones, oxazolidinones, isoxazolidinones, thiazolidinones, isothiazolidinones, and succinimides.

The drug can be a mitomycin, a mitomycin derivative, or a mitomycin analog, and, in this embodiment, the releasable linkers can be carbonylalkylthio, carbonyltetrahydro-2H-pyranyl, carbonyltetrahydrofuranyl, 1-(carbonyltetrahydro-2H-pyranyl)succinimid-3-yl, and 1-(carbonyltetrahydrofuranyl)succinimid-3-yl, wherein each of the releasable linkers is optionally substituted with a substituent $X^2$, and wherein the aziridine of the mitomycin is bonded to the releasable linker to form an acylaziridine.

The drug can include a nitrogen atom, and the releasable linker can be haloalkylenecarbonyl, optionally substituted with a substituent $X^2$, and the releasable linker is bonded to the drug nitrogen to form an amide.

The drug can include an oxygen atom, and the releasable linker can be haloalkylenecarbonyl, optionally substituted with a substituent $X^2$, and the releasable linker is bonded to the drug oxygen to form an ester.

The drug can include a double-bonded nitrogen atom, and in this embodiment, the releasable linkers can be alkylenecarbonylamino and 1-(alkylenecarbonylamino)succinimid-3-yl, and the releasable linker can be bonded to the drug nitrogen to form an hydrazone.

The drug can include a sulfur atom, and in this embodiment, the releasable linkers can be alkylenethio and carbonylalkylthio, and the releasable linker can be bonded to the drug sulfur to form a disulfide.

The vitamin can be folate which includes a nitrogen, and in this embodiment, the spacer linkers can be alkylenecarbonyl, cycloalkylenecarbonyl, carbonylalkylcarbonyl, 1-alkylenesuccinimid-3-yl, 1-(carbonylalkyl)succinimid-3-yl, wherein each of the spacer linkers is optionally substituted with a substituent $X^1$, and the spacer linker is bonded to the folate nitrogen to form an imide or an alkylamide. In this embodiment, the substituents $X^1$ can be alkyl, hydroxyalkyl, amino, aminoalkyl, alkylaminoalkyl, dialkylaminoalkyl, sulfhydrylalkyl, alkylthioalkyl, aryl, substituted aryl, arylalkyl, substituted arylalkyl, carboxy, carboxyalkyl, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides.

The term "alkyl" as used herein refers to a monovalent linear chain of carbon atoms that may be optionally branched, such as methyl, ethyl, propyl, 3-methylpentyl, and the like.

The term "cycloalkyl" as used herein refers to a monovalent chain of carbon atoms, a portion of which forms a ring, such as cyclopropyl, cyclohexyl, 3-ethylcyclopentyl, and the like.

The term "alkylene" as used herein refers to a bivalent linear chain of carbon atoms that may be optionally branched, such as methylene, ethylene, propylene, 3-methylpentylene, and the like.

The term "cycloalkylene" as used herein refers to a bivalent chain of carbon atoms, a portion of which forms a ring, such as cycloprop-1,1-diyl, cycloprop-1,2-diyl, cyclohex-1,4-diyl, 3-ethylcyclopent-1,2-diyl, 1-methylenecyclohex-4-yl, and the like.

The term "heterocycle" as used herein refers to a monovalent chain of carbon and heteroatoms, wherein the heteroatoms are selected from nitrogen, oxygen, and sulfur, a portion of which, including at least one heteroatom, form a ring, such as aziridine, pyrrolidine, oxazolidine, 3-methoxypyrrolidine, 3-methylpiperazine, and the like.

The term "alkoxy" as used herein refers to alkyl as defined herein combined with a terminal oxygen, such as methoxy, ethoxy, propoxy, 3-methylpentoxy, and the like.

The term "halo" or "halogen" refers to fluoro, chloro, bromo, and iodo.

The term "aryl" as used herein refers to an aromatic mono or polycyclic ring of carbon atoms, such as phenyl, naphthyl, and the like.

The term "heteroaryl" as used herein refers to an aromatic mono or polycyclic ring of carbon atoms and at least one heteroatom selected from nitrogen, oxygen, and sulfur, such as pyridinyl, pyrimidinyl, indolyl, benzoxazolyl, and the like.

The term "substituted aryl" or "substituted heteroaryl" as used herein refers to aryl or heteroaryl substituted with one or more substituents selected, such as halo, hydroxy, amino, alkyl or dialkylamino, alkoxy, alkylsulfonyl, cyano, nitro, and the like.

The term "iminoalkylidenyl" as used herein refers to a divalent radical containing alkylene as defined herein and a nitrogen atom, where the terminal carbon of the alkylene is double-bonded to the nitrogen atom, such as the formulae —(CH)=N—, —(CH$_2$)$_2$(CH)=N—, —CH$_2$C(Me)=N—, and the like.

The term "amino acid" as used herein refers generally to aminoalkylcarboxylate, where the alkyl radical is optionally substituted with alkyl, hydroxy alkyl, sulfhydrylalkyl, aminoalkyl, carboxyalkyl, and the like, including groups corresponding to the naturally occurring amino acids, such as serine, cysteine, methionine, aspartic acid, glutamic acid, and the like.

The term "arylalkyl" refers to aryl as defined herein substituted with an alkylene group, as defined herein, such as benzyl, phenethyl, α-methylbenzyl, and the like.

It should be understood that the above-described terms can be combined to generate chemically-relevant groups, such as "alkoxyalkyl" referring to methyloxymethyl, ethyloxyethyl, and the like, and "haloalkoxyalkyl" referring to trifluoromethyloxyethyl, 1,2-difluoro-2-chloroeth-1-yloxypropyl, and the like.

The term "amino acid derivative" as used herein refers generally to aminoalkylcarboxylate, where the amino radical or the carboxylate radical are each optionally substituted with alkyl, carboxylalkyl, alkylamino, and the like, or optionally protected; and the intervening divalent alkyl fragment is optionally substituted with alkyl, hydroxy alkyl, sulfhydrylalkyl, aminoalkyl, carboxyalkyl, and the like, including groups corresponding to the side chains found in naturally occurring amino acids, such as are found in serine, cysteine, methionine, aspartic acid, glutamic acid, and the like.

The term "peptide" as used herein refers generally to a series of amino acids and amino acid analogs and derivatives covalently linked one to the other by amide bonds.

The releasable linker includes at least one bond that can be broken or cleaved under physiological conditions (e.g., a pH-labile, acid-labile, oxidatively-labile, or enzyme-labile bond). The cleavable bond or bonds may be present in the interior of a cleavable linker and/or at one or both ends of a cleavable linker. It is appreciated that the lability of the cleavable bond may be adjusted by including functional groups or fragments within the bivalent linker L that are able to assist or facilitate such bond breakage, also termed anchimeric assistance. In addition, it is appreciated that additional functional groups or fragments may be included within the bivalent linker L that are able to assist or facilitate additional fragmentation of the vitamin receptor binding drug conjugates after bond breaking of the releasable linker.

Illustrative mechanisms for bond cleavage of the releasable linker include oxonium-assisted cleavage as follows:

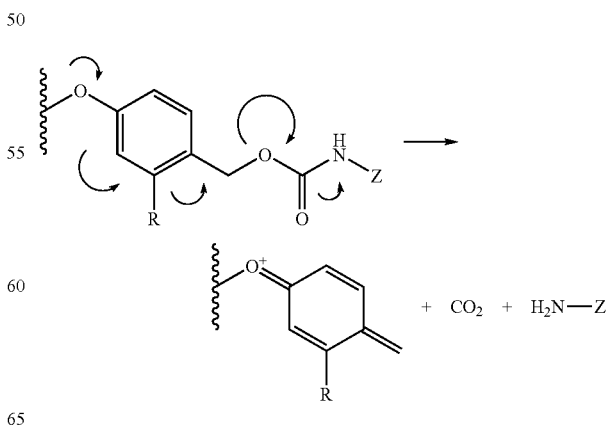

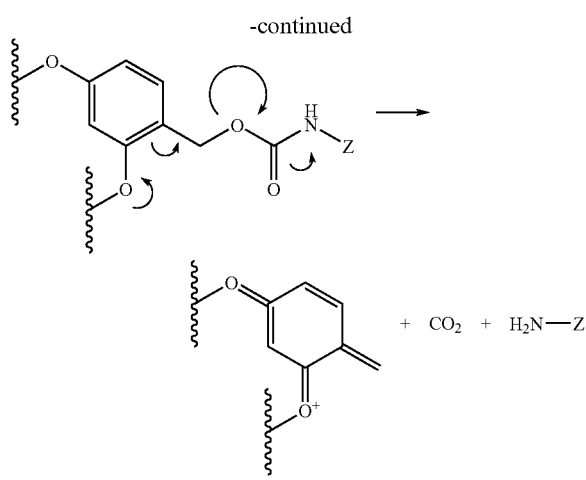

where Z is the vitamin, or analog or derivative thereof, or the drug, or analog or derivative thereof, or each is a vitamin or drug moiety in conjunction with other portions of the bivalent linker, such as a drug or vitamin moiety including one or more spacer linkers, heteroatom linkers, and/or other releasable linkers. In this embodiment, acid-catalyzed elimination of the carbamate leads to the release of $CO_2$ and the nitrogen-containing moiety attached to Z, and the formation of a benzyl cation, which may be trapped by water, or any other Lewis base.

Another illustrative mechanism for cleavage of bonds connected to or contained within releasable linkers, which may form part of the bivalent linker L, include the following beta-elimination and vinylogous beta-elimination mechanisms:

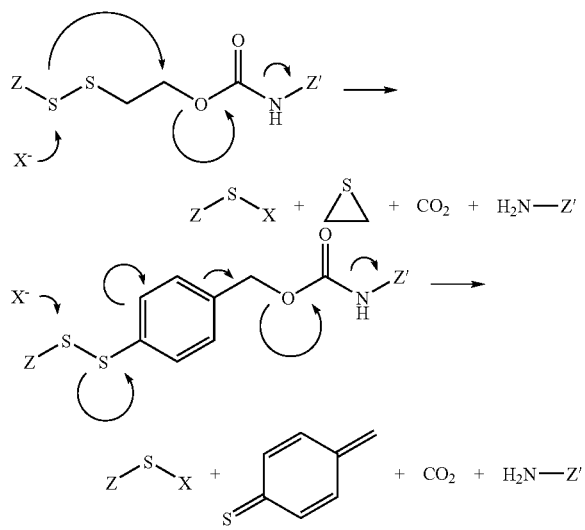

where X is a nucleophile, GSH, glutathione, or bioreducing agent, and the like, and either of Z or Z' is the vitamin, or analog or derivative thereof, or the drug, or analog or derivative thereof, or a vitamin or drug moiety in conjunction with other portions of the bivalent linker. It is appreciated that the bond cleavage may also occur by acid catalyzed elimination of the carbamate moiety, which may be anchimerically assisted by the stabilization provided by either the aryl group of the beta sulfur or disulfide illustrated in the above examples. In those variations of this embodiment, the releasable linker is the carbamate moiety.

Another illustrative mechanism involves an arrangement of the releasable, spacer, and heteroatom linkers in such a way that subsequent to the cleavage of a bond in the bivalent linker, released functional groups chemically assist the breakage or cleavage of additional bonds, also termed anchimeric assisted cleavage or breakage. An illustrative embodiment of such a bivalent linker or portion thereof includes compounds having the formula:

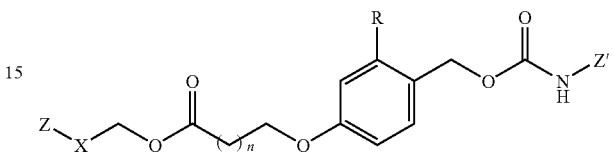

where X is an heteroatom, such as nitrogen, oxygen, or sulfur, n is an integer selected from 0, 1, 2, and 3, R is hydrogen, or a substituent, including a substituent capable of stabilizing a positive charge inductively or by resonance on the aryl ring, such as alkoxy, and the like, and either of Z or Z' is the vitamin, or analog or derivative thereof, or the drug, or analog or derivative thereof, or a vitamin or drug moiety in conjunction with other portions of the bivalent linker. It is appreciated that other substituents may be present on the aryl ring, the benzyl carbon, the carbamate nitrogen, the alkanoic acid, or the methylene bridge, including but not limited to hydroxy, alkyl, alkoxy, alkylthio, halo, and the like. Assisted cleavage may include mechanisms involving benzylium intermediates, benzyne intermediates, lactone cyclization, oxonium intermediates, beta-elimination, and the like. It is further appreciated that, in addition to fragmentation subsequent to cleavage of the releasable linker, the initial cleavage of the releasable linker may be facilitated by an anchimerically assisted mechanism.

In this embodiment, the hydroxyalkanoic acid, which may cyclize, facilitates cleavage of the methylene bridge, by for example an oxonium ion, and facilitates bond cleavage or subsequent fragmentation after bond cleavage of the releasable linker. Alternatively, acid catalyzed oxonium ion-assisted cleavage of the methylene bridge may begin a cascade of fragmentation of this illustrative bivalent linker, or fragment thereof. Alternatively, acid-catalyzed hydrolysis of the carbamate may facilitate the beta elimination of the hydroxyalkanoic acid, which may cyclize, and facilitate cleavage of methylene bridge, by for example an oxonium ion. It is appreciated that other chemical mechanisms of bond breakage or cleavage under the metabolic, physiological, or cellular conditions described herein may initiate such a cascade of fragmentation. It is appreciated that other chemical mechanisms of bond breakage or cleavage under the metabolic, physiological, or cellular conditions described herein may initiate such a cascade of fragmentation.

The drug delivery conjugates described herein can be prepared by art-recognized synthetic methods. The synthetic methods are chosen depending upon the selection of the heteroatom linkers, and the functional groups present on the spacer linkers and the releasable linkers. In general, the relevant bond forming reactions are described in Richard C. Larock, "Comprehensive Organic Transformations, a guide to functional group preparations," VCH Publishers, Inc. New York (1989), and in Theodora E. Greene & Peter G. M. Wuts, "Protective Groups ion Organic Synthesis," 2d edition, John Wiley & Sons, Inc. New York (1991), the disclosures of which are incorporated herein by reference.

General Amide and Ester Formation.

For example, where the heteroatom linker is a nitrogen atom, and the terminal functional group present on the spacer linker or the releasable linker is a carbonyl group, the required amide group can be obtained by coupling reactions or acylation reactions of the corresponding carboxylic acid or derivative, where L is a suitably-selected leaving group such as halo, triflate, pentafluorophenoxy, trimethylsilyloxy, succinimide-N-oxy, and the like, and an amine, as illustrated in Scheme 1.

Scheme 1

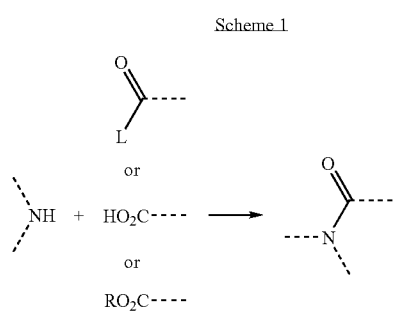

Coupling reagents include DCC, EDC, RRDQ, CGI, HBTU, TBTU, HOBT/DCC, HOBT/EDC, BOP-Cl, PyBOP, PyBroP, and the like. Alternatively, the parent acid can be converted into an activated carbonyl derivative, such as an acid chloride, a N-hydroxysuccinimidyl ester, a pentafluorophenyl ester, and the like. The amide-forming reaction can also be conducted in the presence of a base, such as triethylamine, diisopropylethylamine, N,N-dimethyl-4-aminopyridine, and the like. Suitable solvents for forming amides described herein include $CH_2Cl_2$, $CHCl_3$, THF, DMF, DMSO, acetonitrile, EtOAc, and the like. Illustratively, the amides can be prepared at temperatures in the range from about −15° C. to about 80° C., or from about 0° C. to about 45° C. Amides can be formed from, for example, nitrogen-containing aziridine rings, carbohydrates, and α-halogenated carboxylic acids. Illustrative carboxylic acid derivatives useful for forming amides include compounds having the formulae:

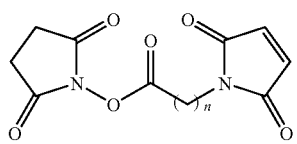

and the like, where n is an integer such as 1, 2, 3, or 4.

Similarly, where the heteroatom linker is an oxygen atom and the terminal functional group present on the spacer linker or the releasable linker is a carbonyl group, the required ester group can be obtained by coupling reactions of the corresponding carboxylic acid or derivative, and an alcohol.

Coupling reagents include DCC, EDC, CDI, BOP, PyBOP, isopropenyl chloroformate, EEDQ, DEAD, $PPh_3$, and the like. Solvents include $CH_2Cl_2$, $CHCl_3$, TBF, DMF, DMSO, acetonitrile, EtOAc, and the like. Bases include triethylamine, diisopropyl-ethylamine, and N,N-dimethyl-4-aminopyridine. Alternatively, the parent acid can be converted into an activated carbonyl derivative, such as an acid chloride, a N-hydroxysuccinimidyl ester, a pentafluorophenyl ester, and the like.

General Ketal and Acetal Formation.

Furthermore, where the heteroatom linker is an oxygen atom, and the functional group present on the spacer linker or the releasable linker is 1-alkoxyalkyl, the required acetal or ketal group can be formed by ketal and acetal forming reactions of the corresponding alcohol and an enol ether, as illustrated in Scheme 2.

Scheme 2

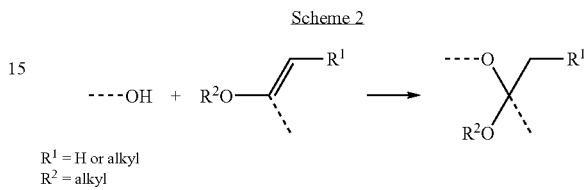

$R^1$ = H or alkyl
$R^2$ = alkyl

Solvents include alcohols, $CH_2Cl_2$, $CHCl_3$, THF, diethylether, DMF, DMSO, acetonitrile, EtOAc, and the like. The formation of such acetals and ketals can be accomplished with an acid catalyst. Where the heteroatom linker comprises two oxygen atoms, and the releasable linker is methylene, optionally substituted with a group $X^2$ as described herein, the required symmetrical acetal or ketal group can be illustratively formed by acetal and ketal forming -reactions from the corresponding alcohols and an aldehyde or ketone, as illustrated in Scheme 3.

Scheme 3

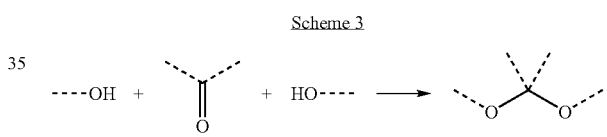

Alternatively, where the methylene is substituted with an optionally-substituted aryl group, the required acetal or ketal may be prepared stepwise, where L is a suitably selected leaving group such as halo, trifluoroacetoxy, triflate, and the like, as illustrated in Scheme 4. The process illustrated in Scheme 4 is a conventional preparation, and generally follows the procedure reviewed by R. R. Schmidt et al., *Chem. Rev.*, 2000, 100, 4423-42, the disclosure of which is incorporated herein by reference.

Scheme 4

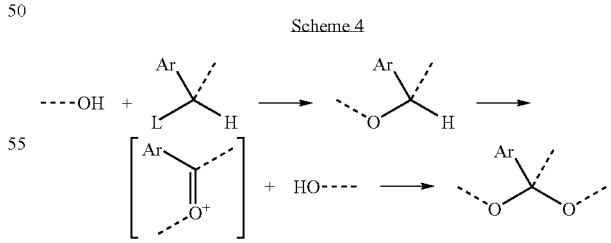

The resulting arylalkyl ether is treated with an oxidizing agent, such as DDQ, and the like, to generate an intermediate oxonium ion that is subsequently treated with another alcohol to generate the acetal or ketal.

General Succinimide Formation.

Furthermore, where the heteroatom linker is, for example, a nitrogen, oxygen, or sulfur atom, and the functional group present on the spacer linker or the releasable linker is a succinimide derivative, the resulting carbon-heteroatom bond can be formed by a Michael addition of the corresponding amine, alcohol, or thiol, and a maleimide derivative, where X is the heteroatom linker, as illustrated in Scheme 5.

Scheme 5

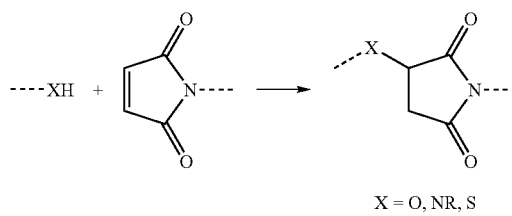

X = O, NR, S

Solvents for performing the Michael addition include THF, EtOAc, $CH_2Cl_2$, DMF, DMSO, $H_2O$ and the like. The formation of such Michael adducts can be accomplished with the addition of equimolar amounts of bases, such as triethylamine, Hunig's base or by adjusting the pH of water solutions to 6.0-7.4. It is appreciated that when the heteroatom linker is an oxygen or nitrogen atom, reaction conditions may be adjusted to facilitate the Michael addition, such as, for example, by using higher reaction temperatures, adding catalysts, using more polar solvents, such as DMF, DMSO, and the like, and activating the maleimide with silylating reagents.

General Silyloxy Formation.

Furthermore, where the heteroatom linker is an oxygen atom, and the functional group present on the spacer linker or the releasable linker is a silyl derivative, the required silyloxy group may be formed by reacting the corresponding silyl derivative, and an alcohol, where L is a suitably selected leaving group such as halo, trifluoroacetoxy, triflate, and the like, as illustrated in Scheme 6.

Scheme 6

Silyl derivatives include properly functionalized silyl derivatives such as vinylsulfonoalkyl diaryl, or diaryl, or alkyl aryl silyl chloride. Instead of a vinylsulfonoalkyl group, a β-chloroethylsulfonoalkyl precursor may be used. Any aprotic and anhydrous solvent and any nitrogen-containing base may serve as a reaction medium. The temperature range employed in this transformation may vary between −78° C. and 80° C.

General Hydrazone Formation.

Furthermore, where the heteroatom linker is a nitrogen atom, and the functional group present on the spacer linker or the releasable linker is an iminyl derivative, the required hydrazone group can be formed by reacting the corresponding aldehyde or ketone, and a hydrazine or acylhydrazine derivative, as illustrated in Scheme 7, equations (1) and (2) respectively.

Scheme 7

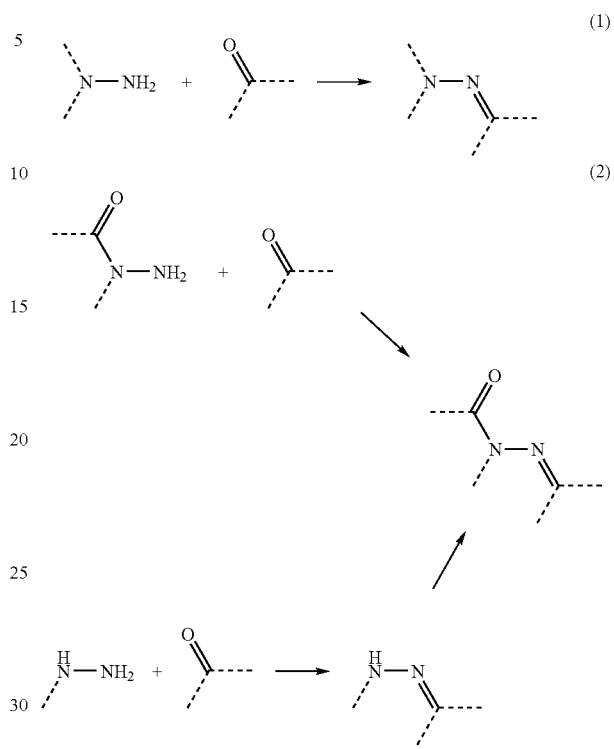

Solvents that can be used include THF, EtOAc, $CH_2Cl_2$, $CHCl_3$, $CCl_4$, DMF, DMSO, MeOH and the like. The temperature range employed in this transformation may vary between 0° C. and 80° C. Any acidic catalyst such as a mineral acid, $H_3CCOOH$, $F_3CCOOH$, p-TsOH.$H_2O$, pyridinium p-toluene sulfonate, and the like can be used. In the case of the acylhydrazone in equation (2), the acylhydrazone may be prepared by initially acylating hydrazine with a suitable carboxylic acid or derivative, as generally described above in Scheme 1, and subsequently reacting the acylhydrazide with the corresponding aldehyde or ketone to form the acylhydrazone. Alternatively, the hydrazone functionality may be initially formed by reacting hydrazine with the corresponding aldehyde or ketone. The resulting hydrazone may subsequently be acylated with a suitable carboxylic acid or derivative, as generally described above in Scheme 1.

General Disulfide Formation.

Furthermore, where the heteroatom linker is a sulfur atom, and the functional group present on the releasable linker is an alkylenethiol derivative, the required disulfide group can be formed by reacting the corresponding alkyl or aryl sulfonylthioalkyl derivative, or the corresponding heteroaryldithioalkyl derivative such as a pyridin-2-yldithioalkyl derivative, and the like, with an alkylenethiol derivative, as illustrated in Scheme 8.

Scheme 8

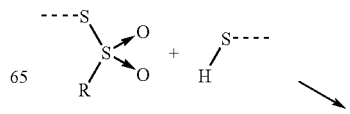

-continued

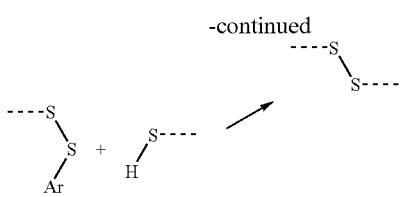

Solvents that can be used are THF, EtOAc, CH$_2$Cl$_2$, CHCl$_3$, CCl$_4$, DMF, DMSO, and the like. The temperature range employed in this transformation may vary between 0° C. and 80° C. The required alkyl or aryl sulfonylthioalkyl derivative may be prepared using art-recognized protocols, and also according to the method of Ranasinghe and Fuchs, *Synth. Commun.* 18(3), 227-32 (1988), the disclosure of which is incorporated herein by reference. Other methods of preparing unsymmetrical dialkyl disulfides are based on a transthiolation of unsymmetrical heteroaryl-alkyl disulfides, such as 2-thiopyridinyl, 3-nitro-2-thiopyridinyl, and like disulfides, with alkyl thiol, as described in WO 88/01622, European Patent Application No. 0116208A1, and U.S. Pat. No. 4,691,024, the disclosures of which are incorporated herein by reference.

General Carbonate Formation.

Furthermore, where the heteroatom linker is an oxygen atom, and the functional group present on the spacer linker or the releasable linker is an alkoxycarbonyl derivative, the required carbonate group can be formed by reacting the corresponding hydroxy-substituted compound with an activated alkoxycarbonyl derivative where L is a suitable leaving group, as illustrated in Scheme 9.

Scheme 9

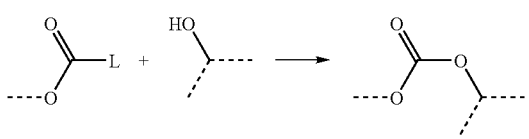

Solvents that can be used are THF, EtOAc, CH$_2$Cl$_2$, CHCl$_3$, CCl$_4$, DMF, DMSO, and the like. The temperature range employed in this transformation may vary between 0° C. and 80° C. Any basic catalyst such as an inorganic base, an amine base, a polymer bound base, and the like can be used to facilitate the reaction.

General Semicarbazone Formation.

Furthermore, where the heteroatom linker is a nitrogen atom, and the functional group present on one spacer linker or the releasable linker is an iminyl derivative, and the functional group present on the other spacer linker or the other releasable linker is an alkylamino or arylaminocarbonyl derivative, the required semicarbazone group can be formed by reacting the corresponding aldehyde or ketone, and a semicarbazide derivative, as illustrated in Scheme 10.

Scheme 10

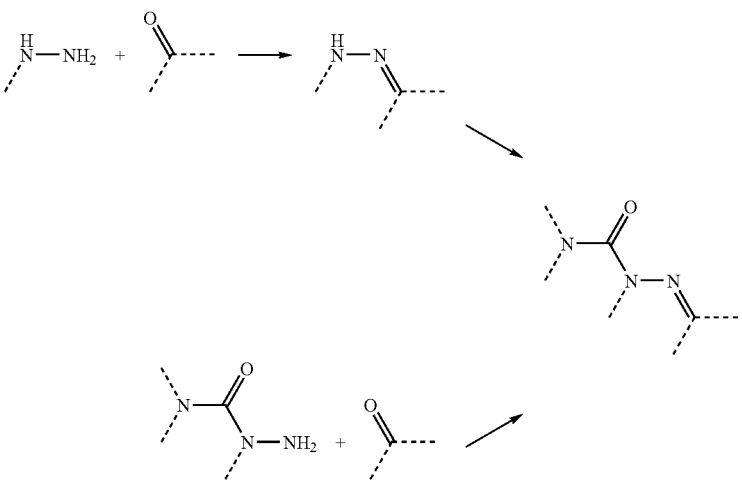

Solvents that can be used are THF, EtOAc, CH$_2$Cl$_2$, CHCl$_3$, CCl$_4$, DMF, DMSO, MeOH and the like. The temperature range employed in this transformation may vary between 0° C. and 80° C. Any acidic catalyst such as a mineral acid, H$_3$CCOOH, F$_3$CCOOH, p-TsOH.H$_2$O, pyridinium p-toluene sulfonate, and the like can be used. In addition, in forming the semicarbazone, the hydrazone functionality may be initially formed by reacting hydrazine with the corresponding aldehyde or ketone. The resulting hydrazone may subsequently by acylated with an isocyanate or a carbamoyl derivative, such as a carbamoyl halide, to form the semicarbazone. Alternatively, the corresponding semicarbazide may be formed by reacting hydrazine with an isocyanate or carbamoyl derivative, such as a carbamoyl halide to form a semicarbazide. Subsequently, the semicarbazide may be reacted with the corresponding aldehyde or ketone to form the semicarbazone.

General Sulfonate Formation.

Furthermore, where the heteroatom linker is an oxygen atom, and the functional group present on the spacer linker or the releasable linker is sulfonyl derivative, the required sulfonate group can be-formed by reacting the corresponding hydroxy-substituted compound with an activated sulfonyl derivative where L is a suitable leaving group such as halo, and the like, as illustrated in Scheme 11.

Scheme 11

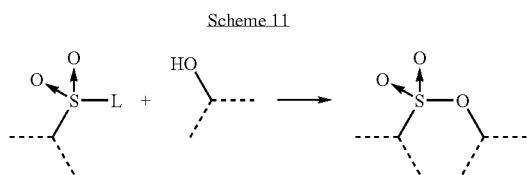

Solvents that can be used are THF, EtOAc, CH$_2$Cl$_2$, CHCl$_3$, CCl$_4$, and the like. The temperature range employed in this transformation may vary between 0° C. and 80° C. Any basic catalyst such as an inorganic base, an amine base, a polymer bound base, and the like can be used to facilitate the reaction.

General Formation of Folate-Peptides.

The folate-containing peptidyl fragment Pte-Glu-(AA)$_n$-NH(CHR$_2$)CO$_2$H (3) is prepared by a polymer-supported sequential approach using standard methods, such as the Fmoc-strategy on an acid-sensitive Fmoc-AA-Wang resin (1), as shown in Scheme 12.

described herein or known in the art are used, where the coupling agent is illustratively applied as the activating reagent to ensure efficient coupling. Fmoc protecting groups are removed after each coupling step under standard conditions, such as upon treatment with piperidine, tetrabutylammonium fluoride (TBAF), and the like. Appropriately protected amino acid building blocks, such as Fmoc-Glu-OtBu, N$^{10}$-TFA-Pte-OH, and the like, are used, as described in Scheme 12, and represented in step (b) by Fmoc-AA-OH. Thus, AA refers to any amino acid starting material, that is appropriately protected. It is to be understood that the term amino acid as used herein is intended to refer to any reagent having both an amine and a carboxylic acid functional group separated by one or more carbons, and includes the naturally occurring alpha and beta amino acids, as well as amino acid derivatives and analogs of these amino acids. In particular, amino acids having side chains that are protected, such as protected serine, threonine, cysteine, aspartate, and the like may also be used in the folate-peptide synthesis described herein. Further, gamma, delta, or longer homologous amino acids may also be included as starting materials in the folate-peptide synthesis described herein. Further, amino acid analogs having homologous side chains, or alternate branching

Scheme 12

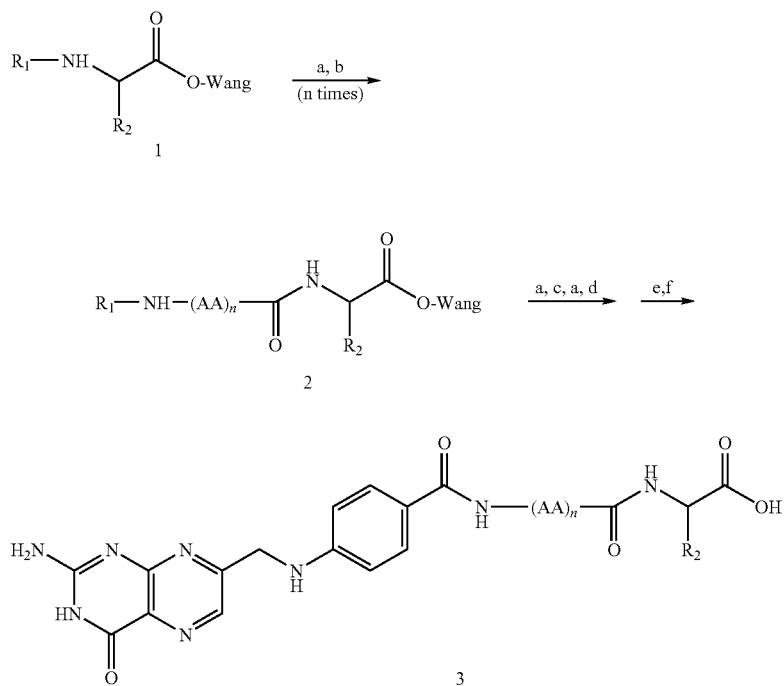

a 20% piperidine/DMF;
b Fmoc-AA-OH, PyBop, DIPEA, DMF;
c Fmoc-Glu(O-t-Bu)——OH; PyBop, DIPEA, DMF;
d 1. N$^{10}$(TFA)-Pte-OH; PyBop, DIPEA, DMSO;
e TFAA, (CH$_2$SH)$_2$, i-Pr$_3$SiH;
f NH$_4$OH, pH 10.3.

In this illustrative embodiment of the processes described herein, R$_1$ is Fmoc, R$_2$ is the desired appropriately-protected amino acid side chain, and DIPEA is diisopropylethylamine. Standard coupling procedures, such as PyBOP and others structures, such as norleucine, isovaline, β-methyl threonine, β-methyl cysteine, β,β-dimethyl cysteine, and the like, may also be included as starting materials in the folate-peptide synthesis described herein.

The coupling sequence (steps (a) & (b)) involving Fmoc-AA-OH is performed "n" times to prepare solid-support peptide 2, where n is an integer and may equal 0 to about 100. Following the last coupling step, the remaining Fmoc group is removed (step (a)), and the peptide is sequentially coupled to a glutamate derivative (step (c)), deprotected, and coupled to TFA-protected pteroic acid (step (d)). Subsequently, the peptide is cleaved from the polymeric support upon treatment with trifluoroacetic acid, ethanedithiol, and triisopropylsilane (step (e)). These reaction conditions result in the simultaneous removal of the t-Bu, t-Boc, and Trt protecting groups that may form part of the appropriately-protected amino acid side chain. The TFA protecting group is removed upon treatment with base (step (f)) to provide the folate-containing peptidyl fragment 3.

The spacer and releasable linkers, and the heteroatom linkers can be combined in a variety of ways. Illustratively, the linkers are attached to each other through an heteroatom linker, such as alkylene--amino--alkylenecarbonyl, alkylene--thio--carbonylalkylsuccinimid-3-yl, and the like, as further illustrated by the following formulae, where the integers x and y are 1, 2, 3, 4, or 5:

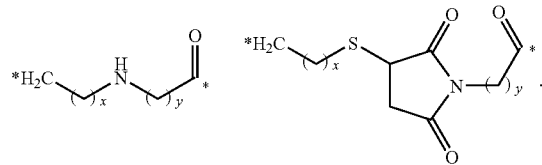

Another illustrative embodiment of the linkers described herein, include releasable linkers that cleave under the conditions described herein by a chemical mechanism involving beta elimination. In one aspect, such releasable linkers include beta-thio, beta-hydroxy, and beta-amino substituted carboxylic acids and derivatives thereof, such as esters, amides, carbonates, carbamates, and ureas. In another aspect, such releasable linkers include 2- and 4-thioarylesters, carbamates, and carbonates.

Furthermore, attachment of the vitamin or drug to the heteroatom linker can be made through a reactive functional group present on the drug or vitamin that has been converted to an heteroatom linker, such as conversion of the aclamycin ketone to the corresponding hydrazone, conversion of folic acid to the corresponding amide, and the like, as illustrated by the following formulae:

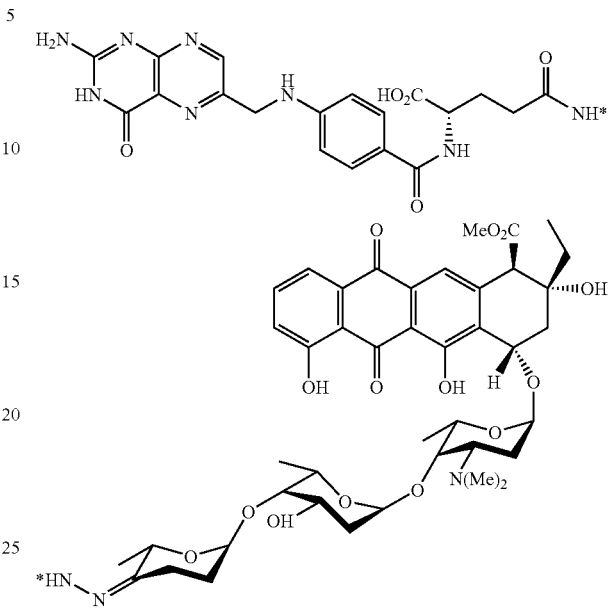

The bivalent linker (L) comprises-one or more components selected from spacer linkers, releasable linkers, heteroatom linkers, and combinations thereof in any order. For example, the spacer linkers, releasable linkers, and heteroatom linkers, and combinations thereof, illustrated in Tables 1 and 2 are contemplated. These lists of linkers are not comprehensive, but are merely illustrative and should not be interpreted as limiting the invention described herein. The asterisks present on the foregoing structures, as well as those shown in Tables 1 and 2, identify illustrative points of attachment for additional spacer, releasable, or heteroatom linkers, or for the drug or the vitamin component of the vitamin receptor binding drug delivery conjugate. It is understood that the bivalent linker L comprises one or more spacer linkers, releasable linkers, and heteroatom linkers, including those illustrated in Tables 1 and 2, and such spacer linkers, releasable linkers, and heteroatom linkers may be combined in any order to form the bivalent linker L.

TABLE 1

Contemplated linkers, and combinations of certain spacer and heteroatom linkers.

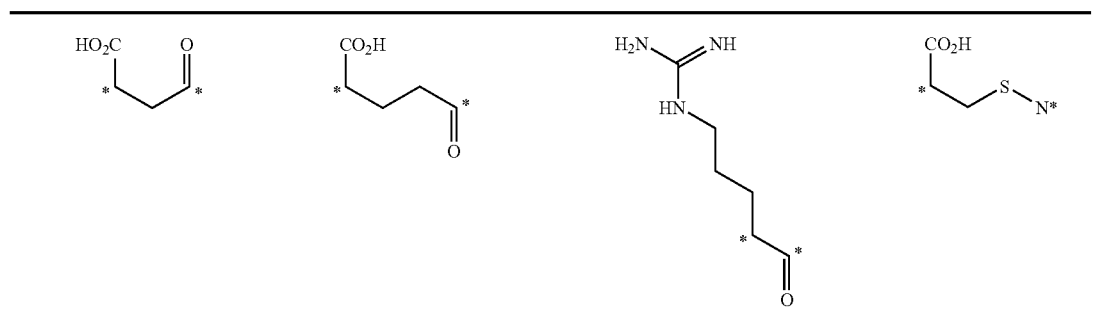

TABLE 1-continued

Contemplated linkers, and combinations of certain spacer and heteroatom linkers.

TABLE 1-continued
Contemplated linkers, and combinations of certain spacer and heteroatom linkers.
| | | | |
|---|---|---|---|
| 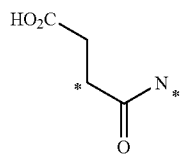 | 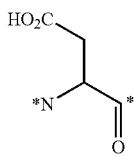 | 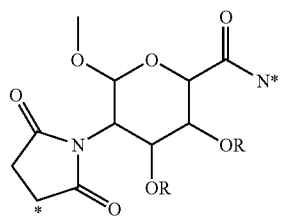<br>R = H, alkyl, acyl | 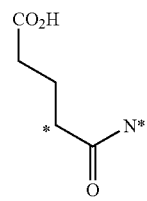 |
| 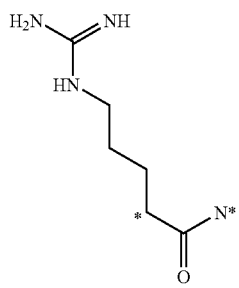 | 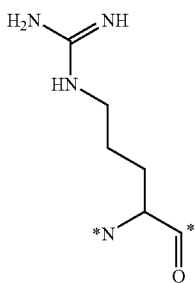 | 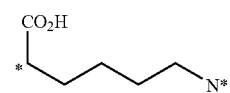 | 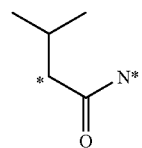 |
| 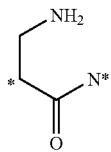 | 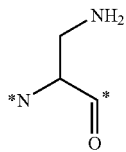 | 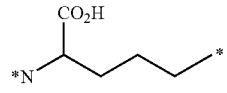 | 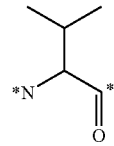 |
| 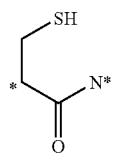 | 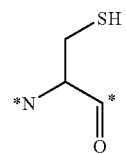 | 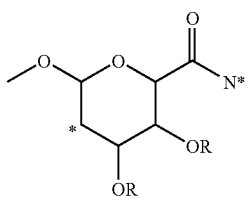<br>R = H, alkyl, acyl | 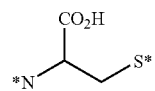 |
| 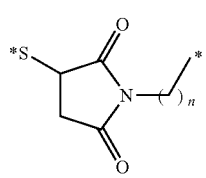<br>n = 0-3 | 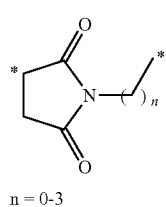<br>n = 0-3 | 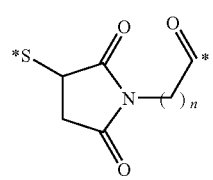<br>n = 1-3 | 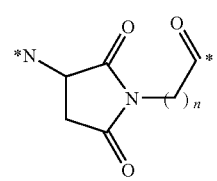<br>n = 1-3 |

TABLE 2
Contemplated linkers, and combinations of certain releasable and heteroatom linkers.
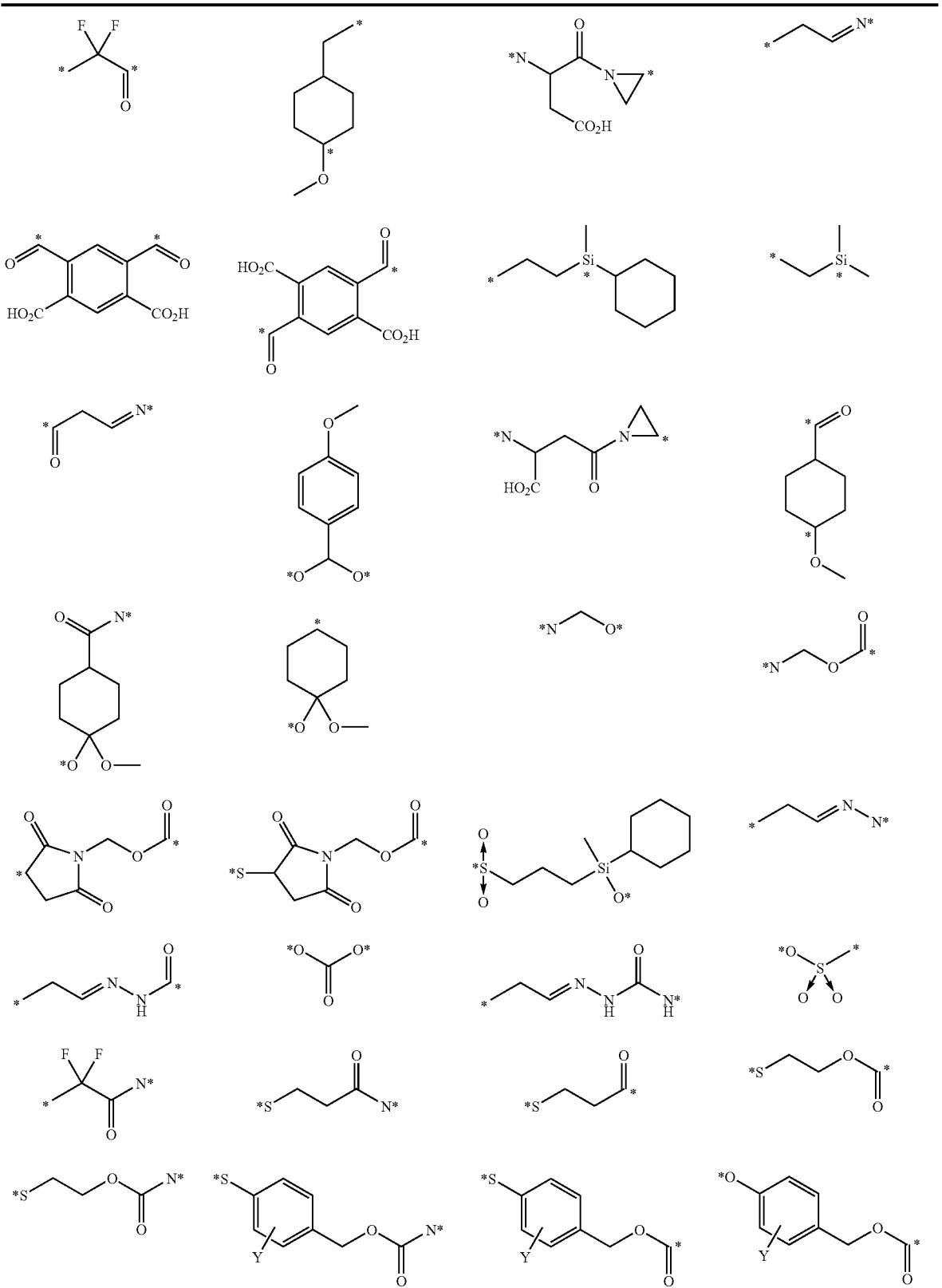

TABLE 2-continued

Contemplated linkers, and combinations of certain releasable and heteroatom linkers.

  

The drug delivery conjugates of the invention may also be made from intermediates. In one embodiment, a compound of the formula:

V-L-$Z^1$ can be made, where $Z^1$ is an electrophile, nucleophile, or precursor, suitable for facilitating attachment of the drug, or analog or derivative thereof.

In one aspect, $Z^1$ can be a leaving group that allows attachment of the drug through a nucleophilic residue present on the drug, or analog or derivative thereof, such as an heteroatom, for example, nitrogen.

In another aspect, $Z^1$ can be a nucleophile, such as an heteroatom, for example nitrogen, capable of displacing a leaving group present on the drug, or analog or derivative thereof, such as a carboxylic acid derivative, for example, an acid chloride.

In another aspect, $Z^1$ can be a precursor, such as a nitro group capable of being elaborated into a nucleophilic nitrogen via a reduction reaction, or an ester capable of being elaborated into an electrophilic acid chloride by sequential hydrolysis and chlorination. It should be appreciated that $Z^1$ can be an heteroatom linker.

In another embodiment, the drug delivery conjugates can be made from intermediates as follows:

$Z^2$-L-D where $Z^2$ is an electrophile, nucleophile, or precursor, suitable for facilitating attachment of the vitamin, or analog or derivative thereof.

In one aspect, $Z^2$ can be a leaving group that allows attachment of the vitamin through a nucleophilic residue present on the vitamin, or analog or derivative thereof, such as an heteroatom, for example, nitrogen.

In another aspect, $Z^2$ can be a nucleophile, such as an heteroatom, for example, nitrogen, capable of displacing a leaving group present on the vitamin, oranalog or derivative thereof, such as a carboxylic acid derivative, for example, an acid chloride.

In another aspect, $Z^2$ can be a precursor, such as a nitro group capable of being elaborated into a nucleophilic nitrogen via a reduction reaction, or an ester capable of being elaborated into an electrophilic acid chloride by sequential hydrolysis and chlorination. It should be appreciated that $Z^2$ can be an heteroatom linker.

In another embodiment, the bivalent linker (L) may be separately synthesized, then attached to the vitamin and the drug in subsequent steps, such as by preparing an intermediate a compound of formula:

$Z^1$-L-$Z^2$ where $Z^1$ and $Z^2$ are each independently selected, and are as defined above.

The drug delivery conjugates of the present invention can be used for both human clinical medicine and veterinary applications. Thus, the host animal harboring the population of pathogenic cells and treated with the vitamin receptor binding drug delivery conjugates can be human or, in the case of veterinary applications, can be a laboratory, agricultural, domestic, or wild animal. The present invention can be applied to host animals including, but not limited to, humans, laboratory animals such rodents (e.g., mice, rats, hamsters, etc.), rabbits, monkeys, chimpanzees, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

The invention is applicable to populations of pathogenic cells that cause a variety of pathologies in these host animals. In accordance with the invention "pathogenic cells" means cancer cells, infectious agents such as bacteria and viruses, bacteria- or virus-infected cells, activated macrophages capable of causing a disease state, and any other type of pathogenic cells that uniquely express, preferentially express, or overexpress vitamin receptors or receptors that bind analogs or derivatives of vitamins. Pathogenic cells can also include any cells causing a disease state for which treatment with the vitamin receptor binding drug delivery conjugates of the present invention results in reduction of the symptoms of the disease. For example, the pathogenic cells can be host cells that are pathogenic under some circumstances such as cells of the immune system that are responsible for graft versus host disease, but not pathogenic under other circumstances.

Thus, the population of pathogenic cells can be a cancer cell population that is tumorigenic, including benign tumors and malignant tumors, or it can be non-tumorigenic. The cancer cell population can arise spontaneously or by such processes as mutations present in the germline of the host animal or somatic mutations, or it can be chemically-, virally-, or radiation-induced. The invention can be utilized to treat such cancers as carcinomas, sarcomas, lymphomas, Hodgekin's disease, melanomas, mesotheliomas, Burkitt's lymphoma, nasopharyngeal carcinomas, leukemias, and myelomas. The cancer cell population can include, but is not limited to, oral, thyroid, endocrine, skin, gastric, esophageal, laryngeal, pancreatic, colon, bladder, bone, ovarian, cervical, uterine, breast, testicular, prostate, rectal, kidney, liver, and lung cancers.

In embodiments where the pathogenic cell population is a cancer cell population, the effect of conjugate administration is a therapeutic response measured by reduction or elimination of tumor mass or of inhibition of tumor cell proliferation. In the case of a tumor, the elimination can be an elimination of cells of the primary tumor or of cells that have metastasized or are in the process of dissociating from the primary tumor. A prophylactic treatment with the vitamin receptor binding drug delivery conjugate to prevent return of a tumor after its removal by any therapeutic approach including surgical removal of the tumor, radiation therapy, chemotherapy, or biological therapy is also contemplated in accordance with this invention. The prophylactic treatment can be an initial treatment with the drug delivery conjugate, such as treatment in a multiple dose daily regimen, and/or can be an additional treatment or series of treatments after an interval of days or months following the initial treatment (s). Accordingly, elimination of any of the pathogenic cell populations treated in accordance with this invention includes reduction in the number of pathogenic cells, inhibition of proliferation of pathogenic cells, a prophylactic treatment that prevents return of pathogenic cells, or a treatment of pathogenic cells that results in reduction of the symptoms of disease.

In cases where cancer cells are being eliminated, the method of the present invention can be used in combination with surgical removal of a tumor, radiation therapy, chemotherapy, or biological therapies such as other immunotherapies including, but not limited to, monoclonal antibody therapy, treatment with immunomodulatory agents, adoptive transfer of immune effector cells, treatment with hematopoietic growth factors, cytokines and vaccination.

The invention is also applicable to populations of pathogenic cells that cause a variety of infectious diseases. For example, the present invention is applicable to such populations of pathogenic cells as bacteria, fungi, including yeasts, viruses, virus-infected cells, mycoplasma, and parasites. Infectious organisms that can be treated with the drug delivery conjugates of the present invention are any art-recognized infectious organisms that cause pathogenesis in an animal, including such organisms as bacteria that are gram-negative or gram-positive cocci or bacilli. For example, *Proteus* species, *Klebsiella* species, *Providencia* species, *Yersinia* species, *Erwinia* species, *Enterobacter* species, *Salmonella* species, *Serratia* species, *Aerobacter* species, *Escherichia* species, *Pseudomonas* species, *Shigella* species, *Vibrio* species, *Aeromonas* species, *Campylobacter* species, *Streptococcus* species, *Staphylococcus* species, *Lactobacillus* species, *Micrococcus* species, *Moraxella* species, *Bacillus* species, *Clostridium* species, *Corynebacterium* species, *Eberthella* species, *Micrococcus* species, *Mycobacterium* species, *Neisseria* species, *Haemophilus* species, *Bacteroides* species, *Listeria* species, *Erysipelothrix* species, *Acinetobacter* species, *Brucella* species, *Pasteurella* species, *Vibrio* species, *Flavobacterium* species, *Fusobacterium* species, *Streptobacillus* species, *Calymmatobacterium* species, *Legionella* species, *Treponema* species, *Borrelia* species, *Leptospira* species, *Actinomyces* species, *Nocardia* species, *Rickettsia* species, and any other bacterial species that causes disease in a host can be treated with the drug delivery conjugates of the invention.

Of particular interest are bacteria that are resistant to antibiotics such as antibiotic-resistant *Streptococcus* species and *Staphlococcus* species, or bacteria that are susceptible to antibiotics, but cause recurrent infections treated with antibiotics so that resistant organisms eventually develop. Bacteria that are susceptible to antibiotics, but cause recurrent infections treated with antibiotics so that resistant organisms eventually develop, can be treated with the drug delivery conjugates of the present invention in the absence of antibiotics, or in combination with lower doses of antibiotics than would normally be administered to a patient, to avoid the development of these antibiotic-resistant bacterial strains.

Viruses, such as DNA and RNA viruses, can also be treated in accordance with the invention. Such viruses include, but are not limited to, DNA viruses such as papilloma viruses, parvoviruses, adenoviruses, herpesviruses and vaccinia viruses, and RNA viruses, such as arenaviruses, coronaviruses, rhinoviruses, respiratory syncytial viruses, influenza viruses, picornaviruses, paramyxoviruses, reoviruses, retroviruses, lentiviruses, and rhabdoviruses.

The present invention is also applicable to any fungi, including yeasts, *mycoplasma* species, parasites, or other infectious organisms that cause disease in animals. Examples of fungi that can be treated with the method and compositions of the present invention include fungi that grow as molds or are yeastlike, including, for example, fungi that cause diseases such as ringworm, histoplasmosis, blastomycosis, aspergillosis, cryptococcosis, sporotrichosis, coccidioidomycosis, paracoccidioidomycosis, mucormycosis, chromoblastomycosis, dermatophytosis, protothecosis, fusariosis, pityriasis, mycetoma, paracoccidioidomycosis, phaeohyphomycosis, pseudallescheriasis, sporotrichosis, trichosporosis, pneumocystis infection, and candidiasis.

The present invention can also be utilized to treat parasitic infections including, but not limited to, infections caused by tapeworms, such as *Taenia, Hymenolepsis, Diphyllobothrium*, and *Echinococcus* species, flukes, such as *Fasciolopsis, Heterophyes, Metagonimus, Clonorchis, Fasciola, Paragonimus*, and *Schitosoma* species, roundworms, such as *Enterobius, Trichuris, Ascaris, Ancylostoma, Necator, Strongyloides, Trichinella, Wuchereria, Brugia, Loa Onchocerca*, and *Dracunculus* species, ameba, such as *Naegleria* and *Acanthamoeba* species, and protozoans, such as *Plasmodium, Trypanosoma, Leishmania, Toxoplasma, Entamoeba, Giardia, Isospora, Cryptosporidium*, and *Enterocytozoon* species.

The pathogenic cells to which the drug delivery conjugates of the invention are directed can also be cells harboring endogenous pathogens, such as virus-, mycoplasma-, parasite-, or bacteria-infected cells, if these cells preferentially express vitamin receptors.

In one embodiment, the vitamin receptor binding drug delivery conjugates can be internalized into the targeted pathogenic cells upon binding of the vitamin moiety to a vitamin receptor, transporter, or other surface-presented protein that specifically binds the vitamin and which is preferentially expressed on the pathogenic cells. Such internalization can occur, for example, through receptor-mediated endocytosis. If the drug delivery conjugate contains a releasable linker, the vitamin moiety and the drug can dissociate intracellularly and the drug can act on its intracellular target.

In an alternate embodiment, the vitamin moiety of the drug delivery conjugate can bind to the pathogenic cell placing the drug in close association with the surface of the pathogenic cell. The drug can then be released by cleavage of the releasable linker. For example, the drug can be released by a protein disulfide isomerase if the releasable linker is a disulfide group. The drug can then be taken up by the pathogenic cell to which the vitamin receptor binding drug delivery conjugate is bound, or the drug can be taken up by another pathogenic cell in close proximity thereto. Alternatively, the drug could be released by a protein disulfide isomerase inside the cell where the releasable linker is a disulfide group. The drug may also be released by a hydrolytic mechanism, such as acid-catalyzed hydrolysis, as described above for certain beta elimination mechanisms, or by an anchimerically assisted cleavage through an oxonium ion or lactonium ion producing mechanism. The selection of the releasable linker or linkers will dictate the mechanism by which the drug is released from the conjugate. It is appreciated that such a selection can be predefined by the conditions wherein the drug conjugate will be used.

In another embodiment, where the linker does not comprise a releasable linker, the vitamin moiety of the drug delivery conjugate can bind to the pathogenic cell placing the drug on the surface of the pathogenic cell to target the pathogenic cell for attack by other molecules capable of binding to the drug. Alternatively, in this embodiment, the drug delivery conjugates can be internalized into the targeted cells upon binding, and the vitamin moiety and the drug can remain associated intracellularly with the drug exhibiting its effects without dissociation from the vitamin moiety.

In still another embodiment, or in combination with the above-described embodiments, the vitamin receptor binding drug delivery conjugate can act through a mechanism independent of cellular vitamin receptors. For example, the drug delivery conjugates can bind to soluble vitamin receptors present in the serum or to serum proteins, such as albumin, resulting in prolonged circulation of the conjugates relative to the unconjugated drug, and in increased activity of the conjugates towards the pathogenic cell population relative to the unconjugated drug.

In another embodiment of this invention, a vitamin receptor binding drug delivery conjugate of the general formula V-L-D is provided. L is selected from $(l_s)_a$ and $(l_H)_b$, and combinations thereof, where $(l_s)_a$, $(l_H)_b$, and V are as defined herein, and D is a drug such as an immunogen. The immunogen can be a hapten, for example, fluorescein, dinitrophenyl, and the like. In this embodiment, the vitamin receptor binding drug delivery conjugate binds to the surface of the pathogenic cells and "labels" the cells with the immunogen, thereby triggering an immune response directed at the labeled pathogenic cell population. Antibodies administered to the host in a passive immunization or antibodies existing in the host system from a preexisting innate or acquired immunity bind to the immunogen and trigger endogenous immune responses. Antibody binding to the cell-bound vitamin-immunogen conjugate results in complement-mediated cytotoxicity, antibody-dependent cell-mediated cytotoxicity, antibody opsonization and phagocytosis, antibody-induced receptor clustering signaling cell death or quiescence, or any other humoral or cellular immune response stimulated by antibody binding to cell-bound ligand-immunogen conjugates. In cases where an immunogen can be directly recognized by immune cells without prior antibody opsonization, direct killing of the pathogenic cells can occur. This embodiment is described in more detail in U.S. patent application Ser. No. 09/822,379, incorporated herein by reference. It is appreciated that in certain variations of this embodiment where the drug is an immunogen, the bivalent linker may also include releasable linkers, as described above, such as a vitamin receptor binding drug delivery conjugate of the general formula V-L-D where L is selected from $(l_s)_a$; $(l_H)_b$, $(l_r)_c$, and combinations thereof where $(l_s)$ is a spacer linker, $(l_H)$ is an heteroatom linker, $(l_r)$ is a releasable linker, V is a vitamin, or an analog or a derivative thereof, and a, b, and c are integers.

The vitamin receptor binding drug delivery conjugates described herein comprise a vitamin receptor binding moiety, a bivalent linker (L), a drug, and, optionally, heteroatom linkers to link the vitamin receptor binding moiety and the drug to the bivalent linker (L). The bivalent linker (L) can comprise a spacer linker, a releasable (i.e., cleavable) linker, and an heteroatom linker, or combinations thereof.

The vitamin receptor binding drug delivery conjugates described herein can be formed from a wide variety of vitamins or receptor-binding vitamin analogs/derivatives, linkers, and drugs. The drug delivery conjugates of the present invention are capable of selectively targeting a population of pathogenic cells in the host animal due to preferential expression of a receptor for the vitamin, accessible for vitamin binding, on the pathogenic cells. Illustrative vitamin moieties include carnitine, inositol, lipoic acid, pyridoxal, ascorbic acid, niacin, pantothenic acid, folic acid, riboflavin, thiamine, biotin, vitamin $B_{12}$, and the lipid soluble vitamins A, D, E and K. These vitamins, and their receptor-binding analogs and derivatives, constitute the targeting entity that can be coupled with the drug by bivalent linker (L) to form the vitamin receptor binding drug delivery conjugates described herein. Therefore, the term "vitamin" includes vitamin analogs and/or derivatives (e.g., pteroic acid which is a derivative of folate, biotin analogs such as biocytin, biotin sulfoxide, oxybiotin and other biotin receptor-binding compounds, and the like). It should be appreciated that in accordance with this invention, vitamin analogs or derivatives can mean a vitamin that incorporates an heteroatom through which the vitamin analog or derivative is covalently bound to the bivalent linker (L).

Illustrative vitamin moieties include folic acid, biotin, riboflavin, thiamine, vitamin $B_{12}$, and receptor-binding analogs and derivatives of these vitamin molecules, and other related vitamin receptor binding molecules. Illustrative embodiments of vitamin analogs and/or derivatives include analogs and derivatives of folate such as folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refer to the art-recognized analogs having a carbon atom substituted for one or two nitrogen atoms in the naturally occurring folic acid structure, or analog or derivative thereof. For example, the deaza analogs include the 1-deaza, 3-deaza, 5-deaza, 8-deaza, and 10-deaza analogs of folate. The dideaza analogs include, for example, 1,5-dideaza, 5,10-dideaza, 8,10-dideaza, and 5,8-dideaza analogs of folate. Other folates useful as complex forming ligands for this invention are the folate receptor-binding analogs anminopterin, amethopterin (methotrexate), $N^{10}$-methylfolate, 2-deamino-hydroxyfolate, deaza analogs such as 1-deazamethopterin or 3-deazamethopterin, and 3',5'-dichloro-4-amino-4-deoxy-$N^{10}$-methylpteroylglutamic acid (dichloromethotrexate). The foregoing folic acid analogs and/or derivatives are conventionally termed "folates," reflecting their ability to bind with folate-receptors, and such ligands when conjugated with exogenous molecules are effective to enhance transmembrane transport, such as via folate-mediated endocytosis as described herein. Other suitable ligands capable of binding to folate receptors to initiate receptor mediated endocytotic transport of the complex include anti-idiotypic antibodies to the folate receptor. An exogenous molecule in complex with an anti-idiotypic antibody to a folate receptor is used to trigger transmembrane transport of the complex in accordance with the present invention.

Illustrative embodiments of vitamin analogs and/or derivatives also include analogs and derivatives of biotin such as biocytin, biotin sulfoxide, oxybiotin and other biotin receptor-binding compounds, and the like. It is appreciated that analogs and derivatives of the other vitamins described herein are also contemplated herein. In one embodiment, vitamins that can be used in the drug delivery conjugates described herein include those that bind to vitamin receptors expressed specifically on activated macrophages, such as the folate receptor, which binds folate, or an analog or derivative thereof as described herein.

The binding site for the vitamin can include receptors for any vitamin molecule, or a derivative or analog thereof, capable of specifically binding to a receptor wherein the receptor or other protein is uniquely expressed, overexpressed, or preferentially expressed by a population of pathogenic cells. A surface-presented protein uniquely expressed, overexpressed, or preferentially expressed by the pathogenic cells is typically a receptor that is either not present or present at lower concentrations on non-pathogenic cells providing a means for selective elimination of the pathogenic cells. The vitamin receptor binding drug delivery conjugates may be capable of high affinity binding to receptors on cancer cells or other types of pathogenic cells. The high affinity binding can be inherent to the vitamin moiety or the binding affinity can be enhanced by the use of a chemically modified vitamin (i.e., an analog or a derivative).

The drug can be any molecule capable of modulating or otherwise modifying cell function, including pharmaceutically active compounds. Suitable molecules can include, but are not limited to: peptides, oligopeptides, retro-inverso oligopeptides, proteins, protein analogs in which at least one non-peptide linkage replaces a peptide linkage, apoproteins, glycoproteins, enzymes, coenzymes, enzyme inhibitors, amino acids and their derivatives, receptors and other membrane proteins; antigens and antibodies thereto; haptens and antibodies thereto; hormones, lipids, phospholipids, liposomes; toxins; antibiotics; analgesics; bronchodilators; beta-blockers; antimicrobial agents; antihypertensive agents; cardiovascular agents including antiarrhythmics, cardiac glycosides, antianginals and vasodilators; central nervous system agents including stimulants, psychotropics, antimanics, and depressants; antiviral agents; antihistamines; cancer drugs including chemotherapeutic agents; tranquilizers; antidepressants; H-2 antagonists; anticonvulsants; antinauseants; prostaglandins and prostaglandin analogs; muscle relaxants; anti-inflammatory substances; stimulants; decongestants; antiemetics; diuretics; antispasmodics; antiasthmatics; anti-Parkinson agents; expectorants; cough suppressants; mucolytics; and mineral and nutritional additives.

Further, the drug can be any drug known in the art which is cytotoxic, enhances tumor permeability, inhibits tumor cell proliferation, promotes apoptosis, decreases anti-apoptotic activity in target cells, is used to treat diseases caused by infectious agents, enhances an endogenous immune response directed to the pathogenic cells, or is useful for treating a disease state caused by any type of pathogenic cell. Drugs suitable for use in accordance with this invention include adrenocorticoids and corticosteroids, alkylating agents, anti-androgens, antiestrogens, androgens, aclamycin and aclamycin derivatives, estrogens, antimetabolites such as cytosine arabinoside, purine analogs, pyrimidine analogs, and methotrexate, busulfan, carboplatin, chlorambucil, cisplatin and other platinum compounds, tamoxiphen, taxol, paclitaxel, paclitaxel derivatives, Taxotere®, cyclophosphamide, daunomycin, rhizoxin, T2 toxin, plant alkaloids, prednisone, hydroxyurea, teniposide, mitomycins, discodermolides, microtubule inhibitors, epothilones, tubulysin, cyclopropyl benz[e]indolone, seco-cyclopropyl benz[e]indolone, O-Ac-seco-cyclopropyl benz[e]indolone, bleomycin and any other antibiotic, nitrogen mustards, nitrosureas, vincristine, vinblastine, and analogs and derivative thereof such as deacetylvinblastine monohydrazide, colchicine, colchicine derivatives, allocolchicine, thiocolchicine, trityl cysteine, Halicondrin B, dolastatins such as dolastatin 10, amanitins such as α-amanitin, camptothecin, irinotecan, and other camptothecin derivatives thereof, geldanamycin and geldanamycin derivatives, estramustine, nocodazole, MAP4, colcemid, inflammatory and proinflammatory agents, peptide and peptidomimetic signal transduction inhibitors, and any other art-recognized drug or toxin. Other drugs that can be used in accordance with the invention include penicillins, cephalosporins, vancomycin, erythromycin, clindamycin, rifampin, chloramphenicol, aminoglycoside antibiotics, gentamicin, amphotericin B, acyclovir, trifluridine, ganciclovir, zidovudine, amantadine, ribavirin, and any other art-recognized antimicrobial compound.

In one embodiment, the drugs for use in accordance with this invention remain stable in serum for at least 4 hours. In another embodiment the drugs have an $IC_{50}$ in the nanomolar range, and, in another embodiment, the drugs are water soluble. If the drug is not water soluble, the bivalent linker (L) can be derivatized to enhance water solubility. The term "drug" also means any of the drug analogs or derivatives described hereinabove, including but not limited to the dolastatins such as dolastatin 10, the amanitins such as α-amanitin, camptothecins and irinotecans, and other camptothecin and irinotecan derivatives thereof. It should be appreciated that in accordance with this invention, a drug analog or derivative can mean a drug that incorporates an heteroatom through which the drug analog or derivative is covalently bound to the bivalent linker (L).

The vitamin receptor binding drug delivery conjugates of the present invention can comprise a vitamin receptor binding moiety, a bivalent linker (L), a drug, and, optionally, heteroatom linkers to link the vitamin receptor binding moiety and the drug to the bivalent linker (L). It should be appreciated that in accordance with this invention, a vitamin analog or derivative can mean a vitamin that incorporates an heteroatom through which the vitamin analog or derivative is covalently bound to the bivalent linker (L). Thus, the vitamin can be covalently bound to the bivalent linker (L) through an heteroatom linker, or a vitamin analog or derivative (i.e., incorporating an heteroatom) can be directly bound to the bivalent linker (L). Similarly, a drug analog or derivative is a drug in accordance with the invention and a drug analog or derivative can mean a drug that incorporates an heteroatom through which the drug analog or derivative is covalently bound to the bivalent linker (L). Thus, the drug can be covalently bound to the bivalent linker (L) through an heteroatom linker, or a drug analog or derivative (i.e., incorporating an heteroatom) can be directly bound to the bivalent linker (L). The bivalent linker (L) can comprise a spacer linker, a releasable (i.e., cleavable) linker, and an heteroatom linker to link the spacer linker to the releasable linker in conjugates containing both of these types of linkers.

Thus, in accordance with this invention the bivalent linker (L) can comprise a means for associating the vitamin with the drug, such as by connection through heteroatom linkers (i.e., spacer arms or bridging molecules), or by direct covalent bonding of the bivalent linker (L) to a vitamin or drug analog or derivative. Either means for association should not prevent the binding of the vitamin, or vitamin receptor binding derivative or analog, to the vitamin receptor on the cell membrane for operation of the method of the present invention.

Generally, any manner of forming a conjugate between the bivalent linker (L) and the vitamin, or analog or derivative thereof, between the bivalent linker (L) and the drug, or analog or derivative thereof, including any intervening heteroatom linkers, can be utilized in accordance with the present invention. Also, any art-recognized method of forming a conjugate between the spacer linker, the releasable linker, and the heteroatom linker to form the bivalent linker (L) can be used. The conjugate can be formed by direct conjugation of any of these molecules, for example, through hydrogen, ionic, or covalent bonds. Covalent bonding can occur, for example, through the formation of amide, ester, disulfide, or imino bonds between acid, aldehyde, hydroxy, amino, sulfhydryl, or hydrazo groups.

The spacer and/or releasable linker (i.e., cleavable linker) can be any biocompatible linker. The cleavable linker can be, for example, a linker susceptible to cleavage under the reducing or oxidizing conditions present in or on cells, a pH-sensitive linker that may be an acid-labile or base-labile linker, or a linker that is cleavable by biochemical or metabolic processes, such as an enzyme-labile linker. Typically, the spacer and/or releasable linker comprises about 1 to about 30 carbon atoms, more typically about 2 to about 20 carbon atoms. Lower molecular weight linkers (i.e., those having an approximate molecular weight of about 30 to about 300) are typically employed. Precursors to such linkers are typically selected to have either nucleophilic or electrophilic functional groups, or both, optionally in a protected form with a readily cleavable protecting group to facilitate their use in synthesis of the intermediate species.

The invention is also directed to pharmaceutical compositions comprising an amount of a vitamin receptor binding drug delivery conjugate effective to eliminate a population of pathogenic cells in a host animal when administered in one or more doses. The drug delivery conjugate is preferably administered to the host animal parenterally, e.g., intradermally, subcutaneously, intramuscularly, intraperitoneally, intravenously, or intrathecally. Alternatively, the drug delivery conjugate can be administered to the host animal by other medically useful processes, such as orally, and any effective dose and suitable therapeutic dosage form, including prolonged release dosage forms, can be used.

Examples of parenteral dosage forms include aqueous solutions of the active agent, in an isotonic saline, 5% glucose or other well-known pharmaceutically acceptable liquid carriers such as liquid alcohols, glycols, esters, and amides. The parenteral dosage form in accordance with this invention can be in the form of a reconstitutable lyophilizate comprising the dose of the drug delivery conjugate. In one aspect of the present embodiment, any of a number of prolonged release dosage forms known in the art can be administered such as, for example, the biodegradable carbohydrate matrices described in U.S. Pat. Nos. 4,713,249; 5,266,333; and 5,417,982, the disclosures of which are incorporated herein by reference, or, alternatively, a slow pump (e.g., an osmotic pump) can be used.

At least one additional composition comprising a therapeutic factor can be administered to the host in combination or as an adjuvant to the above-detailed methodology, to enhance the drug delivery conjugate-mediated elimination of the population of pathogenic cells, or more than one additional therapeutic factor can be administered. The therapeutic factor can be selected from a compound capable of stimulating an endogenous immune response, a chemotherapeutic agent, or another therapeutic factor capable of complementing the efficacy of the administered drug delivery conjugate. The method of the invention can be performed by administering to the host, in addition to the above-described conjugates, compounds or compositions capable of stimulating an endogenous immune response (e.g. a cytokine) including, but not limited to, cytokines or immune cell growth factors such as interleukins 1-18, stem cell factor, basic FGF, EGF, G-CSF, GM-CSF, FLK-2 ligand, HILDA, MIP-1α, TGF-α, TGF-β, M-CSF, IFN-α, IFN-β, IFN-γ, soluble CD23, LIF, and combinations thereof.

Therapeutically effective combinations of these factors can be used. In one embodiment, for example, therapeutically effective amounts of IL-2, for example, in amounts ranging from about 0.1 MIU/m$^2$/dose/day to about 15 MIU/m$^2$/dose/day in a multiple dose daily regimen, and IFN-α, for example, in amounts ranging from about 0.1 MIU/m$^2$/dose/day to about 7.5 MIU/m$^2$/dose/day in a multiple dose daily regimen, can be used along with the drug delivery conjugates to eliminate, reduce, or neutralize pathogenic cells in a host animal harboring the pathogenic cells (MIU=million international units; m$^2$=approximate body surface area of an average human). In another embodiment IL-12 and IFN-α are used in the above-described therapeutically effective amounts for interleukins and interferons, and in yet another embodiment IL-15 and IFN-α are used in the above described therapeutically effective amounts for interleukins and interferons. In an alternate embodiment IL-2, IFN-α or IFN-γ, and GM-CSF are used in combination in the above described therapeutically effective amounts. The invention also contemplates the use of any other effective combination of cytokines including combinations of other interleukins and interferons and colony stimulating factors.

Chemotherapeutic agents, which are, for example, cytotoxic themselves or can work to enhance tumor permeability, are also suitable for use in the method of the invention in combination with the drug delivery conjugates. Such chemotherapeutic agents include adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and methotrexate, busulfan, carboplatin, chlorambucil, cisplatin and other platinum compounds, tamoxiphen, taxol, paclitaxel, paclitaxel derivatives, Taxotere®, cyclophosphamide, daunomycin, rhizoxin, T2 toxin, plant alkaloids, prednisone, hydroxyurea, teniposide, mitomycins, discodermolides, microtubule inhibitors, epothilones, tubulysin, cyclopropyl benz[e]indolone, seco-cyclopropyl benz[e]indolone, O-Ac-seco-cyclopropyl benz[e]indolone, bleomycin and any other antibiotic, nitrogen mustards, nitrosureas, vincristine, vinblastine, and analogs and derivative thereof such as deacetylvinblastine monohydrazide, colchicine, colchicine derivatives, allocolchicine, thiocolchicine, trityl cysteine, Halicondrin B, dolastatins such as dolastatin 10, amanitins such as α-amanitin, camptothecin, irinotecan, and other camptothecin derivatives thereof, geldanamycin and geldanamycin derivatives, estramustine, nocodazole, MAP4, colcemid, inflammatory and proinflammatory agents, peptide and peptidomimetic signal transduction inhibitors, and any other art-recognized drug or toxin. Other drugs that can be used in accordance with the invention include penicillins, cephalosporins, vancomycin, erythromycin, clindamycin, rifampin, chloramphenicol, aminoglycoside antibiotics, gentamicin, amphotericin B, acyclovir, trifluridine, ganciclovir, zidovudine, amantadine, ribavirin, maytansines and analogs and derivatives thereof, gemcitabine, and any other art-recognized antimicrobial compound.

The therapeutic factor can be administered to the host animal prior to, after, or at the same time as the vitamin receptor binding drug delivery conjugates and the therapeutic factor can be administered as part of the same composition containing the drug delivery conjugate or as part of a different composition than the drug delivery conjugate. Any such therapeutic composition containing the therapeutic factor at a therapeutically effective dose can be used in the present invention.

Additionally, more than one type of drug delivery conjugate can be used. For example, the host animal can be treated with conjugates with different vitamins, but the same drug (e.g., folate-mitomycin conjugates and vitamin B$_{12}$-mitomycin conjugates) in a co-dosing protocol. In other embodiments, the host animal can be treated with conjugates comprising the same vitamin linked to different drugs, or various vitamins linked to various drugs. For example, the host animal could be treated with a folate-mitomycin and a folate-cisplatin conjugate, or with a folate-mitomycin conjugate and a vitamin $B_{12}$-cisplatin conjugate. Furthermore, drug delivery conjugates with the same or different vitamins, and the same or different drugs comprising multiple vitamins and multiple drugs as part of the same drug delivery conjugate could be used.

The unitary daily dosage of the drug delivery conjugate can vary significantly depending on the host condition, the disease state being treated, the molecular weight of the conjugate, its route of administration and tissue distribution, and the possibility of co-usage of other therapeutic treatments such as radiation therapy. The effective amount to be administered to a patient is based on body surface area, patient weight, and physician assessment of patient condition. Effective doses can range, for example, from about 1 ng/kg to about 1 mg/kg, from about 1 µg/kg to about 500 µg/kg, and from about 1 µg/kg to about 100 µg/kg.

Any effective regimen for administering the drug delivery conjugates can be used. For example, the drug delivery conjugates can be administered as single doses, or can be divided and administered as a multiple-dose daily regimen. Further, a staggered regimen, for example, one to three days per week can be used as an alternative to daily treatment, and for the purpose of defining this invention such intermittent or staggered daily regimen is considered to be equivalent to every day treatment and within the scope of this invention. In one embodiment of the invention the host is treated with multiple injections of the drug delivery conjugate to eliminate the population of pathogenic cells. In one embodiment, the host is injected multiple times (preferably about 2 up to about 50 times) with the drug delivery conjugate, for example, at 12-72 hour intervals or at 48-72 hour intervals. Additional injections of the drug delivery conjugate can be administered to the patient at an interval of days or months after the initial injections(s) and the additional injections prevent recurrence of the disease state caused by the pathogenic cells.

In one embodiment, vitamins, or analogs or derivatives thereof, that can be used in the drug delivery conjugates of the present invention include those that bind to receptors expressed specifically on activated macrophages, such as the folate receptor which binds folate, or an analog or derivative thereof. The folate-linked conjugates, for example, can be used to kill or suppress the activity of activated macrophages that cause disease states in the host. Such macrophage targeting conjugates, when administered to a patient suffering from an activated macrophage-mediated disease state, work to concentrate and associate the conjugated drug in the population of activated macrophages to kill the activated macrophages or suppress macrophage function. Elimination, reduction, or deactivation of the activated macrophage population works to stop or reduce the activated macrophage-mediated pathogenesis characteristic of the disease state being treated. Exemplary of diseases known to be mediated by activated macrophages include rheumatoid arthritis, ulcerative colitis, Crohn's disease, psoriasis, osteomyelitis, multiple sclerosis, atherosclerosis, pulmonary fibrosis, sarcoidosis, systemic sclerosis, organ transplant rejection (GVHD) and chronic inflammations. Administration of the drug delivery conjugate is typically continued until symptoms of the disease state are reduced or eliminated.

The drug delivery conjugates administered to kill activated macrophages or suppress the function of activated macrophages can be administered parenterally to the animal or patient suffering from the disease state, for example, intradermally, subcutaneously, intramuscularly, intraperitoneally, or intravenously in combination with a pharmaceutically acceptable carrier. Alternatively, the drug delivery conjugates can be administered to the animal or patient by other medically useful procedures and effective doses can be administered in standard or prolonged release dosage forms. The therapeutic method can be used alone or in combination with other therapeutic methods recognized for treatment of disease states mediated by activated macrophages.

The following drug delivery conjugates are illustrative of drug delivery conjugates that are contemplated to fall within the scope of the invention described herein. These drug delivery conjugates can be prepared in accordance with the invention using the procedures described herein in addition to art-recognized protocols.

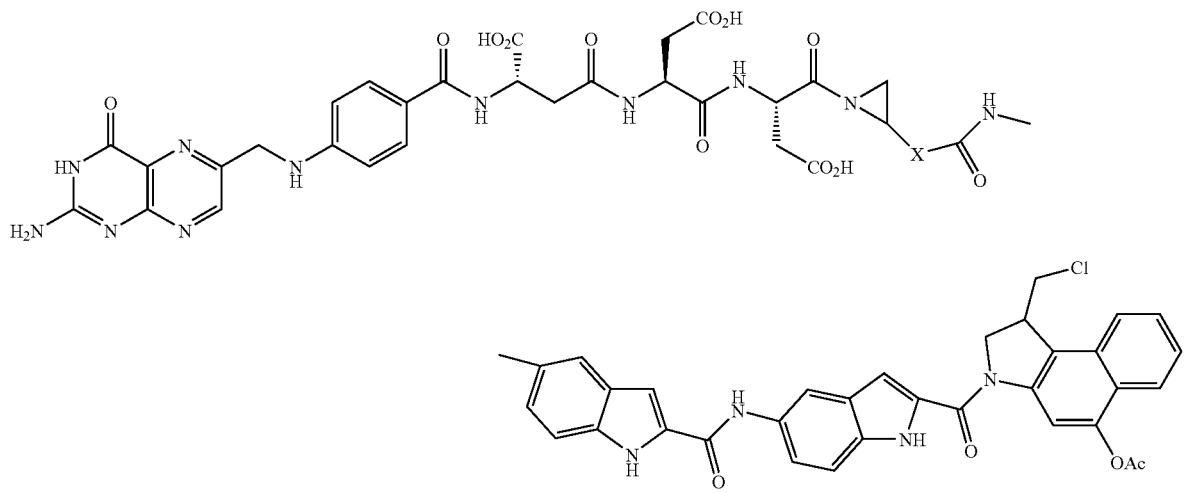

$X = (CH_2)_n$, n = 0, 1, 2, 3, 4

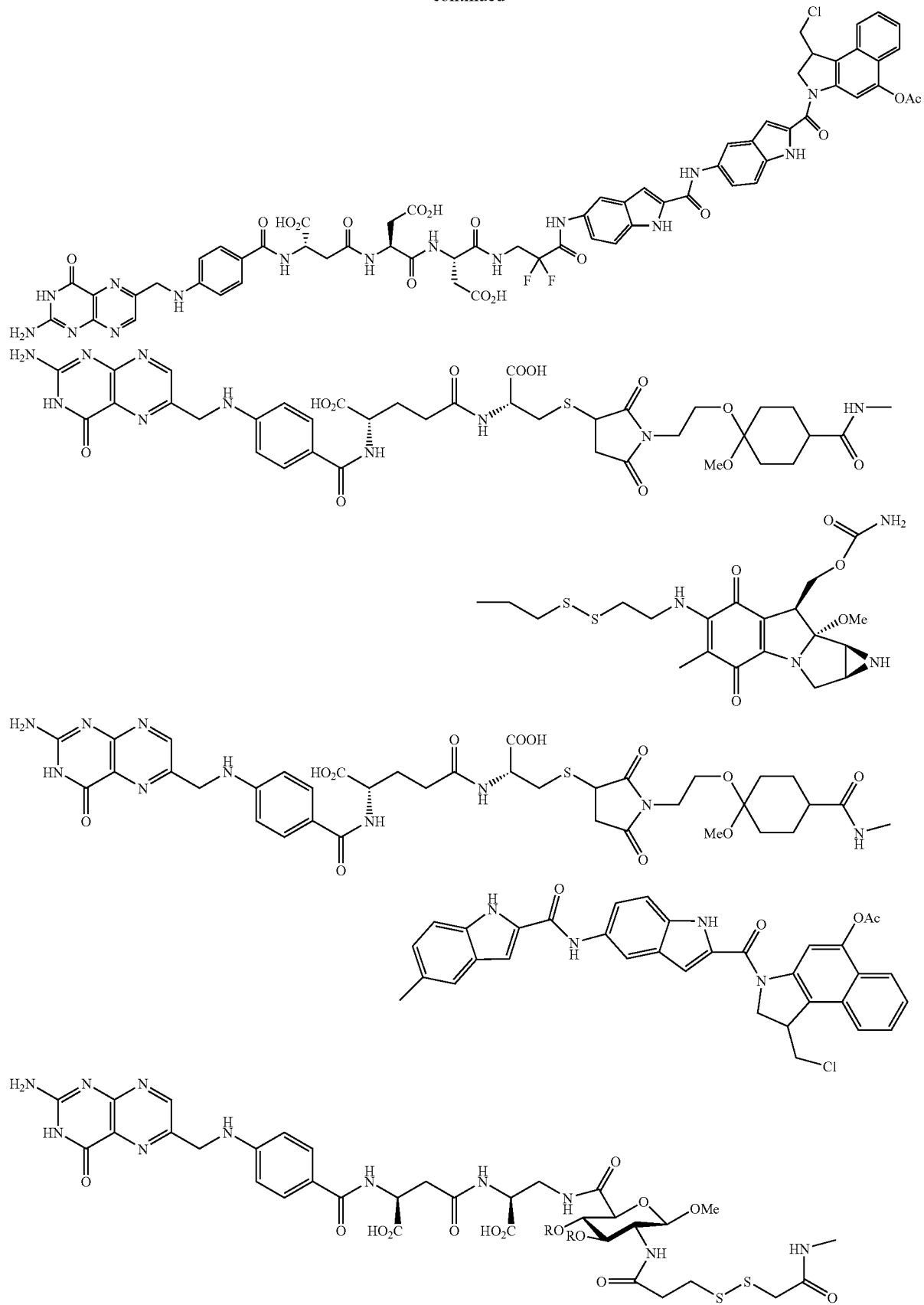

-continued
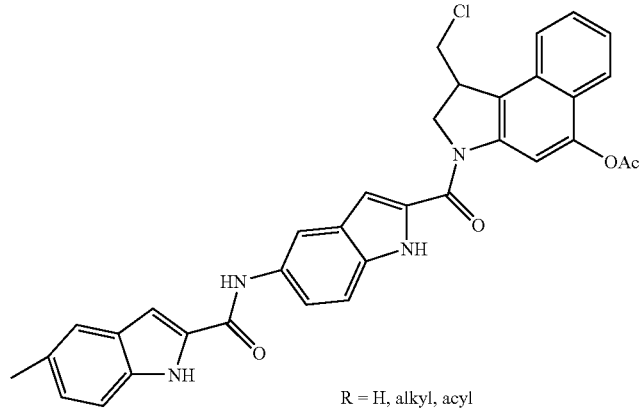
R = H, alkyl, acyl
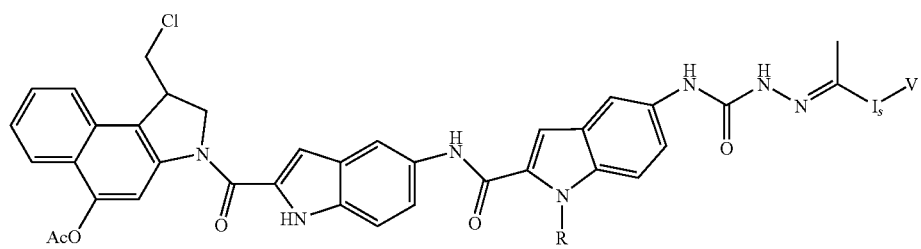
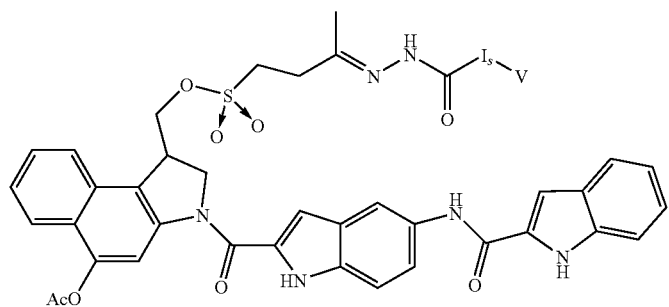
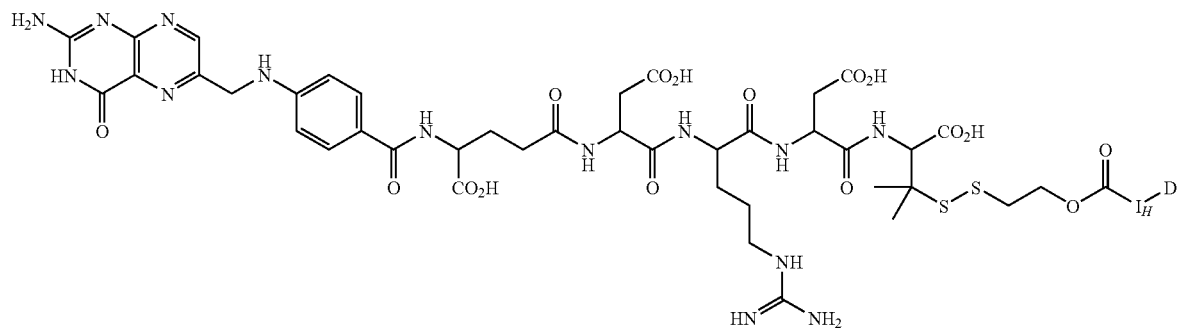
In addition, the following drug delivery conjugates are also illustrative of drug delivery conjugates that are contemplated to fall within the scope of the invention described herein. The accompanying synthetic procedures are illustrative of those that can be used to prepare the drug delivery conjugates described herein.

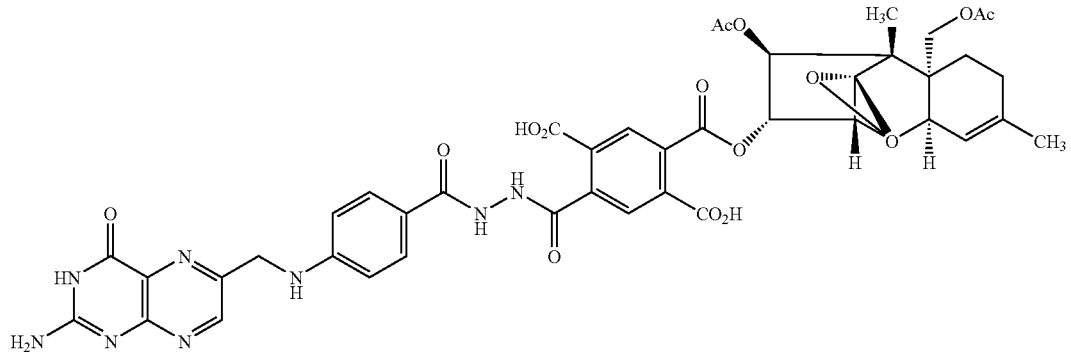

To a solution of diacetoxyscirpenol (DAS) in acetonitrile is added 1.0 eg. of 1,2,4,5-benzenetetracarboxylic dianhydride followed by 1 eg. of Hünig's base. The reaction mixture is stirred for 1.5 hours under argon and at room temperature. If some DAS remains unreacted, an additional 0.2 eg. of dianhydride is added and stirring is continued for 1 hour. A solution of 1.2 eg. of pteroyl hydrazide (prepared according to *J. Am. Chem. Soc.*, 1997, 19, 10004, the disclosure of which is incorporated herein by reference) in anhydrous DMSO is added, followed by 1.0 eg. of Hünig's base. The reaction mixture is stirred for 1 hour and precipitated in diethyl ether. The resulting precipitate is further purified by preparative HPLC.

As generally described in Example 10a. Boc-hydrazide is reacted with succinic anhydride, and the resulting product is reacted with 5"-amino-bis-indolyl-seco-CBI in the presence of EDC as condensing agent. Boc removal and acyl hydrazone formation with free levulinic acid furnishs, after NHS-ester activation, a reactive partner for the peptide fragment Pte-γ-Glu-Asp-Arg-Asp-Dap-OH. This peptide fragment is prepared by a polymer-supported sequential approach using the Fmoc-strategy starting with Fmoc-Dap(Boc)-Wang resin, as generally described in Scheme 12.

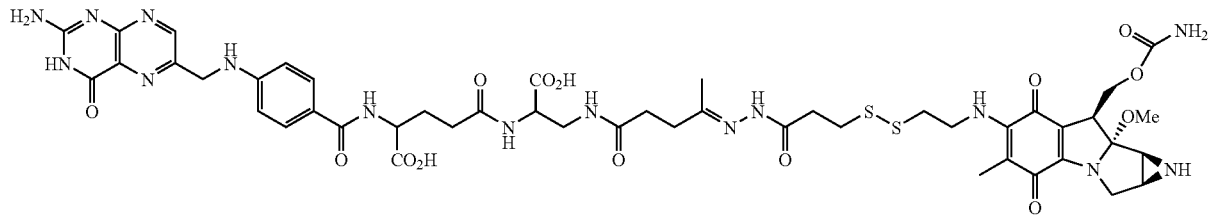

Fmoc-hydrazide is reacted with 3-(2-pyridyldithio)propionic acid to give Fmoc-hydrazido-[3-(2-pyridyldithio)propionate]. Reaction with a mitomycin C derivative (mitomycin C, N-(CH$_2$)$_2$SH) results in a disulfide-containing derivative of mitomycin C. Fmoc-removal using standard protocols and acyl hydrazone formation with levulinic acid provides, after consecutive NHS-ester activation, a reactive partner for the peptide fragment Pte-γ-Glu-Dap-OH, which may be prepared as generally described in Scheme 12.

The following illustrative exemplified embodiments are are not intended and should not be construed as limiting. For example, in each compound presented herein, the stereochemistry of amino acids used in forming the linker may be optionally selected from the natural L configuration, or the unnatural D configuration. Each Example was characterized by NMR, MS, and/or UV spectroscopy, and/or HPLC as indicated; selected characteristic signals are noted as appropriate.

EXAMPLE 1

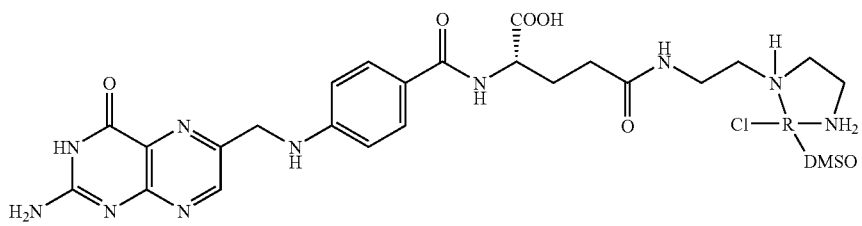

Diethylenetriaminefolic acid, γ-amide (DETA-folate) was synthesized according to a procedure described by P. Fuchs et al., *J. Am. Chem. Soc.*, 1997, 119, 10004, the disclosure of which is incorporated herein by reference. This compound (100 mg) was dissolved in 2 mL of 0.1 N HCl. The resulting solution was added to a solution of K$_2$PtCl$_4$ (158 mg) in 1 mL of 0.1 N HCl with stirring. Three mL of DMSO were added and stirring was continued for 3 days, the solution was filtered, and the filtrate precipitated in acetonitrile to give 170 mg of a yellow powder; MS (MALDI) 1249.92, 1286.27; $^1$H NMR (D$_2$O) δ 1.05 (t, 1H), 2.3 (t, 2H), 3.1 (t, 2H), 4.45 (m, 1H), 6.65 (d, 2H), 7.5 (d, 2H), 8.65 (s, 1H).

EXAMPLE 2a

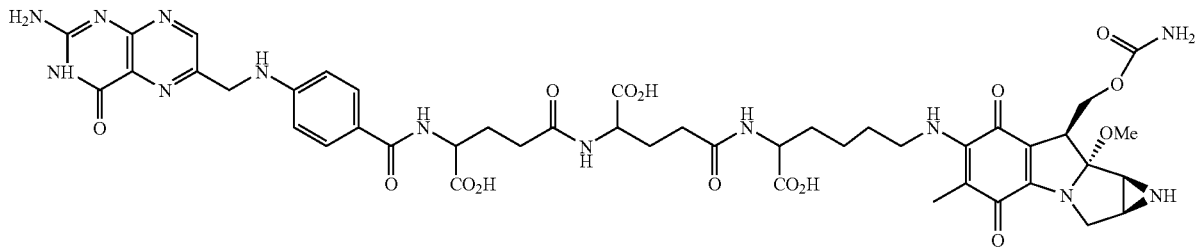

The N[10]-trifluoroacetyl protected folate-containing peptidyl fragment N[10]-TFA-Pte-Glu-Glu-Lys-OH was prepared by a polymer-supported sequential approach using the Fmoc-strategy, as generally illustrated in Scheme 12. It was synthesized on the acid-sensitive Fmoc-Lys(Boc)-Wang resin. PyBop was applied as the activating reagent to ensure efficient coupling using low equivalents of amino acids. Fmoc protecting groups were removed after every coupling step under standard conditions (20% piperidine in DMF). Fmoc-Glu-OtBu and N[10]-TFA-Pte-OH were used as protected amino acid building blocks. After the last assembly step the peptide was cleaved from the polymeric support by treatment with trifluoroacetic acid, ethanedithiol and triisopropylsilane. This reaction also resulted in simultaneous removal of the t-Bu and t-Boc protecting groups. The crude peptide was purified by preparative HPLC to give N[10]-TFA-Pte-γGlu-γGlu-Lys-OH as a TFA salt. A solution of 81 mg (0.1 mmol) of the peptide in 2 mL DMSO was treated with 15 μL (0.11 mmol) Et$_3$N and 35 mg (0.1 mmol) of mitomycin A. Mitomycin A may be prepared from Mitomycin C according to the procedures of M. Matsui, Y. Yamada, K. Uzu, and T. Hirata, *J. Antibiot.* 21, 189-198 (1968) and D. Vias, D. Benigni, R. Partyka, and T. Doyle, *J. Org. Chem.* 51, 4307-4309 (1986), the disclosures of which are incorporated herein by reference. The reaction mixture was stirred for 48 h at room temperature and the solvent removed by freeze-drying. Unless otherwise noted, all evaporations of solvent were conducted under reduced pressure. Finally, the trifluoroacetyl protective group was detached in aqueous ammonium hydroxide (pH=10.0) and the product was precipitated in acetonitrile to give 102 mg of the conjugate as a yellow solid; $^1$H NMR (D$_2$O) δ 2.45 (q, 1H), 2.95 (m, 2H), 3.35 (dd, 1H), 3.5 (d, 1H), 6.5 (d, 2H), 7.55 (d, 2H), 8.55 (s, 1H).

EXAMPLE 2b

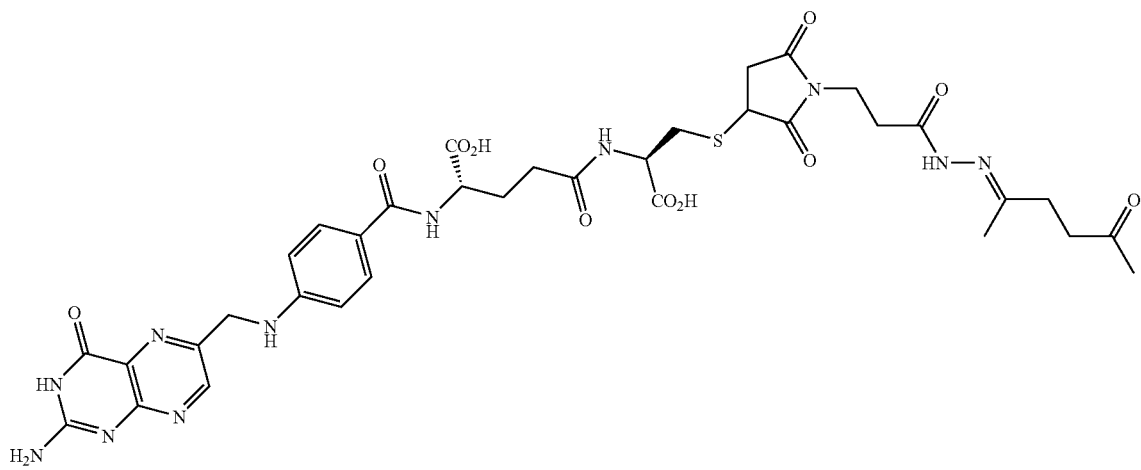

The N[10]-trifluoroacetyl protected folate-containing peptidyl fragment N[10]-TFA-Pte-Glu-Cys-OH was prepared by a polymer-supported sequential approach using the Fmoc-strategy, as generally illustrated in Scheme 12, and described in Example 2a. Cystamine was reacted with mitomycin A (see Matsui et al., *J. Antibiot.* 21, 189-198 (1968); Vias et al., *J. Org Chem.* 51, 4307-4309 (1986)) giving the disulfide containing mitomycin C derivative possessing a terminal free amino group, which was coupled with levulinic acid, followed by subsequent reaction of the carbonyl group with a maleinido derivatized acyl hydrazide. Reaction of the resulting Michael acceptor with N[10]-TFA-Pte-Glu-Cys-OH gave the final conjugate after removal of the trifluoroacetyl protective group with aqueous ammonium hydroxide (pH=10.0), and precipitation from acetonitrile; MS (MALDI) 1059.04, 1148.44, 1225.32, 1300.8; $^1$H NMR (D$_2$O) δ 1.8 (d, 2H), 1.9 (s, 1H), 2.3 (q, 1h), 2.45 (q, 1H), 2.9 (t, 1H), 3.35 (dd, 1H), 4.45 (s, 1H), 4.5 (dd, 1H), 6.65 (d, 2H), 7.55 (d, 2H), 8.6 (s, 1H).

EXAMPLE 3

The intermediate maleimido p-methoxybenzylidene acetal of T-2 toxin was synthesized starting from commercially available N-(2-hydroxyethyl)maleimide. Its hydroxyl group was reacted with p-methoxybenzyl chloride (1.2 eg.) in the presence of silver(I) oxide (2 eg.) as a mild base in methylene chloride. The crude product was purified on a Silica column. Oxidative treatment of the resulting p-methoxybenzyl ether with 1.5 eg. of 2,3-dichloro-5,6-dicyano-benzoquinone (DDQ) in the presence of the OH-containing T-2 toxin (1 eg.) gave the desired p-methoxybenzylidene acetal via the stabilized p-methoxybenzylcarbenium intermediate species.

The other reaction partner, Pte-γ-Glu-Arg-Asp-Cys-OH, was prepared by a polymer-supported sequential approach using the Fmoc-strategy. It was synthesized on the acid-sensitive H-Cys(4-methoxytrityl)-2-chlorotrityl-resin. PyBop was applied as the activating reagent to ensure efficient coupling using low equivalents of amino acids. Fmoc-Asp(OtBu)-OH, Fmoc-Arg(Pbf)-OH, Fmoc-Glu-OtBu), and N[10]-TFA-Pte-OH were used as protected amino acid building blocks. Fmoc protecting groups were removed after every coupling step under standard conditions (20% piperidine in DMF). After the last assembly step the peptide was cleaved from the polymeric support by treatment with trifluoroacetic acid, ethanedithiol and triisopropylsilane. This reaction also resulted in simultaneous removal of the t-Bu and t-Boc protecting groups. The crude peptide was purified by preparative HPLC to give $N^{10}$-TFA-Pte-γ-Glu-Arg-Asp-Cys-OH. The trifluoroacetyl protective group was detached in aqueous ammonium hydroxide (pH=10.0).

Finally, the targeted p-methoxybenzylidene acetal-tethered folate-drug conjugate was prepared by mixing under argon a buffered water solution (pH=7.0) of the peptide with an equimolar acetonitrile solution of the maleimido-containing acetal of T-2 toxin. After stirring at room temperature for 1 hour the final conjugate was subjected to preparative HPLC and gave a yellow powder after freeze-drying of the collected fraction; MS $(m+H)^+$ 1541.3; $^1H$ NMR (DMSO-$d_6$) δ 0.1 (s, 1H), 0.55 (d, 2H), 0.9 (dd, 3H), 1.65 (s, 1H), 2.0 (d, 1H), 3.75 (d, 2H), 5.25 (d, 1H), 6.65 (d, 2H), 6.9 (d, 2H), 7.3 (t, 2H), 7.65 (d, 2H), 8.65 (s, 1H).

EXAMPLE 4a

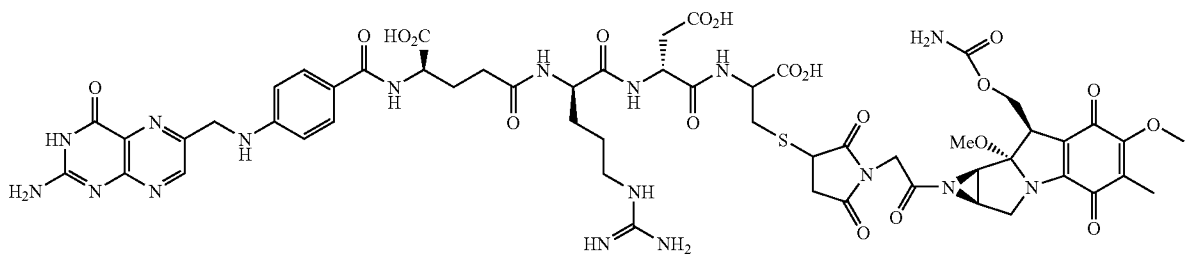

EXAMPLE 4b

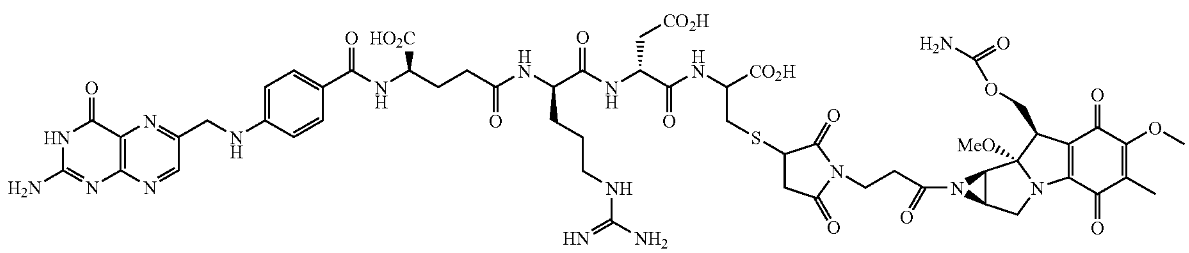

EXAMPLE 4c

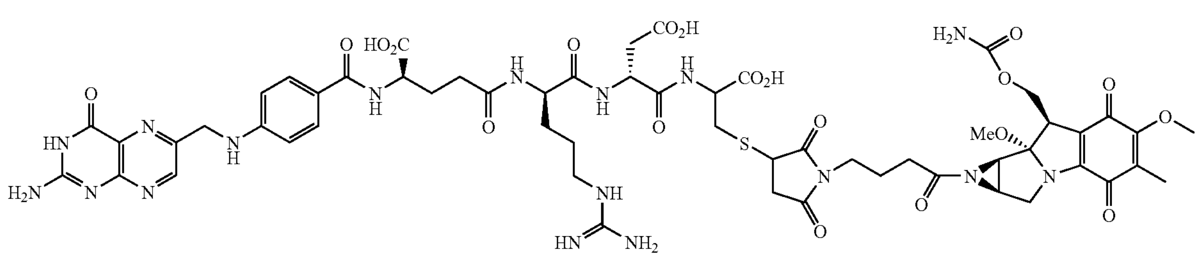

The compounds of Examples 4a, 4b, and 4c were prepared according to the procedure generally described in Example 3, except that the acylaziridine was prepared by acylation (see Scheme 1) of mitomycin A with the appropriate commercially available N-(alkanoic acid)maleimide.

EXAMPLE 5

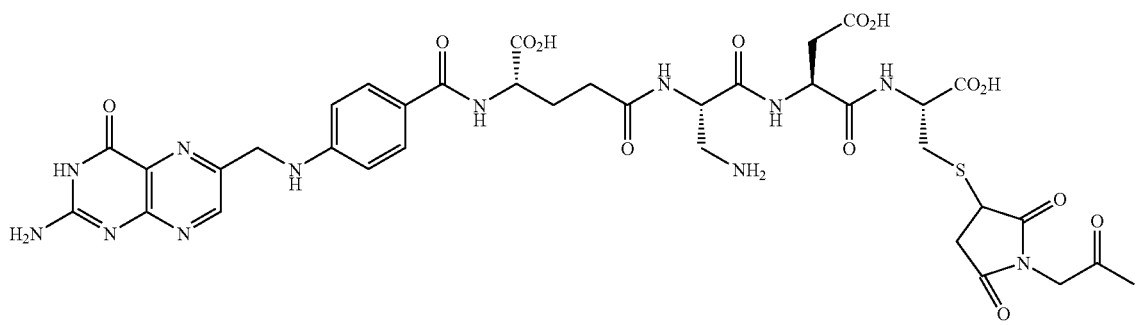

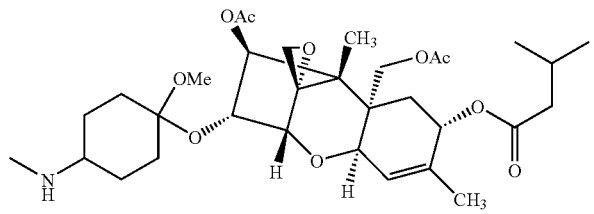

Reaction of trans-4-aminocyclohexanol hydrochloride with an equimolar amount of Fmoc-OSu in the presence of 2.2 eg. of $NaHCO_3$ as a base, and acetonitrile/water (1/1) as a solvent gave N-Fmoc-protected aminoalcohol which was oxidized to the corresponding N-Fmoc-protected aminoketone applying Swern's conditions (*Synthesis*, 1981, 165). Ketalization with 4 eq. of methyl orthoformate and a catalytic amount of trifluoroacetic acid gave an N-Fmoc-protected aminoketal in quantitative yield. Treatment of this ketal with equimolar amounts of trimethylsilyl trifluoromethanesulfonate and 2,4,6-tri-t-butyl-pyridine resulted in 4-Fmoc-aminocyclohexyl enol ether as a product. In the next step, the drug, T-2 toxin, was treated with a four-fold excess of the enol ether in the presence of molecular sieves (3 Å) and catalytic amounts of trifluoroacetic acid. The resulting unsymmetrical mixed ketal was purified on silica. The Fmoc protective group was removed by treatment with resin-bound piperidine in DMF. The liberated amino group was reacted with 1.1 eg. of maleimidoacetic acid-NHS-ester in the presence of 1.1 eg. of Hünig's base. The maleimido-containing ketal of T-2 toxin was purified on silica.

The folate-containing peptide fragment, Pte-γ-Glu-β-Dap-Asp-Cys-OH, was prepared by a polymer-supported sequential approach using the Fmoc-strategy, as generally described in Scheme 12. It was synthesized on the acid-sensitive Wang resin loaded with Fmoc-L-Cys(Trt)-OH. PyBop was applied as the activating reagent to ensure efficient coupling using low equivalents of amino acids. Fmoc protecting groups were removed after every coupling step under standard conditions (20% piperidine in DMF). Fmoc-Asp(OtBu)-OH, Boc-Dap (Fmoc)-OH, Fmoc-Glu-OtBu, and $N^{10}$-TFA-Pte-OH were used as protected amino acid building blocks. After the last assembly step the peptide was cleaved from the polymeric support by treatment with trifluoroacetic acid, ethanedithiol and triisopropylsilane. This reaction also resulted in simultaneous removal of the t-Bu, t-Boc, and trityl protecting groups. Finally, the trifluoroacetyl moiety was detached in aqueous ammonium hydroxide to give the desired thiol-containing peptide. The crude peptide was purified by preparative HPLC.

Finally, the targeted ketal-tethered folate-drug conjugate was prepared by mixing under argon buffered water solution (pH=7.0) the peptide with an equimolar acetonitrile solution of the maleimido-containing ketal of T-2 toxin. After stirring at room temperature for 1 hour the final conjugate was subjected to preparative HPLC and gave a yellow powder after freeze-drying of the collected fraction; ES MS $(m-H)^-$ 1474.5, $(m+H)^+$ 1476.2, $(m+Na)^+$ 1498.3.

EXAMPLE 6

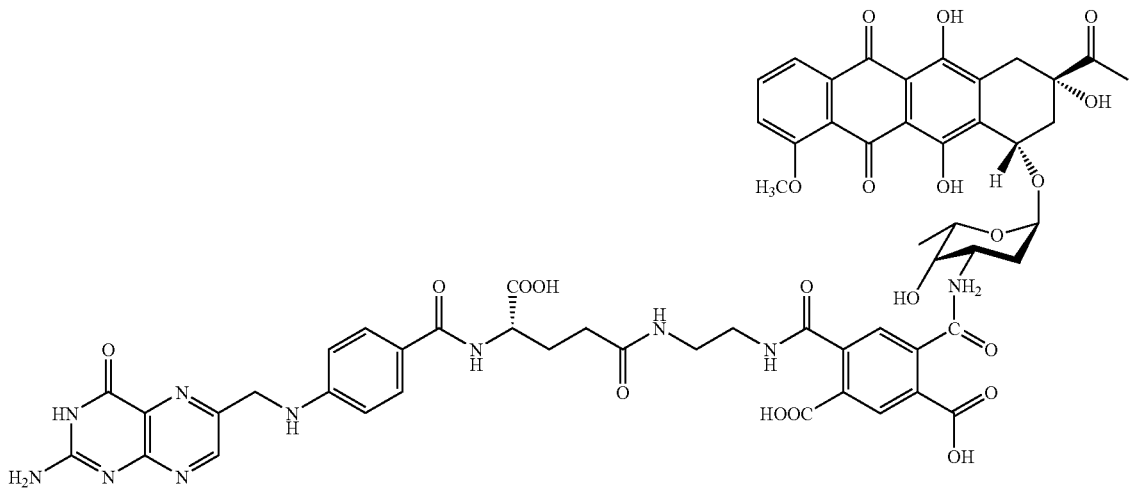

Ethylenediaminefolic acid, γ-amide (EDA-folate) was synthesized according to a procedure described by P. Fuchs et al. (*J. Am. Chem. Soc.*, 1997, 119, 10004; see e.g. synthesis of compound 52 described therein), the disclosure of which is incorporated herein by reference. EDA-folate (600 mg) was suspended in 5 mL of anhydrous DMSO. After stirring for 4 hours at 60° C. the resulting solution was cooled to 20° C. and 4 eg. of 1,2,4,5-benzenetetracarboxylic dianhydride (BTCA anhydride) was added. After 5 min the reaction-mixture was poured into well-stirred anhydrous acetonitrile. The resulting precipitate was isolated by centrifugation to give 657 mg of BTCA(monoanhydride)-EDA-folate.

To a well-stirred solution of daunomycin in dry DMSO was added solid BTCA(monoanhydride)-EDA-folate (1.5 eg.). After stirring for an additional 14 hours, 50% of the daunomycin remained unreacted (HPLC), and 1.5 eg. of BTCA (monoanhydride)-EDA-folate were then added. After stirring for and additional four hours all of the daunomycin was consumed. In the HPLC profile two new peaks were observed with close retention times representing the two regioisomers of the final conjugate. The crude product was isolated after precipitation in acetonitrile and was further purified on reverse phase HPLC. The structure of the product was in agreement with the ES MS (m–H)⁻ 1227.1.

EXAMPLE 7

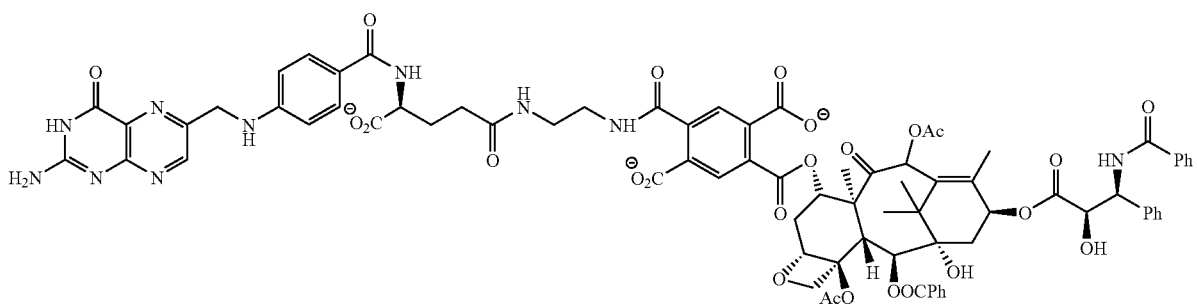

Under argon and at 0° C. to a well-stirred solution of 250 mg (0.25 mmol) of paclitaxel and 130 µL (0.73 mmol) of Hünig's base in 4 mL of anhydrous dichloromethane were added slowly 85 µL (0.8 mmol) Alloc-Cl. The stirring was continued for an additional 12 hours and the product was isolated using standard extraction techniques. This white powder, 2'-alloc-paclitaxel, was used in the next step without further purification.

In this step, 108 mg (0.117 mmol) of 2'-alloc-paclitaxel were dissolved in 1.0 mL of anhydrous acetonitrile. Under argon with stirring, 25 mg (0.117 mmol) of 1,2,4,5-benzene-tetracarboxylic dianhydride (BTCA anhydride) and 21 µL (0.120 mmol) of Hünig's base were added to this solution.

The stirring was continued for an additional 2.5 hours. In a separate reaction flask 52 mg of EDA-folate were stirred at 60° C. until all material was dissolved (ca. 60 min). After cooling to room temperature, the previous reaction mixture was added to this solution and stirring was continued for an additional 2 hours. The reaction mixture was added drop-wise to a well-stirred mixture of acetonitrile/diethyl ether (20:80). The yellow precititate was separated by centrifugation and further purified by preparative HPLC. The structure of the product was in agreement with the 1D and 2D (COSY) $^1$H-NMR spectra; ES MS (m+H)$^+$ 1555.5.

EXAMPLE 8

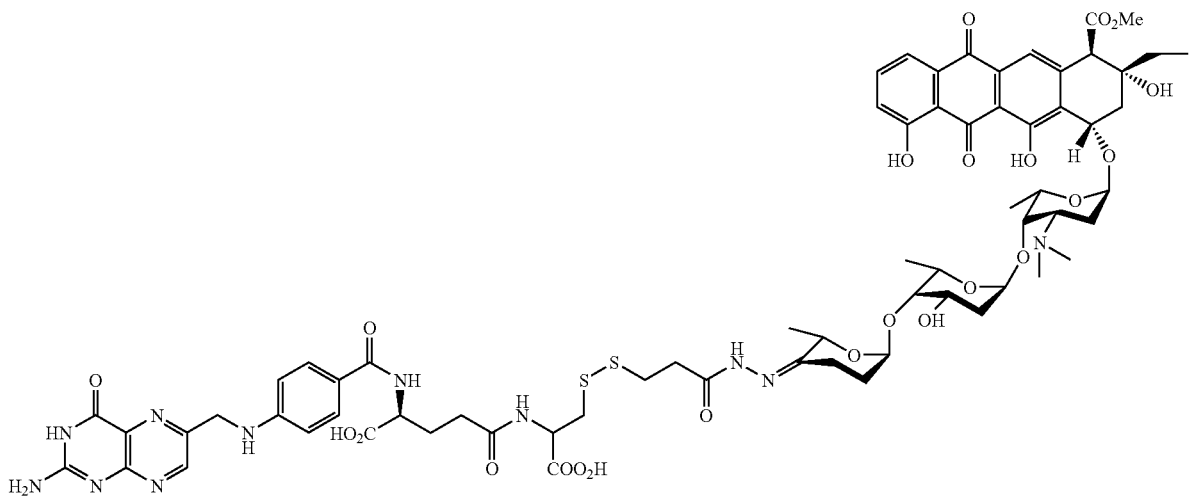

A mixture of 1.0 eg. of aclamycin, 2.0 eg. of hydrazido-[3-(2-pyridyldithio)propionate] (SPDP-hydrazone) and a few crystals of pyridinium p-toluenesulfonate were dissolved under argon with stirring in anhydrous methanol. The reaction mixture was stirred at room temperature for 8 hours. The solvent was evaporated to dryness. The residue was purified on a silica column pretreated with 1.5% triethylamine in chloroform/methanol (90:10). The aclamycin acyl hydrazone obtained was dissolved in a minimal amount of acetonitrile. To the resulting solution was added slowly and under argon an equimolar amount of Pte-γ-Glu-Cys-OH (dissolved in water and adjusted to pH=6.8). The preparation of Pte-γ-Glu-Cys-OH is analogous to the procedure described in Example 2a, and generally described in Scheme 12. The disulfide exchange reaction took place in 10 min. The reaction mixture was added slowly to an excess of acetonitrile and the resulting precipitate was isolated after centrifugation. The precipitate was resuspended once more in acetonitrile and after stirring for 15 min was separated by centrifugation. After drying under high vacuum over night the final conjugate was sufficiently pure (HPLC); ES MS (m+H)$^+$ 1474.1.

EXAMPLE 9

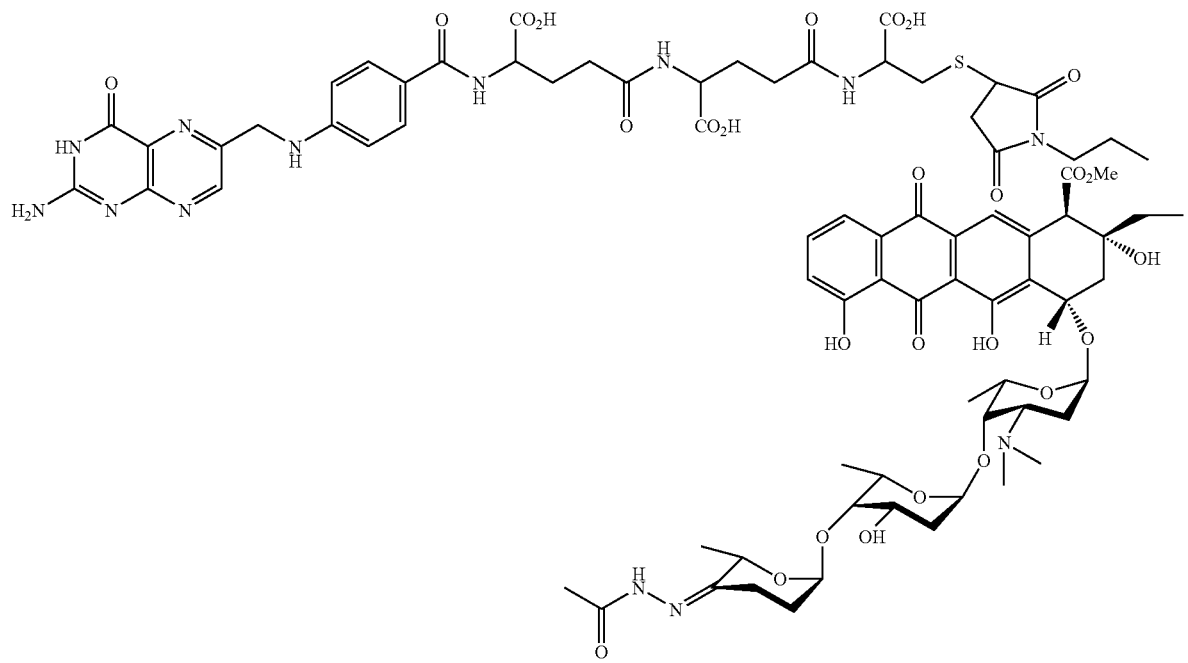

A mixture of 1.0 eg. of aclamycin and 1.2 eg. of β-maleimidopropionic acid.TFA was dissolved under argon with stirring in anhydrous methanol. The reaction mixture was stirred at room temperature for 1 hour. The solvent was evaporated to dryness. The residue was passed through a short silica column pretreated with 1.5% triethylamine in chloroform/methanol (90:10). In a separate flask, the peptide fragment Pte-γ-Glu-γ-Glu Cys-OH was dissolved in water under argon while adjusting the pH to 6.8. The preparation of Pte-γ-Glu-γ-Glu-Cys-OH is analogous to the procedure described in Example 2a, and generally described in Scheme 12. To the resulting yellowish solution was added slowly the maleimido-hydrazone of aclamycin dissolved in a minimal amount of methanol. The reaction mixture was stirred for 1 hour under argon. The methanol was removed and the residue purified by HPLC on a preparative column, followed by freeze-drying; ES MS (m+H)+ 1722.3.

EXAMPLE 9b

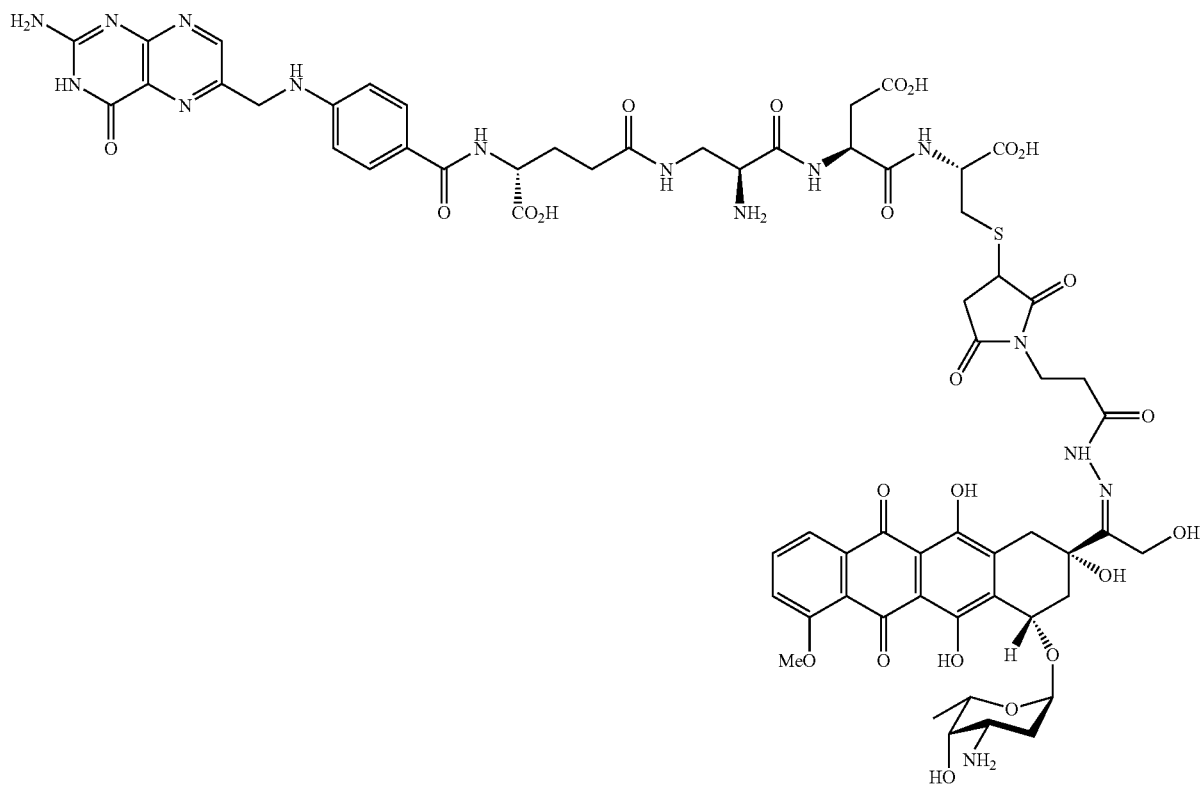

EXAMPLE 9c
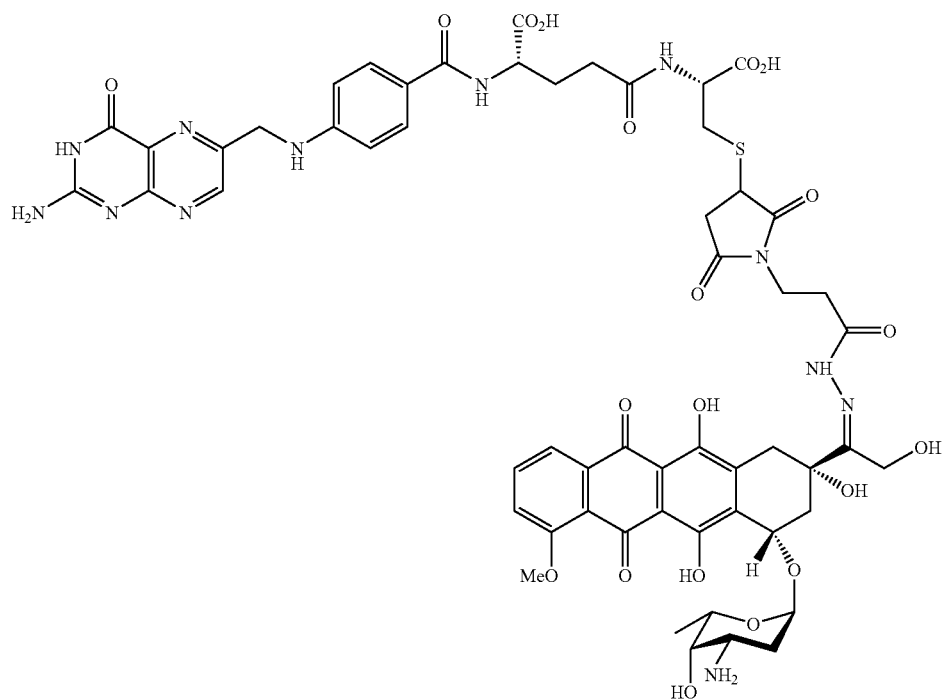
The compounds of Examples 9b and 9c were prepared from doxorubicin (14-hydroxydaunomycin) derivatives according to the procedure generally described in Example 9a.
EXAMPLE 10a
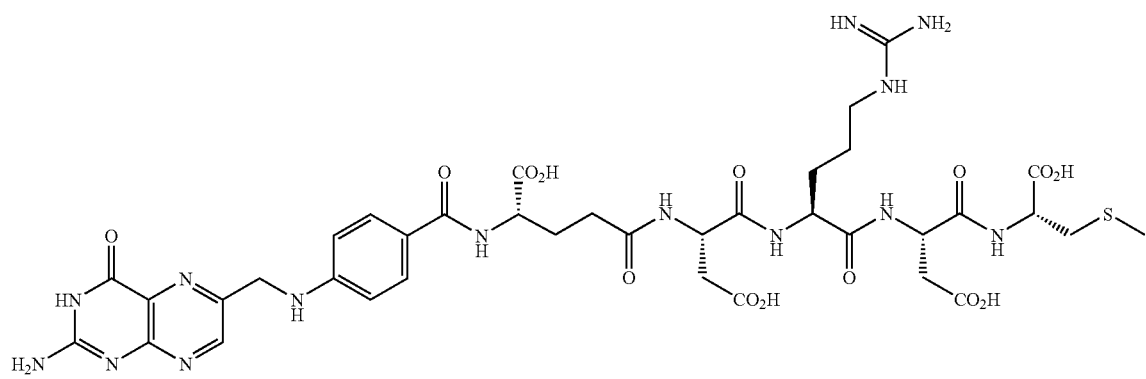

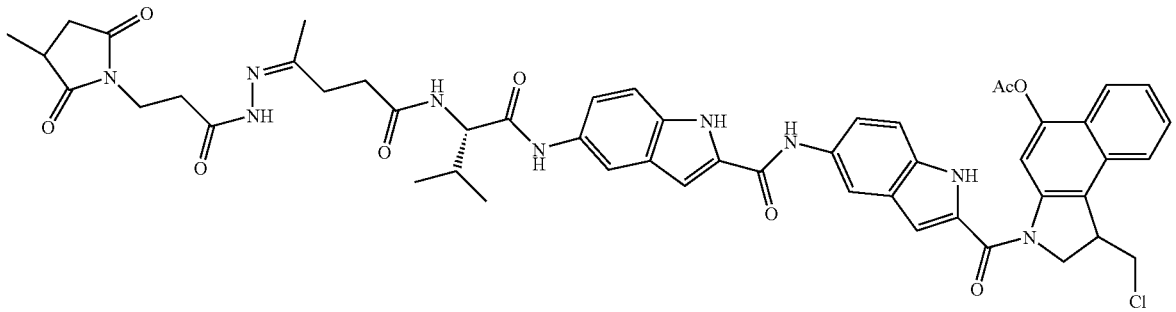

The 5"-(N-Boc)amino analog of the highly potent cytotoxic drug bis-indolyl-seco-1,2,9,9a-tetrahydrocyclopropa[c]benz[e]indol-4-one (bis-indolyl-seco-CBI) was prepared according to a slightly modified procedure described first by D. Boger et al., *J. Org. Chem.*, 1992, 57, 2873, the disclosure of which is incorporated herein by reference.

The peptide fragment, Pte-γ-Glu-Asp-Arg-Asp-Cys-OH, was prepared by a polymer-supported sequential approach using the Fmoc-strategy on the acid-sensitive H-Cys(4-methoxytrityl)-2-chlorotrityl-resin, as generally described in Scheme 12. PyBop was applied as the activating reagent to ensure efficient coupling using low equivalents of amino acids. Fmoc-Asp(OtBu)-OH, Fmoc-Arg(Pbf)-OH, Fmoc-Glu-OtBu), and $N^{10}$-TFA-Pte-OH were used as protected amino acid building blocks. Fmoc protecting groups were removed after every coupling step under standard conditions (20% piperidine in DMF). After the last assembly step the peptide was cleaved from the polymeric support by treatment with trifluoroacetic acid, ethanedithiol and triisopropylsilane. This reaction also resulted in simultaneous removal of the t-Bu and t-Boc protecting groups. The crude peptide was purified by preparative HPLC to give $N^{10}$-TFA-Pte-γ-Glu-Asp-Arg-Asp-Cys-OH. The trifluoroacetyl protective group was detached in aqueous ammonium hydroxide (pH=10.0).

Lev-Val-OH was synthesized using a standard protocol including condensation of valine methyl ester hydrochloride with levolinic acid in the presence of EDC and Hünig's base followed by hydrolysis of the methyl ester with lithium hydroxide and water.

The final assembly of the complex conjugate started with the removal of the N-Boc group from 5"-(N-Boc)amino-bis-indolyl-seco-CBI and coupling of the liberated amino group with the carboxy functionality of Lev-Val-OH in the presence of EDC. Acyl hydrazone formation was accomplished by the reaction of the ketone functionality of the levolinic moiety with 1.2 eg. of β-maleimidopropionic acid.TFA in tetrahydrofuran. After chromatographic purification (silica, TBF/hexane=1/1) the product of the above reaction was dissolved in DMSO. To this solution under argon was added 0.9 eg. of Pte-γ-Glu-Asp-Arg-Asp-Cys-OH and the reaction mixture was stirred for 18 hours. The solvent was removed by freeze-drying and the residue was purified by HPLC.

EXAMPLE 10b

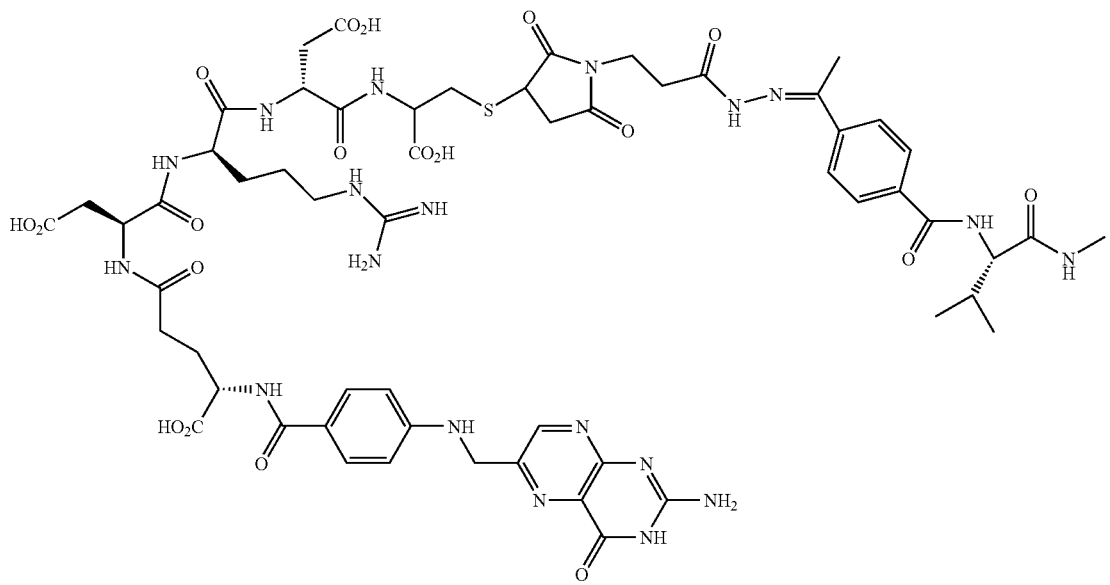

-continued
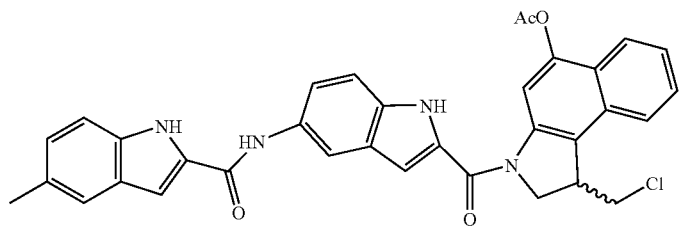
EXAMPLE 10c
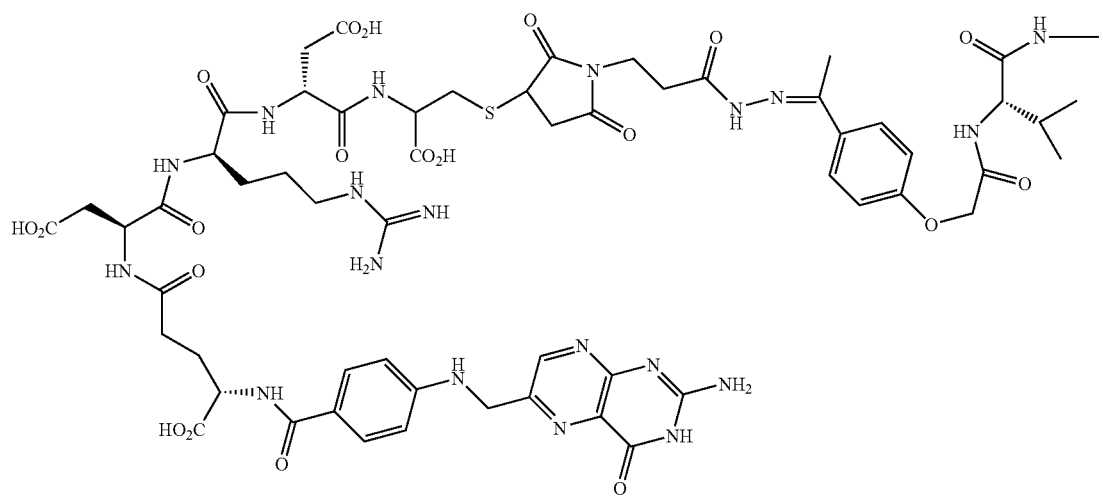
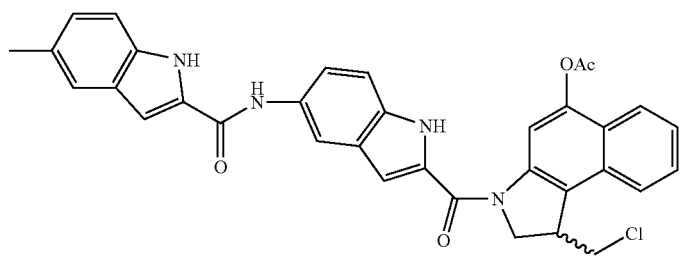
The compounds of Examples 10c and 10c were prepared from derivatives of 5"-(N-Boc)amino-bis-indolyl-seco-CBI according to the procedure generally described in Example 10a.

EXAMPLE 11

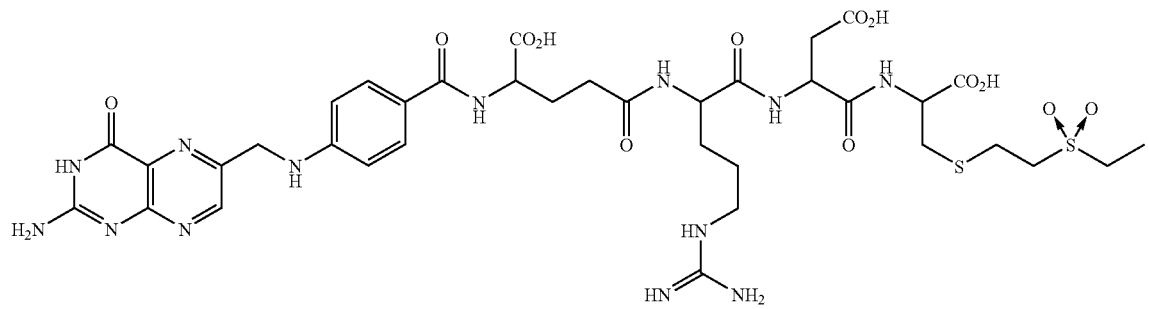

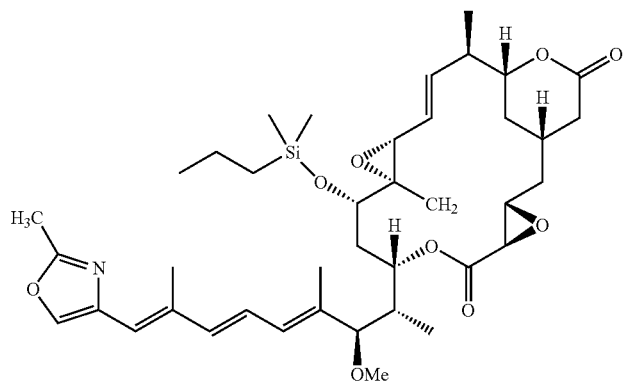

In the presence of potassium carbonate, S-alkylation of 2-mercaptoethanol was accomplished with allyl bromide. The hydroxyl group in the resulting allyl β-hydroxyethyl sulfide was exchanged for chlorine with thionyl chloride. Oxidation of this product with hydrogen peroxide in the presence of acetic acid and acetic anhydride (*J. Am. Chem. Soc.*, 1950, 72, 59, the disclosure of which is incorporated herein by reference) resulted in allyl β-chloroethyl sulfone. Reaction of this product with chlorodimethylsilane in the presence of a catalytic amount of hydrogen hexachloroplatinate(IV) and with elevated temperature gave 3-(β-chloroethyl sulfonyl) propyl dimethylsilyl chloride after distillation. This chlorosilane silylated the hydroxyl group of the highly cytotoxic compound rhizoxin while using 1 eg. of pyridine as a base. Treatment of the β-chloroethyl sulfone moiety in this molecule with excess of triethylamine resulted in a smooth β-elimination of hydrogen chloride with formation of the respective vinyl sulfone.

The other reaction partner, the peptide fragment Pte-γ-Glu-Arg-Asp-Cys-OH, was prepared by a polymer-supported sequential approach using an Fmoc protocol, as generally described in Example 2a and Scheme 12.

The final assembly of the complex conjugate was achieved by Michael addition of the thiol group of the peptide fragment to the vinyl sulfone moiety of the silicon linker attached to rhizoxin. Reaction medium for this transformation was 50:50 acetonitrile/water (pH=7.2). After stirring at room temperature for 24 hours, the final conjugate was isolated after HPLC on a preparative column; ES MS $(m+H)^+$ 1631.6; $(m-H)^-$ 1629.6.

EXAMPLE 12

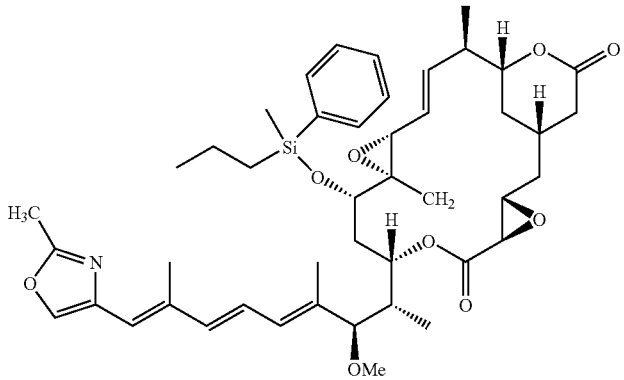

This silicon-tethered conjugate of rhizoxin was synthesized using the protocol described in Example 11, except that commercially available chloromethylphenylsilane was used instead of chlorodimethylsilane.

EXAMPLE 13

General Preparation of Compounds Containing a Cysteine Disulfide Bond

Thiosulfonates 4 (1 eq.), prepared according to the method of Ranasinghe and Fuchs, *Synth. Commun.* 18(3), 227-32 (1988), the disclosure of which is incorporated herein by reference, are reacted with drugs, drug analogs, or drug derivatives 5 (1 eq.) to prepare the drug thiosulfonates 6 as a solution in methanol, as shown in Scheme 13. R is alkyl or aryl, L is a suitable leaving group, such as halogen, pentafluorophenyl, and the like, n is an integer from 1 to 4, and X is —O—, —NH—, —C(O)O—, or —C(O)NH—. Conversion is conveniently monitored by observing the disappearance of each starting material by TLC (silica gel; $CHCl_3/MeOH=9/1$).

Scheme 13

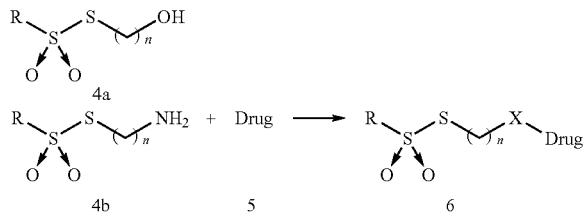

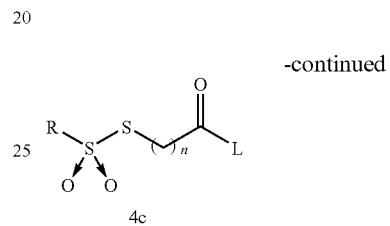

The folate-containing peptidyl fragment Pte-Glu-$(AA)_n$-Cys-OH (9) is prepared by a polymer-supported sequential approach using the Fmoc-strategy on an acid-sensitive Fmoc-Cys(Trt)-Wang resin (7), as shown in Scheme 14. $R_1$ is Fmoc, $R_2$ is Trityl, and DIPEA is diisopropylethylamine. PyBop is applied as the activating reagent to ensure efficient coupling. Fmoc-protecting groups are removed after each coupling step under standard conditions. Appropriately protected amino acid building blocks, such as Fmoc-Glu-OtBu, $N^{10}$-TFA-Pte-OH, and the like, are used, as described in Scheme 14, and represented by in step (b) by Fmoc-AA-OH. Thus, AA refers to any amino acid starting material, that is appropriatedly protected. The coupling sequence (steps (a) & (b)) involving Fmoc-AA-OH is performed "n" times to prepare solid-supported peptide 8, where n is an integer and may equal 0 to about 100. Following the last coupling step, the remaining Fmoc group is removed, and the peptide is sequentially coupled to a glutamate derivative (step (c)), deprotected, and coupled to TFA-protected pteroic acid (step (d)). Subsequently, the peptide is cleaved from the polymeric support upon treatment with trifluoroacetic acid, ethanedithiol, and triisopropylsilane (step (e)). These reaction conditions result in the simultaneous removal of the t-Bu, t-Boc, and Trt protecting groups. The TFA protecting group is removed upon treatment with base (step (f)) to provide the folate-containing Cys-containing peptidyl fragment 9.

Scheme 14

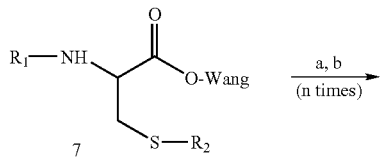

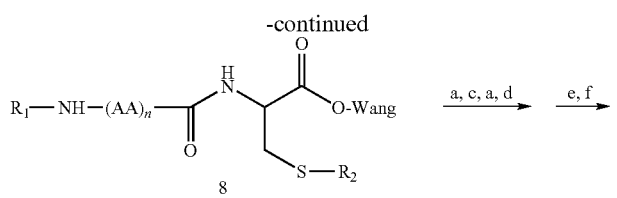

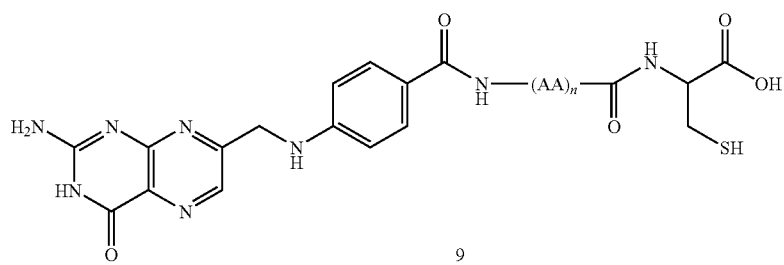

a 20% piperidine/DMF;
b Fmoc-AA-OH, PyBop, DIPEA, DMF;
c Fmoc-Glu(O-t-Bu)──OH; PyBop, DIPEA, DMF;
d 1. $N^{10}$ (TFA)-Pte-OH; PyBop, DIPEA, DMSO;
e TFAA, $(CH_2SH)_2$, i-$Pr_3SiH$;
f $NH_4OH$, pH 10.3.

Drug conjugates are prepared by reacting folate derivative 9 (0.9-0.95 eq.) with drug thiosulfonate 6 in deionized water (0.04 M, pH adjusted to 7 with 0.1 N $NaHCO_3$) under argon for about 30 minutes, forming a disulfide bond. Upon evaporation of the methanol in vacuo, the conjugate may be purified by preparative HPLC (Prep Novapak HR C18 19×300 mM column; mobile phase (A)—1.0 mM phosphate buffer, pH=6; organic phase (B)—acetonitrile; conditions-gradient from 99% A and 1% B to 50% A and 50% B in 30 minutes, flow rate=15 mL/minute).

EXAMPLE 14a

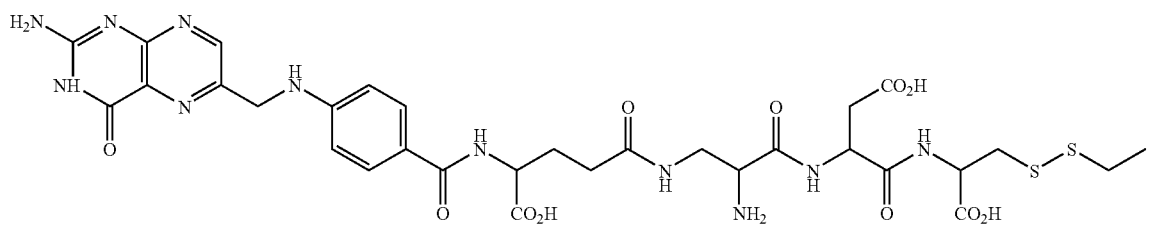

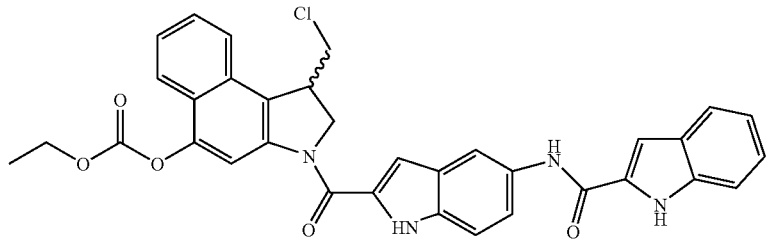

$^1$H NMR (DMSO-$d_6$) δ 4.7 (d, 1H), 4.95 (t, 1H), 6.7 (d, 4H), 6.9 (t, 1H), 7.95 (d, 2H), 8.1 (d, 2H), 8.2 (m, 1H), 8.3 (s, 1H), 8.4 (s, 1H), 8.7 (s, 1H), 10.2 (s, 1H), 11.8 (d, 2H).

EXAMPLE 14b
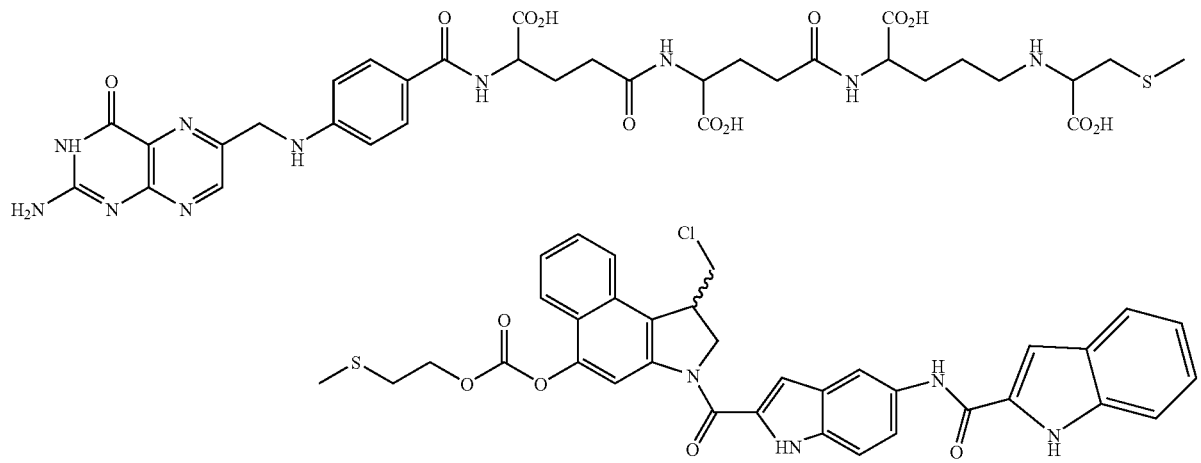
ES MS (m−H)⁻ 1436.4, (m+H)⁺ 1438.3.
EXAMPLE 14c
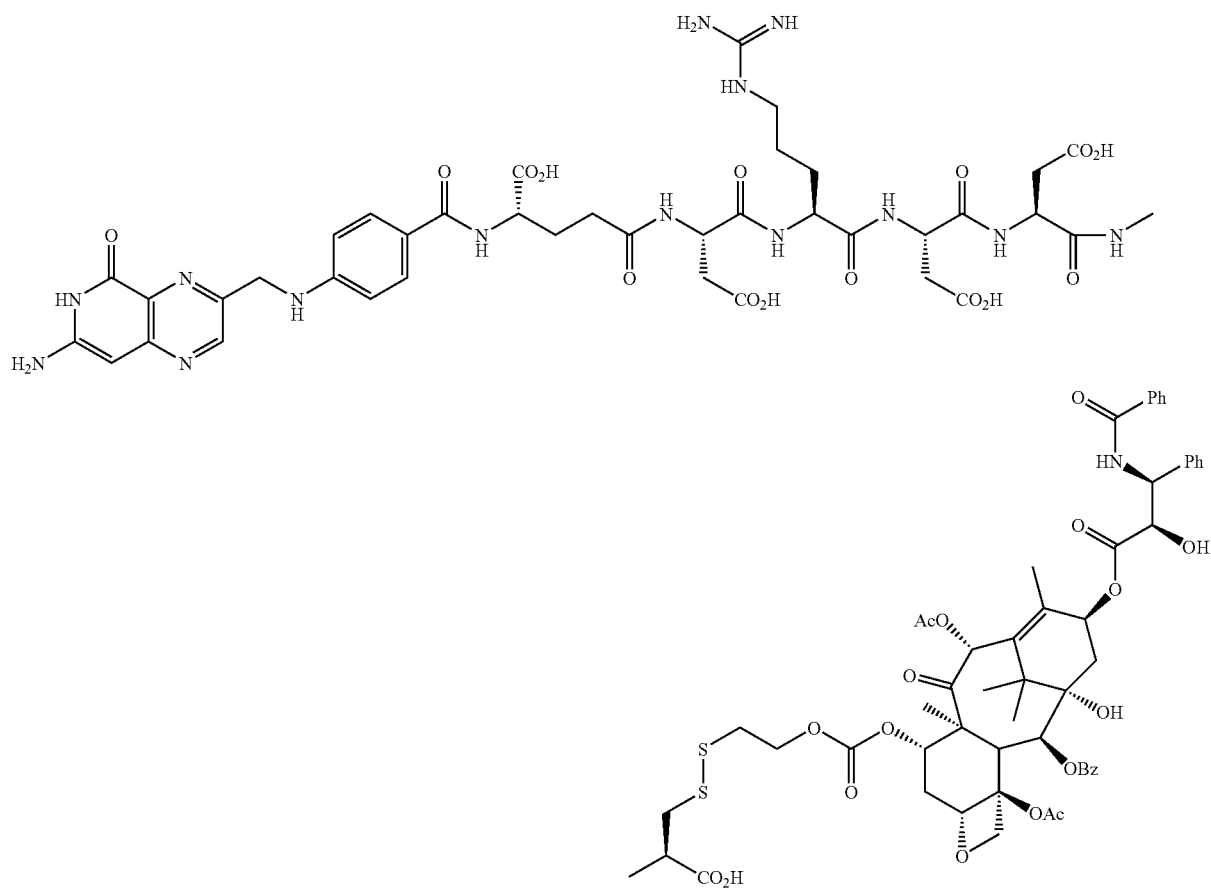

¹H NMR DMSO-d₆/D₂O) δ 1.0 (s, 1H), 1.1 (s, 1H), 1.6 (s, 1H), 1.8 (s, 1H), 2.1 (s, 1H), 2.25 (s, 3H), 2.65 (dd, 2H), 3.7 (d, 1H), 4.4 (t, 1H), 4.55 (q, 2H), 4.6 (d, 2H), 4.95 (d, 1H), 5.9 (t, 1H), 6.15 (s, 1H), 6.6 (d, 2H), 7.85 (d, 2H), 7.95 (d, 2H), 8.6 (s, 1H), 8.95 (d, 1H).
EXAMPLE 14d
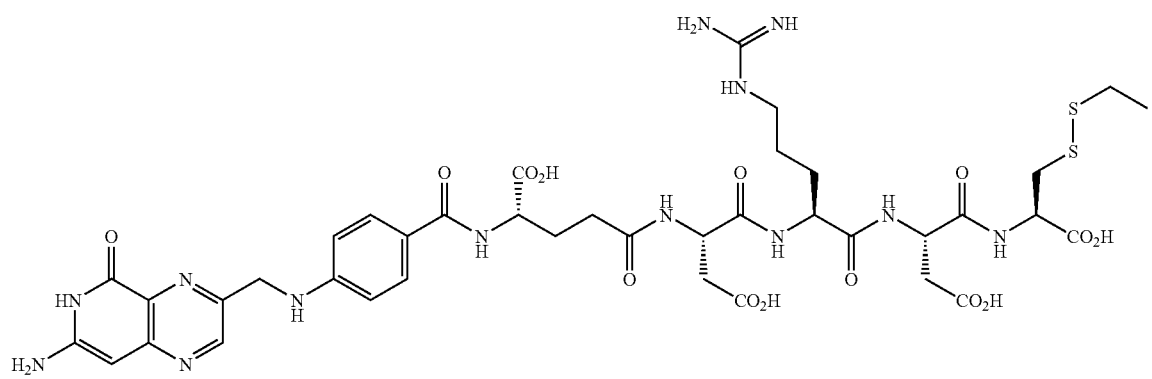
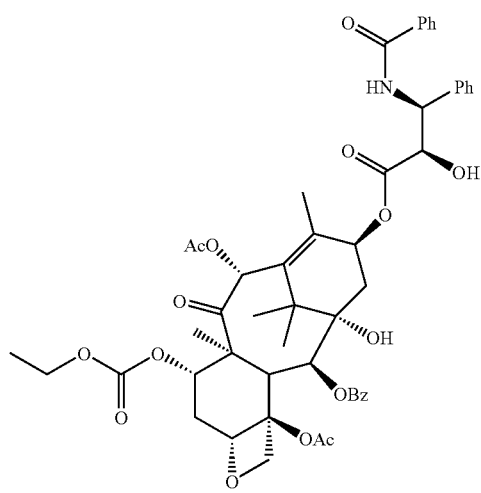
¹H NMR (DMSO-d₆/D₂O) δ 1.0 (s, 1H), 1.1 (s, 1H), 1.65 (s, 1H), 2.1 (s, 1H), 2.25 (s, 3H), 2.6 (dd, 2H), 3.25 (dd, 1H), 3.6 (t, 2H), 3.7 (d, 1H), 4.4 (t, 1H), 4.6 (d, 1H), 4.95 (d, 1H), 5.9 (t, 1H), 6.2 (s, 1H), 6.6 (d, 2H), 7.7 (t, 1H), 7.9 (d, 2H), 7.95 (d, 2H), 8.6 (s, 1H), 9.1 (d, 2H).

EXAMPLE 14e

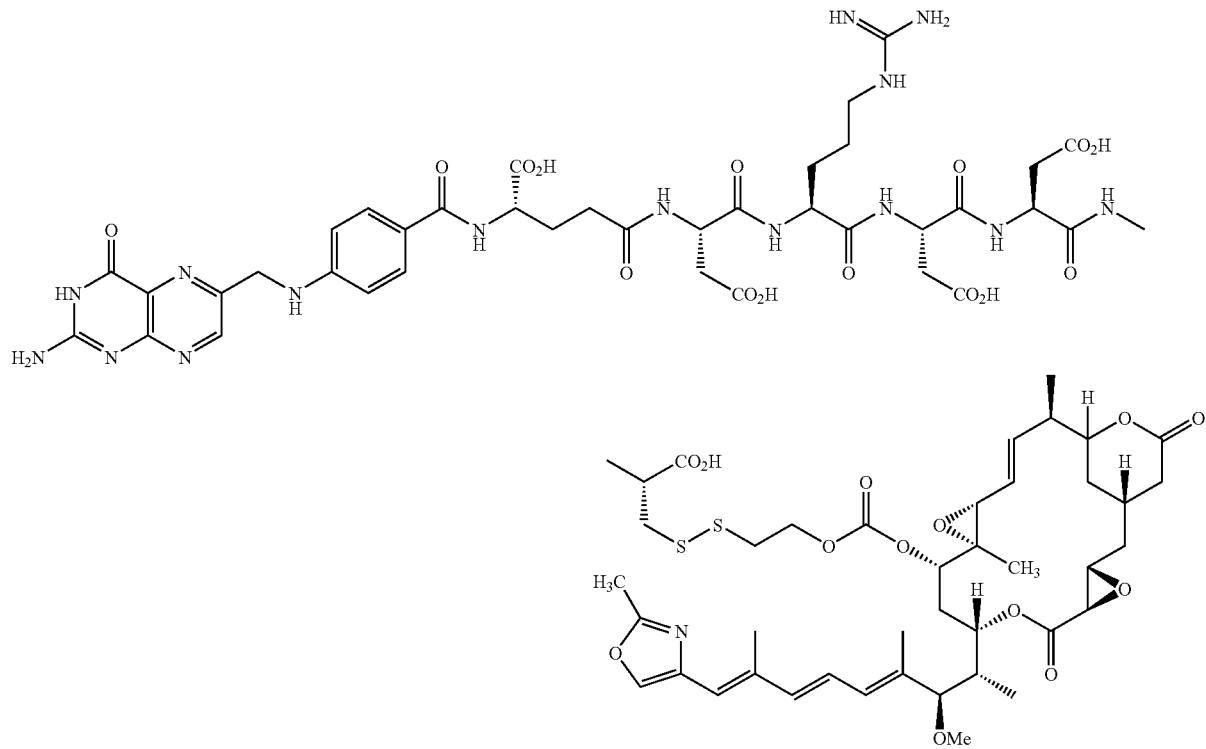

$^1$H NMR (DMSO-d$_6$/D$_2$O) δ 10.85 (d, 2H), 1.05 (d, 2H), 1.2 (d, 2H), 1.7 (d, 2H), 3.95 (d, 1H), 4.05 (dd, 1H), 5.4 (dd, 1H), 5.7 (dd, 1H), 6.65 (d, 2H), 7.6 (d, 2H), 7.95 (s, 1H), 8.65 (s, 1H).

EXAMPLE 14f

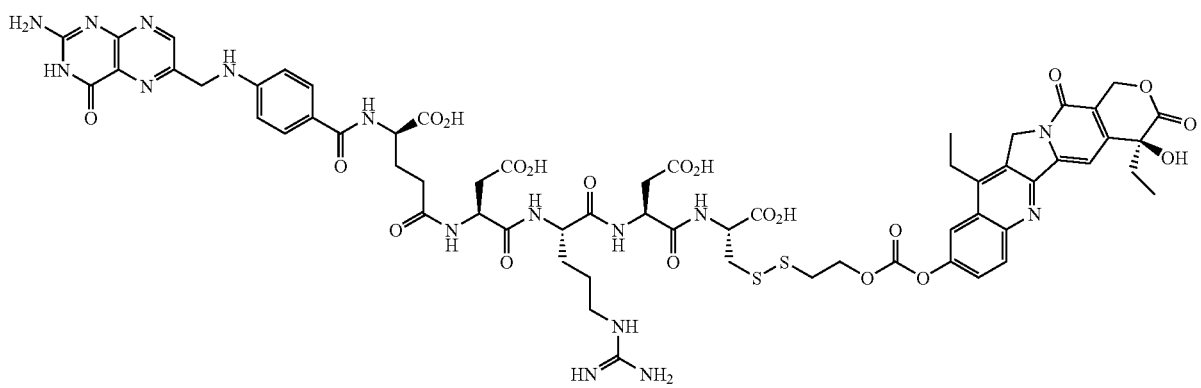

ES MS (m+H)$^+$ 1487.23; $^1$H NMR (DMSO-d$_6$/D$_2$O) δ 0.9 (t, 2H), 1.3 (t, 2H), 2.15 (t, 2H), 3.2 (dd, 1H), 4.0 (t, 1H), 4.15 (q, 1H), 5.3 (s, 2H), 5.5 (s, 2H), 6.6 (d, 2H), 7.0 (s, 1H), 7.4 (m, 2H), 7.55 (d, 2H), 8.0 (d, 2H), 8.6 (s, 1H).

Examples 14a, 14b, 14c, 14d, 14e, and 14f were prepared by the following general procedure. To a well stirred solution of the corresponding drug having an —OH group (1 eq. in dry CH$_2$Cl$_2$ or dry THF) was added under argon 6-(trifluoromethyl)benzotriazolyl 2-(2'-pyridyldithioethyl carbonate (1.3 eq.) and NN-dimethylaminopyridine (1.5 eq.). The reaction mixture was stirred for 3 h, and the pyridyldithio-derivatized drug was isolated by silica chromatography (>65% for each example). The correpsonding peptidyl fragment (0.5 eq.), prepared according to the general approach outlined in Scheme 12, was dissolved in DMSO. To the resulting clear yellow solution was added the pyridyl-dithio derivatized drug. After 30 min, the reaction was completed and the conjugate purified by HPLC. In the case of Example 14e, the peptidyl fragment Pte-Glu-Asp-Arg-Asp-Asp-Cys-OH was first dissolved in water, and the pH of the solution was adjusted to 2.5 with 0.1 N HCl, causing the peptidyl fragment to precipitate. The peptidyl fragment was collected by centrifugation, dried, and dissolved in DMSO for subsequent reaction with the pyridyldithio-derivatized drug.

EXAMPLE 15

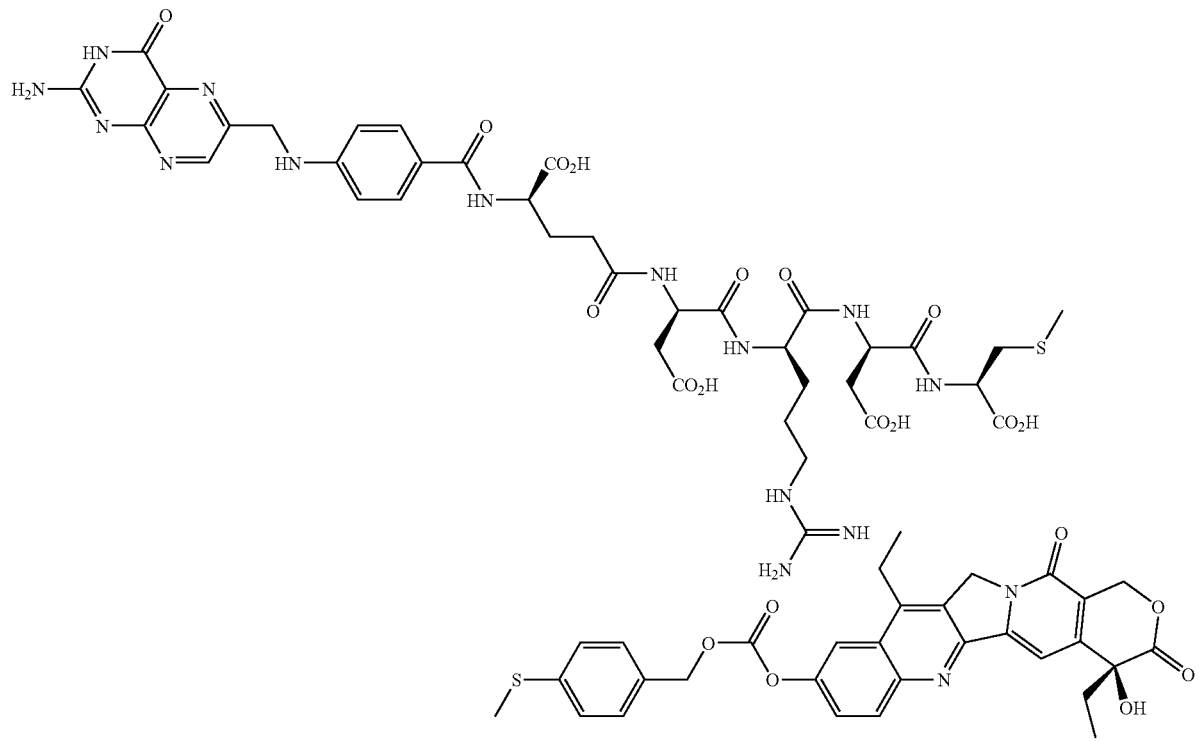

The intermediate 4-(2-pyridinyldithio)benzylcarbonate of SN 38 (10-hydroxy-7-ethylcamptothecin) was prepared according to the procedure described by P. Senter et al., *J. Org. Chem.* 1990, 55, 2875, the disclosure of which is incorporated herein by reference. The peptidyl fragmant Pte-Glu-Asp-Arg-Asp-Cys-OH was dissolved in DMSO, and to the resulting clear yellow solution was added the pyridyldithio derivatized drug. After 30 min, the reaction was completed and the conjugate purified by HPLC; ES MS $(m+H)^+$ 1425.38; $^1$H NMR (DMSO-$d_6$/$D_2$O) δ 0.9 (t), 1.15 (t), 3.9 (t), 4.0 (t), 4.25 (t), 5.1 (m), 5.2 (s), 5.4 (s), 6.55 (d), 7.25 (d), 7.35 (d), 7.5 (d), 7.9 (d), 8.55 (s).

EXAMPLE 16a

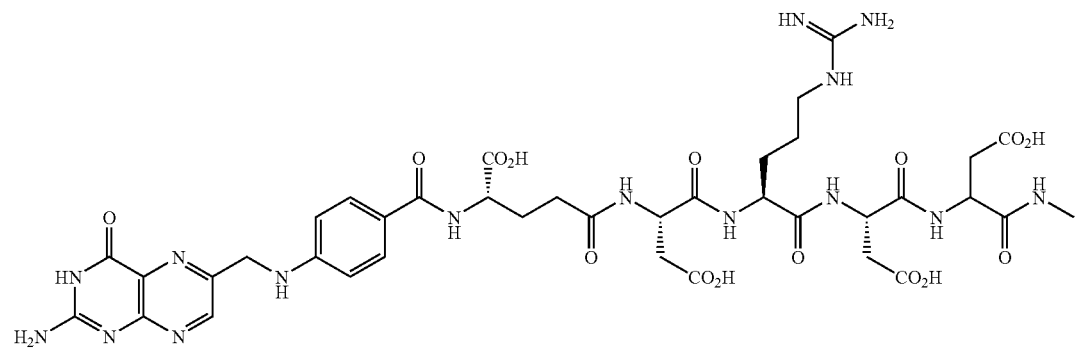

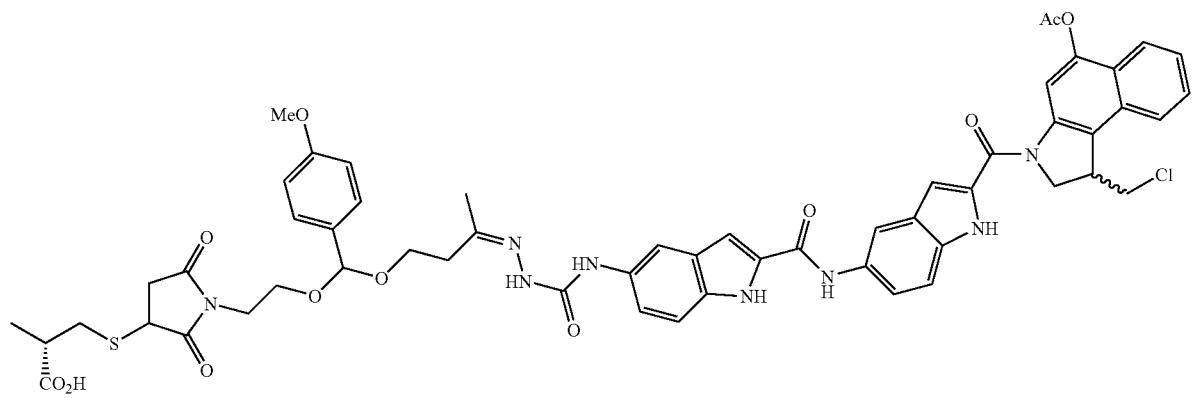

EXAMPLE 16b

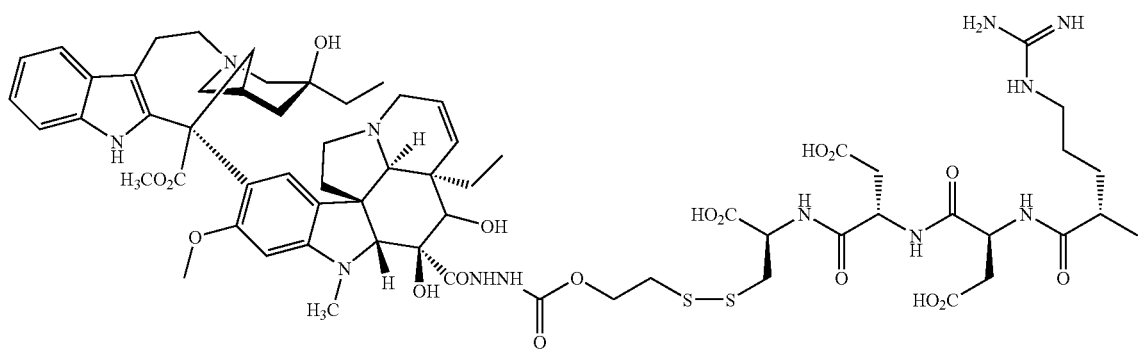

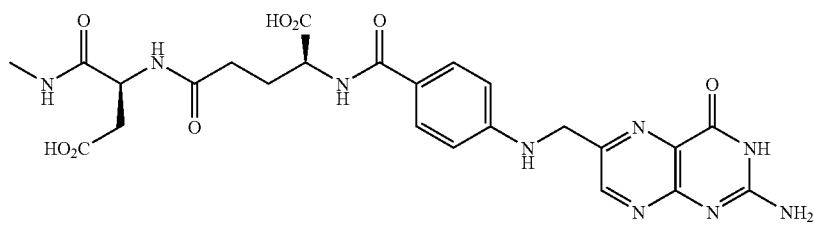

The compounds of Examples 16a and 16b were prepared from the peptidyl fragment Pte-Glu-Asp-Arg-Asp-Asp-Cys-OH, prepared according to the general procedure described in Scheme 12. The Michael addition of this peptidyl fragment to the maleimido derivative of seco-CBI-bis-indole resulted in the folate conjugates Example 16a. The peptidyl fragment also reacted with either the thiosulfonate or pyridyldithio-activated vinblastine to form Example 16b. The maleimido derivative of seco-CBI-bis-indole, and the thiosulfonate and pyridyldithio-activated vinblastine intermediates were prepared using the procedures described herein for other examples.

EXAMPLE 17a

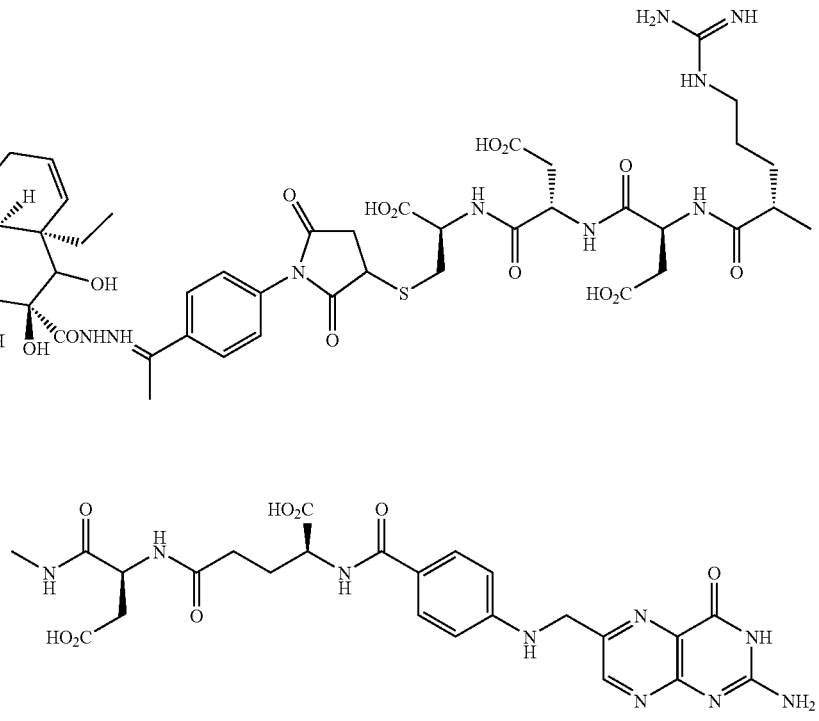

Deacetylvinblastine monohydrazide (1 eq.) (see Barnett et al., *J. Med. Chem,* 1978, 21, 88, the disclosure of which is incorporated herein by reference) was treated in fresh distilled THF with 1 eq. of trifluoroacetic acid. After stirring for 10 min the solution was treated with 1.05 eq. of N-(4-acetylphenyl)maleimide. Acyl hydrazone formation was completed in 45 min and the solvent was evaporated. The peptidyl fragment Pte-Glu-Asp-Arg-Asp-Asp-Cys-OH (0.85 eq.), prepared according to the general approach outlined in Scheme 12, was dissolved in water, and the pH was adjusted to 2.5 with 0.1 N HCl, causing the peptide to precipitate. The peptidyl fragment was collected by centrifugation, dried, and dissolved in DMSO. To the resulting clear yellow solution was added Hünig's base (15 eq.) and the acyl hydrazone Michael adduct. After 1 h, the final conjugate was purified by HPLC.

EXAMPLE 17b

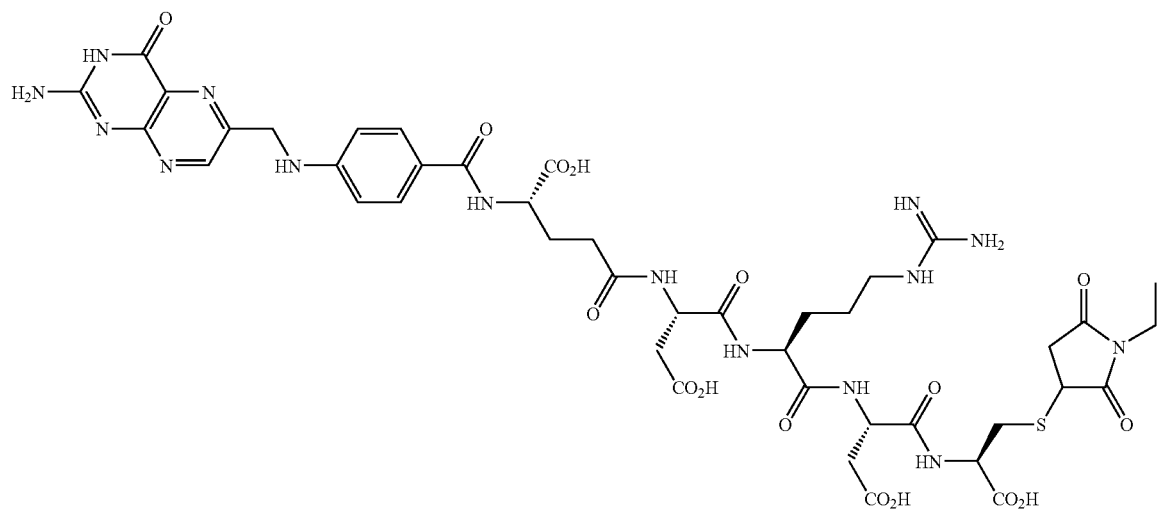

-continued

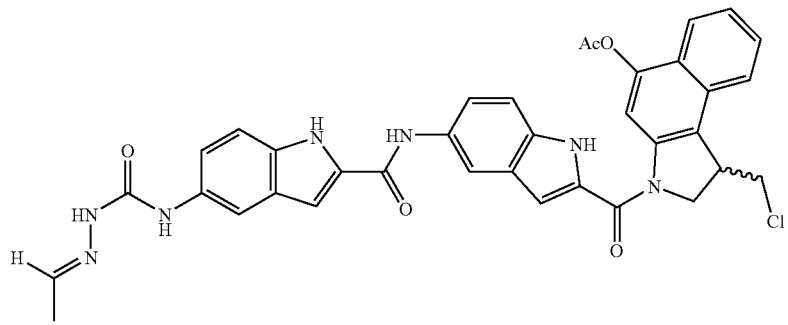

EXAMPLE 17c

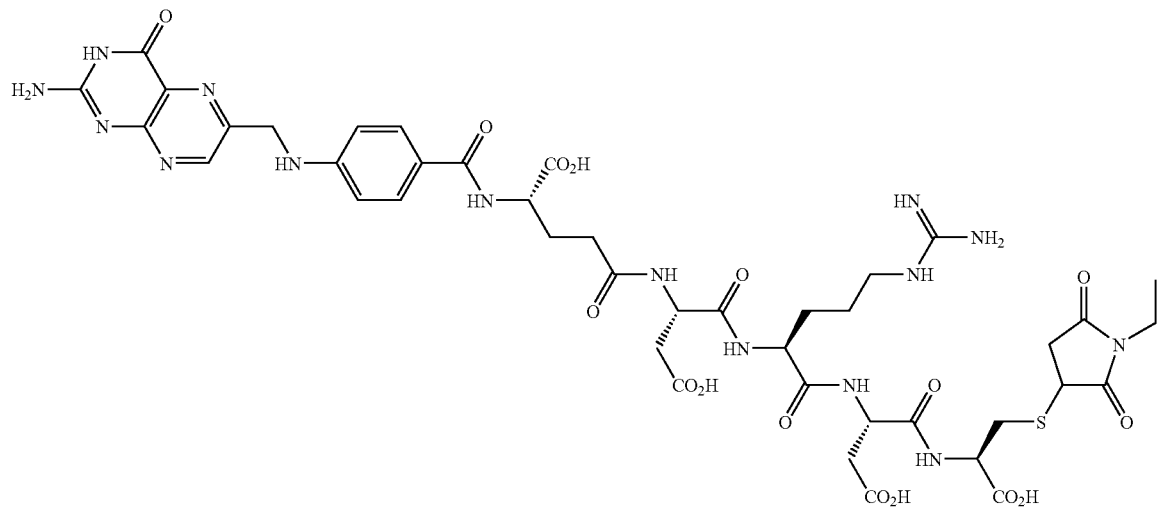

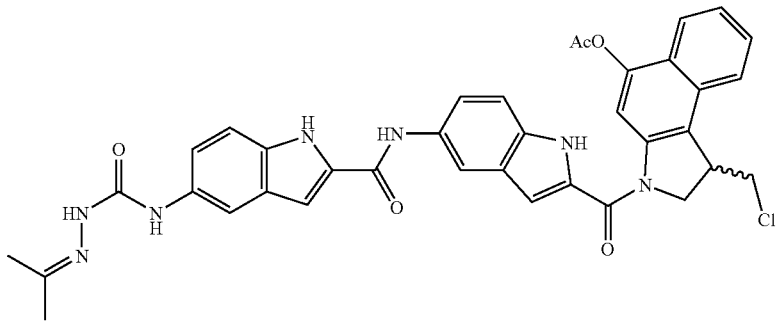

Examples 17b and 17c were prepared according to the procedure described in Example 17a with the corresponding peptidyl fragments and monohydrazide derivatives of CBI.

The compounds of Examples 18-41 were prepared according to the procedure generally described in Example 13. Examples 18-41 were characterized by electrospray mass spectroscopy (ES MS), and other spectroscopic techniques, including 1D and 2D NMR, and UV.

EXAMPLE 18
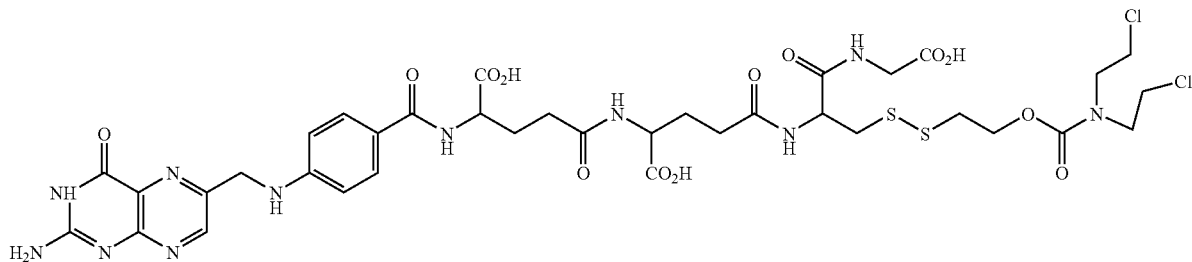
ES MS (m+H)+ 1071.9, (m+Na)+ 1093.9; $^1$H NMR (D$_2$O) δ 2.6 (t, 4H), 2.7 (t, 4H), 4.15 (s, 2H), 5.45 (s, 2H), 7.75 (d, 2H), 8.15 (d, 2H), 8.9 (s, 1H).
EXAMPLE 19
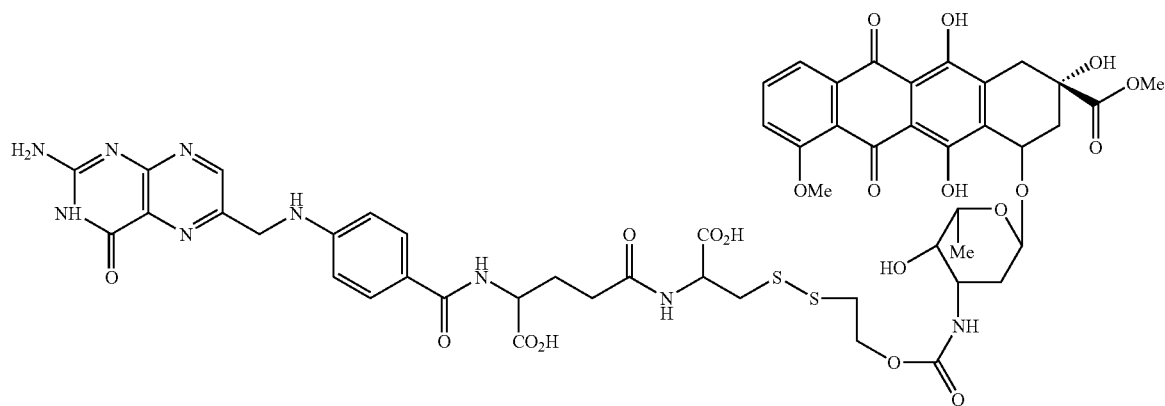
UV (nm) 233 (max), 255, 280; $^1$H NMR (D$_2$O, NaOD, CD$_3$CN) δ 1.15 (d, 3H), 2.3 (s, 3H), 3.6 (s, 1H), 3.85 (s, 3H), 4.9 (s, 1H), 5.3 (s, 1H), 6.5 (d, 2H), 7.3 (m, 1H), 7.5 (d, 2H), 7.65 (d, 2H), 8.4 (s, 1H).
EXAMPLE 20
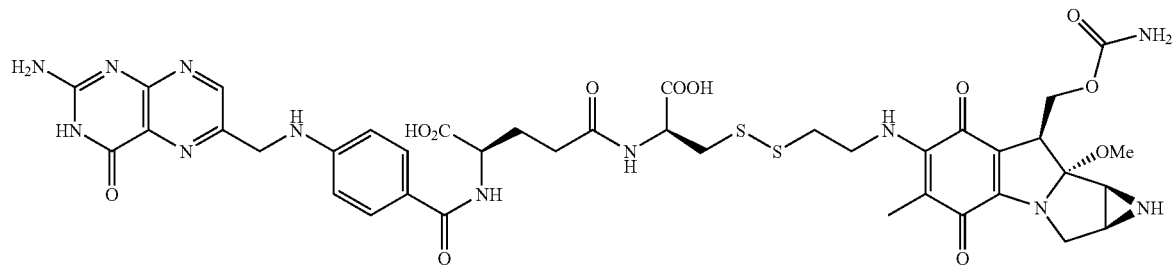

ES MS (m−H)⁻ 935.6, (m+H)⁺ 937.4, (m+Na)⁺ 959.5.
EXAMPLE 21
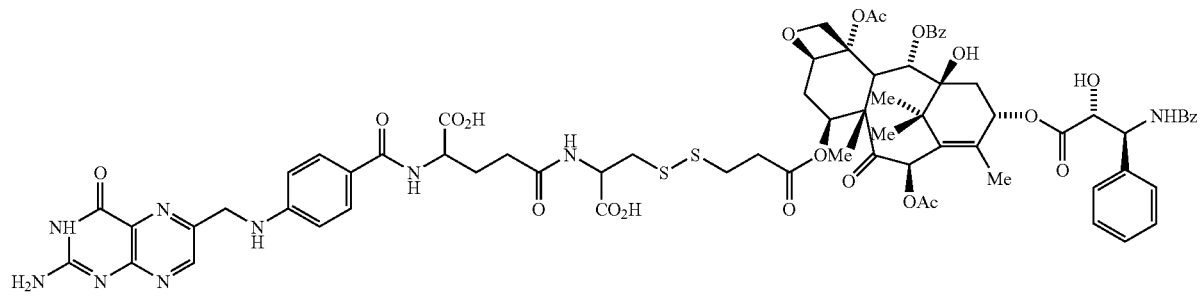
¹H NMR (D₂O, NaOD, CD₃CN) δ 0.1 (s, 1H), 1.1 (s, 3H), 1.2 (s, 3H), 1.75 (s, 3H), 1.9 (s, 3H), 2.05 (s, 3H), 2.35 (s, 3H), 3.3 (dd, 2H), 3.8 (d, 1H), 4.3 (q, 2H), 4.9 (d, 1H), 5.1 (d, 1H), 5.4 (q, 1H), 5.55 (d, 1H), 5.65 (d, 1H), 6.1 (t, 1H), 6.35 (s, 1H), 6.9 (d, 2H), 7.9 (d, 2H), 8.15 (d, 2H), 8.7 (s, 1H).
EXAMPLE 22
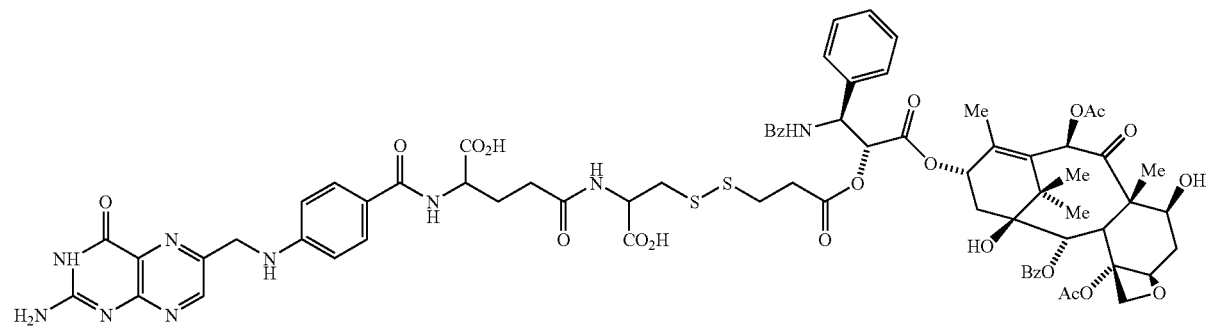
EXAMPLE 23
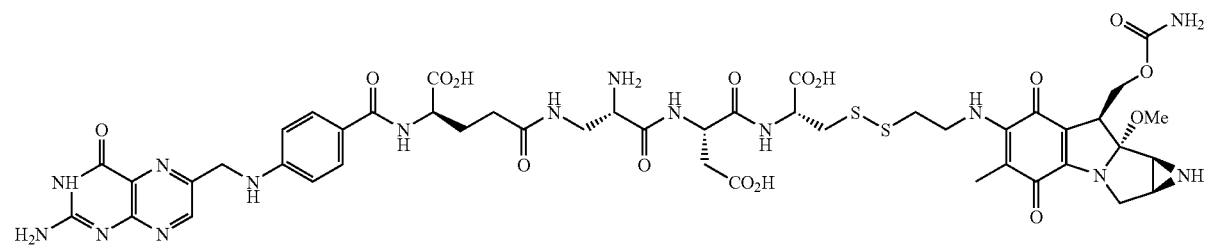

ES MS (m−H)⁻ 1136.5.
EXAMPLE 24
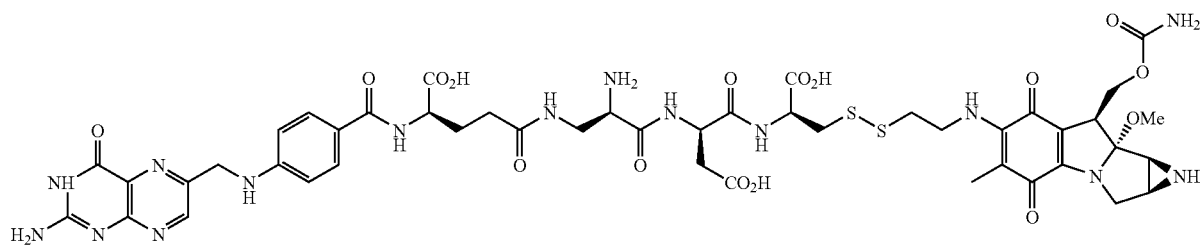
ES MS (m−H)⁻ 1136.3, (m+H)⁺ 1138.0.
EXAMPLE 25
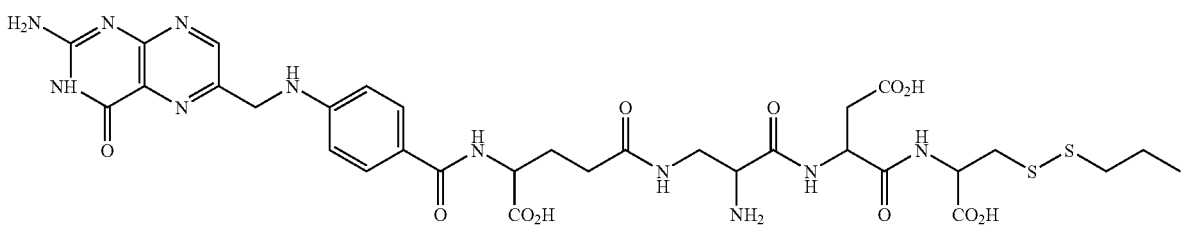
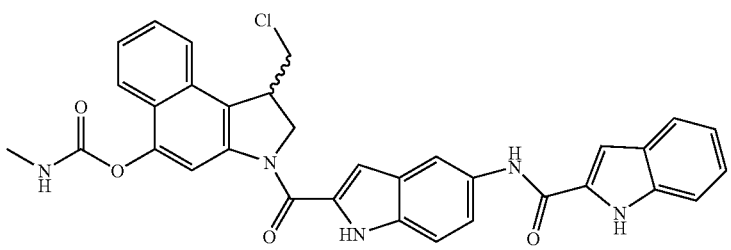
ES MS (m+H)⁺ 1382.3, (m+Na)⁺ 1405.4.
EXAMPLE 26
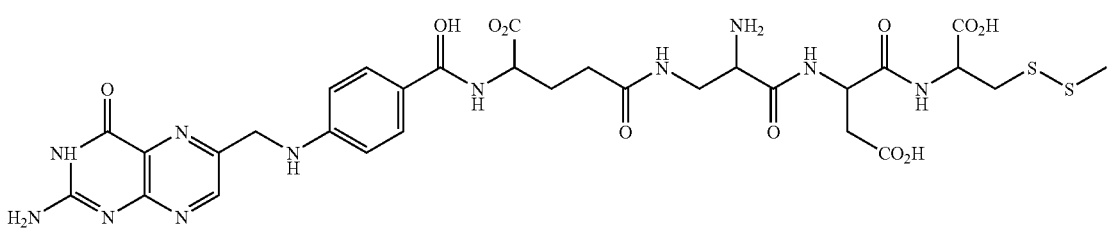

-continued
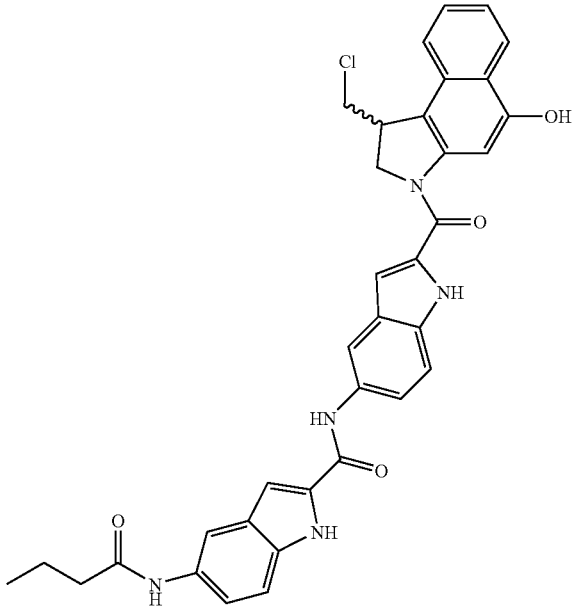
ES MS (m−H)⁻ 1379.2, (m+H)⁺ 1381.2.
EXAMPLE 27
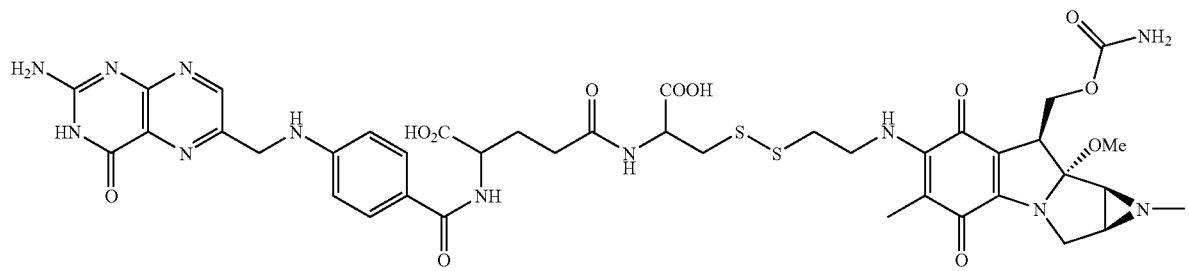
ES MS (mH)⁻ 949.2; $^1$H NMR (D$_2$O) δ 1.55 (s, 3H), 1.95 (m, 2H), 2.05 (s, 3H), 2.45 (s, 3H), 2.75 (dd, 2H), 2.95 (dd, 2H), 3.05 (s, 3H), 3.3 (dd, 2H), 3.35 (d, 2H), 3.45 (t, 2H), 4.85 (q, 2H), 6.5 (d, 2H), 7.45 (d, 2H), 8.5 (s, 1H).
EXAMPLE 28
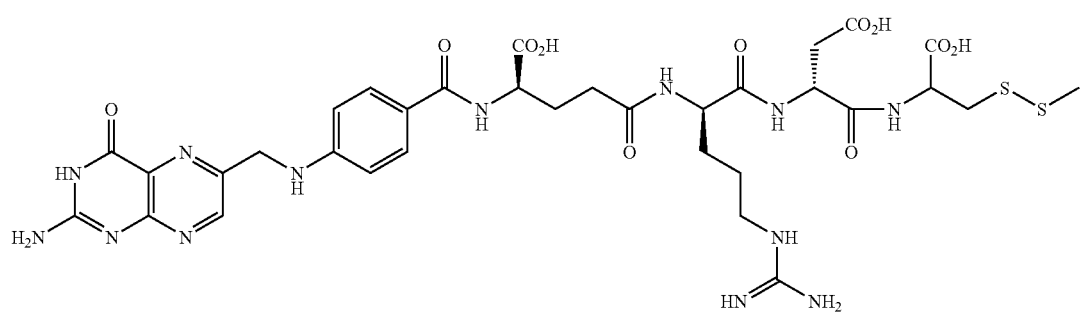

-continued
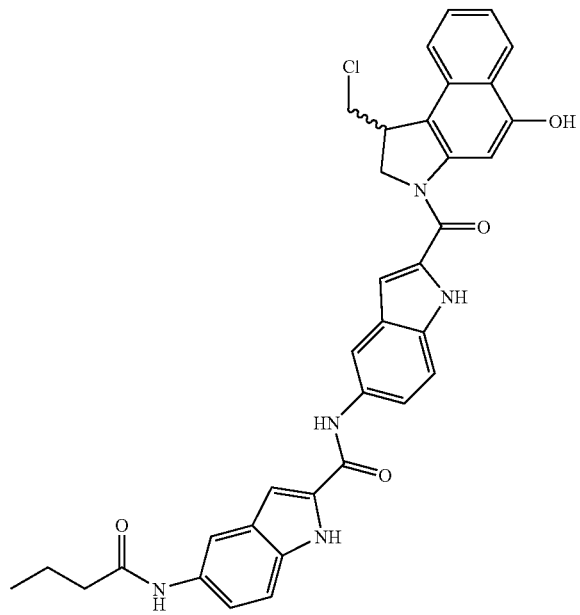
$^1$H NMR (DMSO-d$_6$) δ 1.5 (s), 2.25 (t), 2.75 (m), 3.9 (q), 4.6 (d), 4.85 (t), 6.6 (d), 7.6 (d), 7.9 (d), 8.15 (d), 8.25 (t), 8.65 (s), 8.7 (m), 9.3 (m), 10.2 (t).
EXAMPLE 29
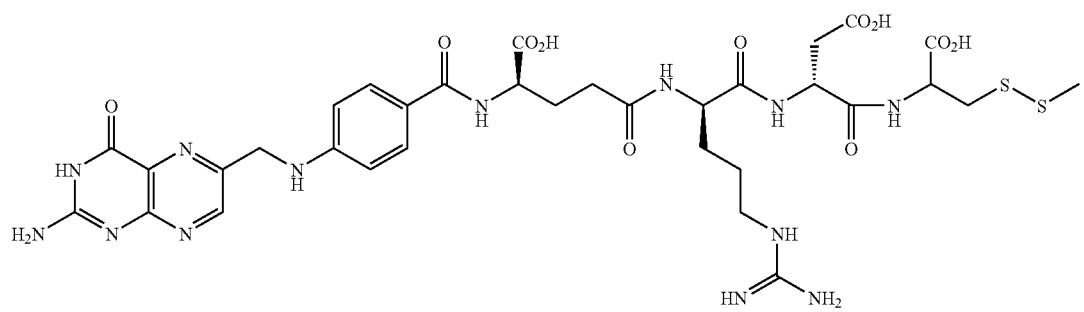

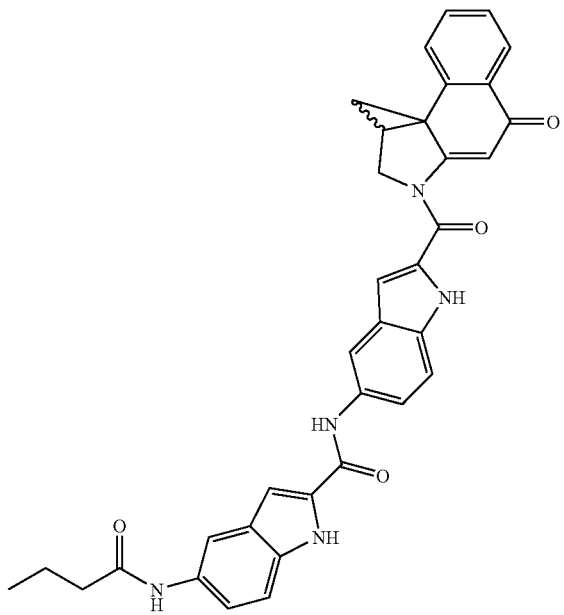
ES MS (m−H)⁻ 1413.5, (m+H)⁺ 1415.3.
EXAMPLE 30
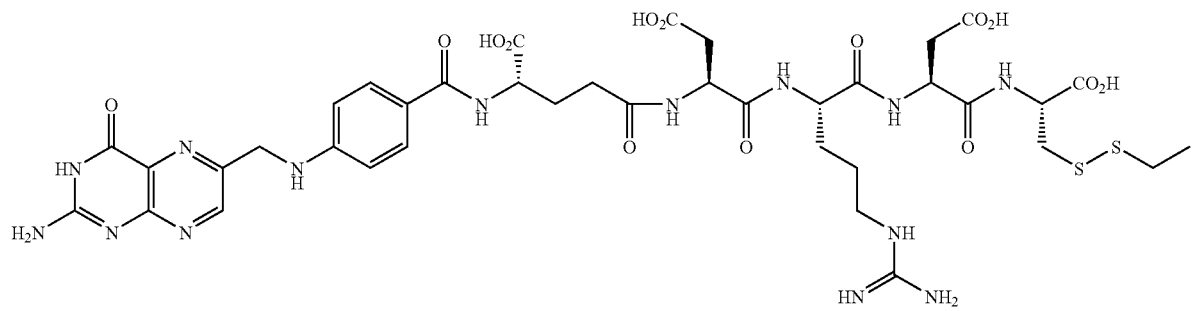
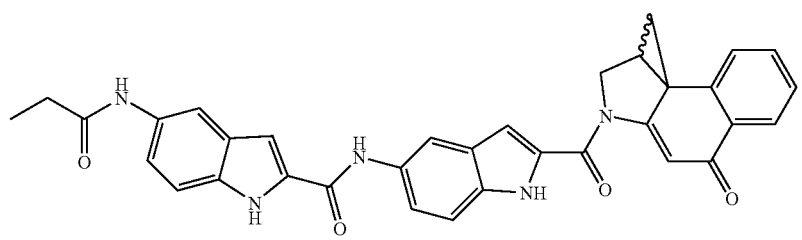
ES MS (m+H)⁺ 1530.2; ¹H NMR (DMSO-d$_6$/D$_2$O) δ 1.2 (s, 1H), 2.9 (t, 1H), 3.65 (t, 1H), 4.15 (t, 1H), 4.25 (t, 1H), 4.35 (t, 1H), 6.7 (d, 2H), 7.0 (s, 1H), 8.1 (d, 2H), 8.25 (s, 1H), 8.7 (s, 1H).

EXAMPLE 31
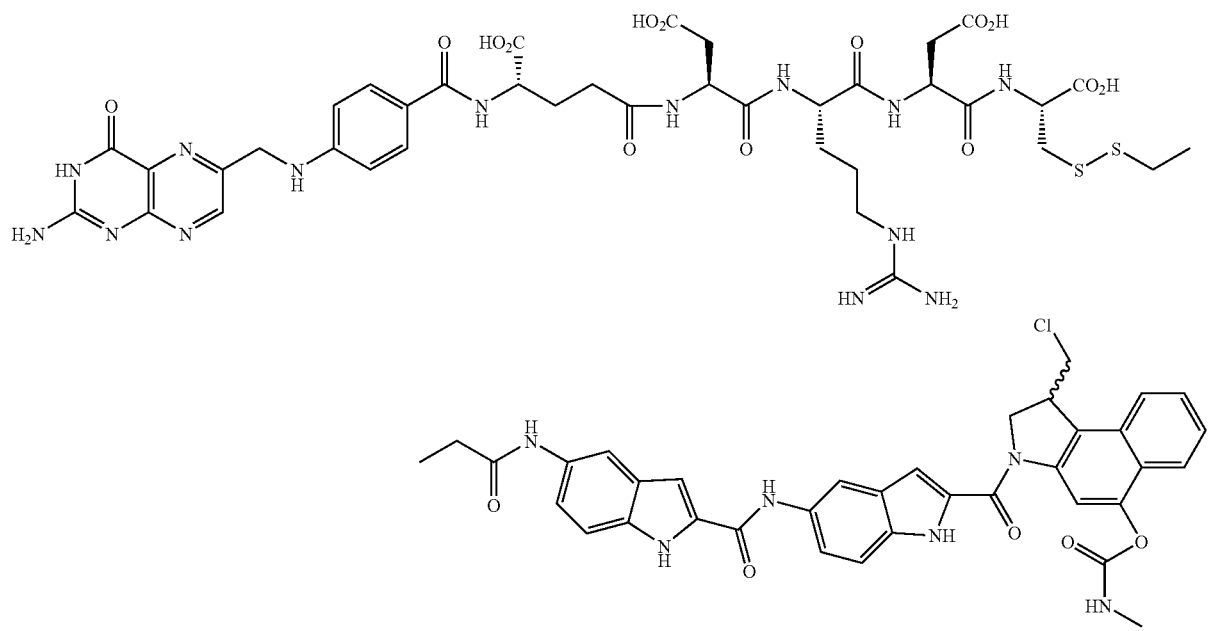
¹H NMR (DMSO-d₆) δ 1.75 (s, 1H), 1.85 (s, 1H), 2.1 (t, 2H), 4.3 (t, 1H), 4.6 (d, 1H), 4.9 (t, 1H), 6.6 (d, 2H), 8.15 (s, 2H), 8.6 (s, 1H).
EXAMPLE 32
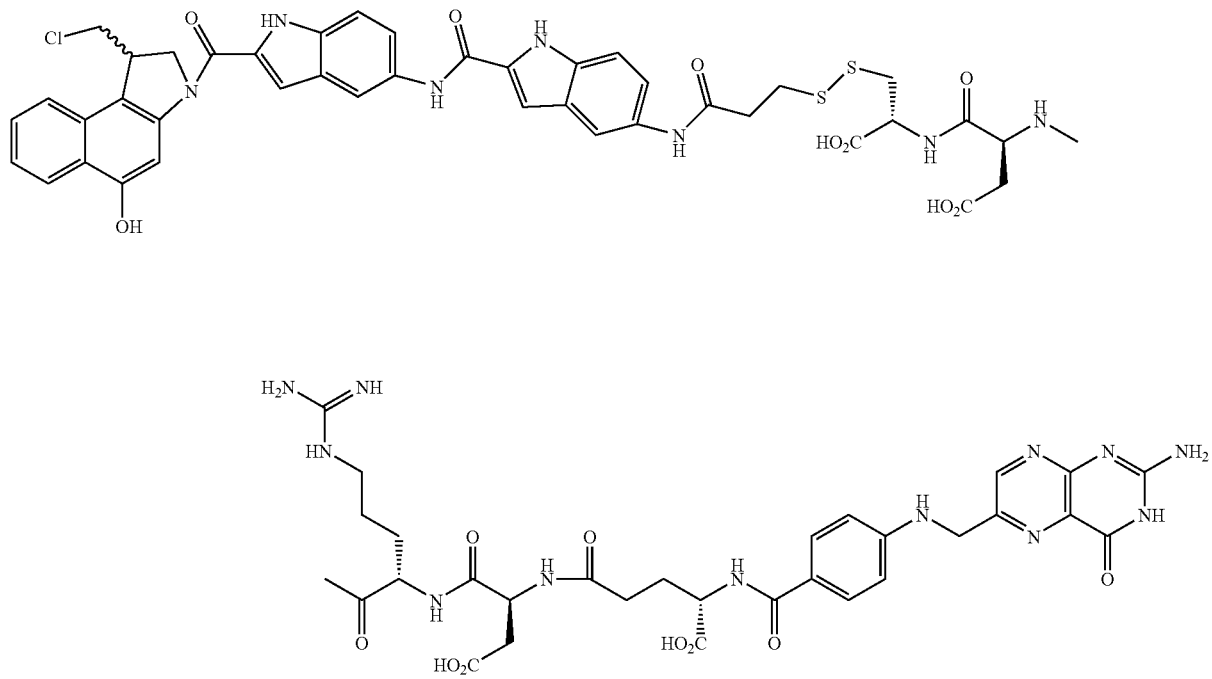

ES MS (m+H)+ 1408.4.
EXAMPLE 33
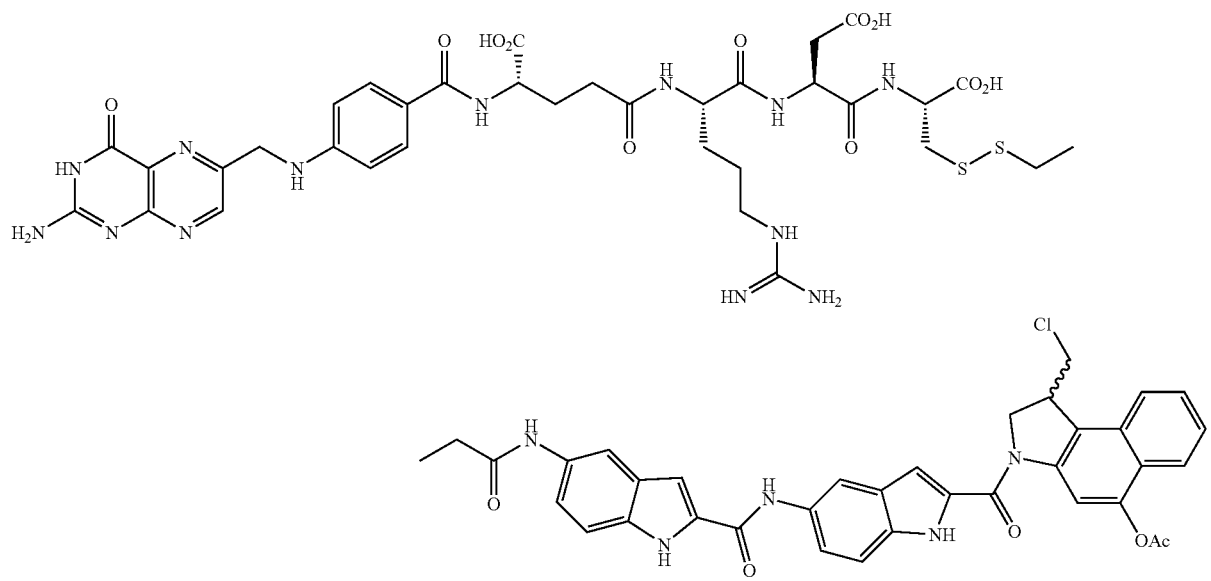
ES MS (m−H)− 1491.1, (m+H)+ 1493.1; $^1$H NMR (DMSO-$d_6$/$D_2O$) δ 4.15 (q, 1H), 4.6 (d, 1H), 4.9 (t, 1H), 6.6 (d, 2H), 7.25 (s, 1H), 7.4 (d, 1H), 7.9 (d, 1H), 7.95 (d, 2H), 8.15 (d, 2H), 8.6 (s, 1H).
EXAMPLE 34
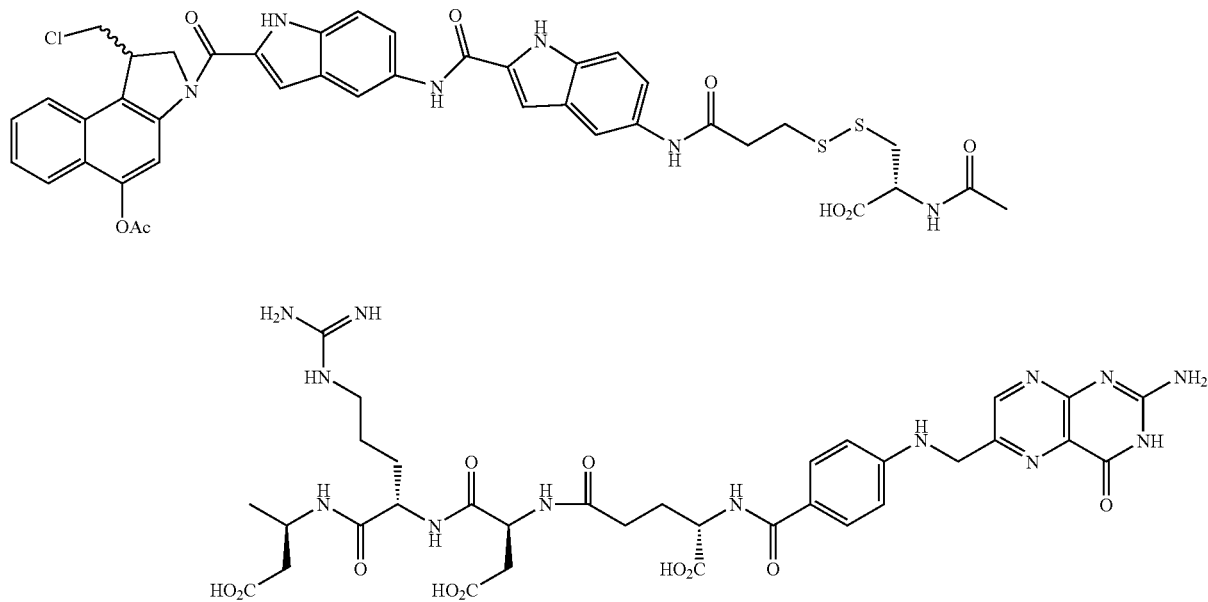
$^1$H NMR (DMSO-$d_6$/$D_2O$) δ 2.1 (t, 2H), 2.75 (q, 2H), 4.3 (t, 1H), 4.65 (d, 1H), 4.9 (t, 1H), 6.6 (d, 2H), 7.9 (d, 1H), 8.0 (d, 2H), 8.2 (t, 2H), 8.6 (s, 1H).

EXAMPLE 35
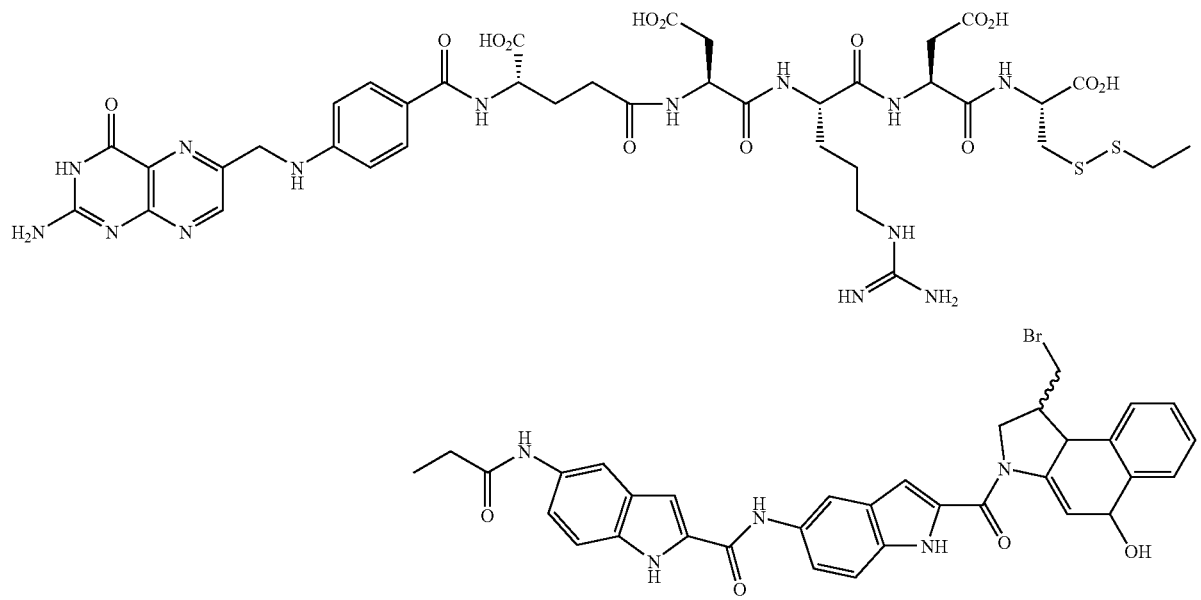
EXAMPLE 36
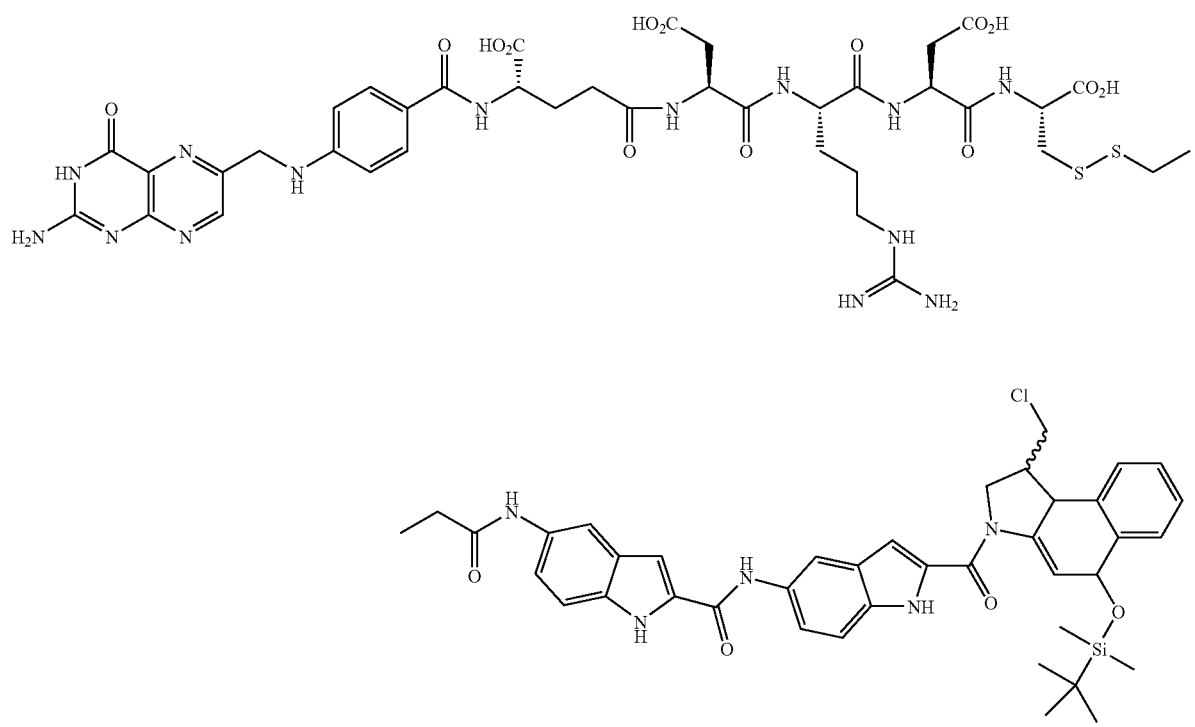
ES MS (m+H)+ 1680.4; ¹H NMR (DMSO-d$_6$/D$_2$O) δ 0.3 (s, 3H), 0.35 (s, 3H), 1.05 (s, 9H), 2.15 (t, 2H), 4.15 (t, 1H), 4.85)t, 1H), 6.6 (d, 2H), 7.55 (t, 4H), 7.9 (d, 1H), 8.0 (s, 1H), 8.05 (d, 1H), 8.15 (s, 1H), 8.6 (s, 1H).

EXAMPLE 37
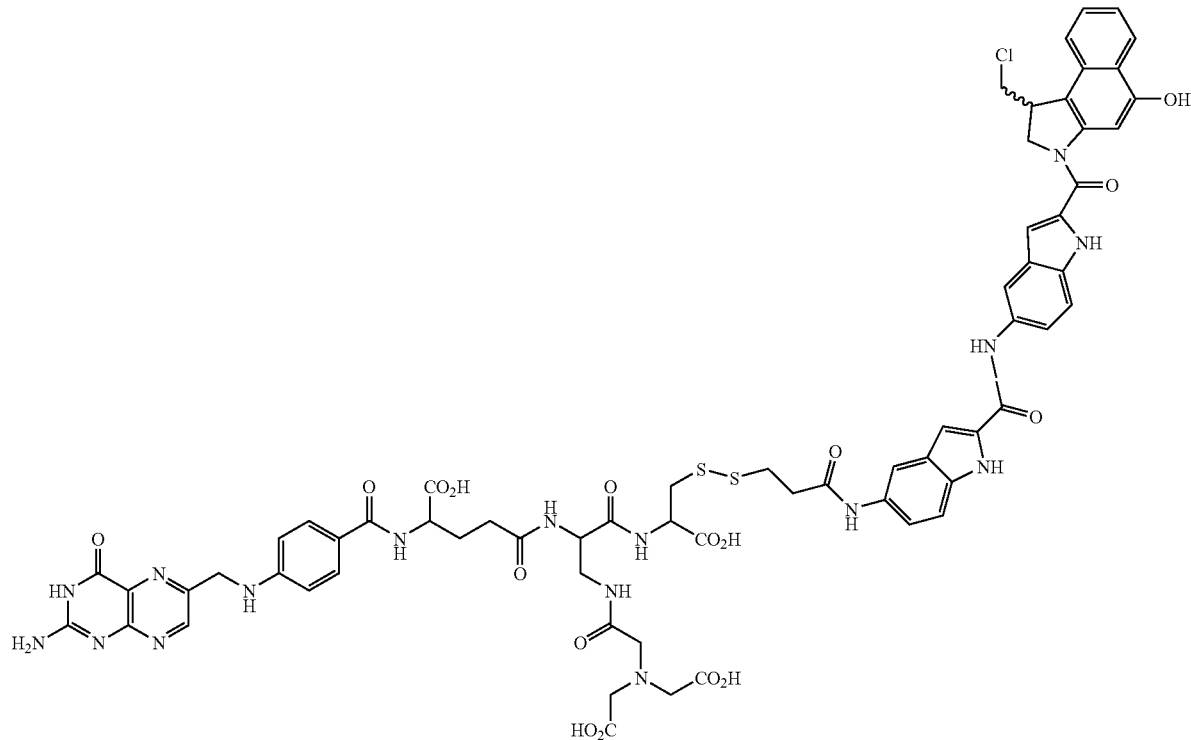
$^1$H NMR (DMSO-$d_6$/D$_2$O) δ 1.1 (s, 3H), 1.8 (s, 1H), 4.55 (d, 1H), 4.8 (t, 1H), 6.6 (d, 2H), 7.8 (d, 1H), 8.1 (d, 1H), 8.15 (s, 1H), 8.6 (s, 1H).
EXAMPLE 38
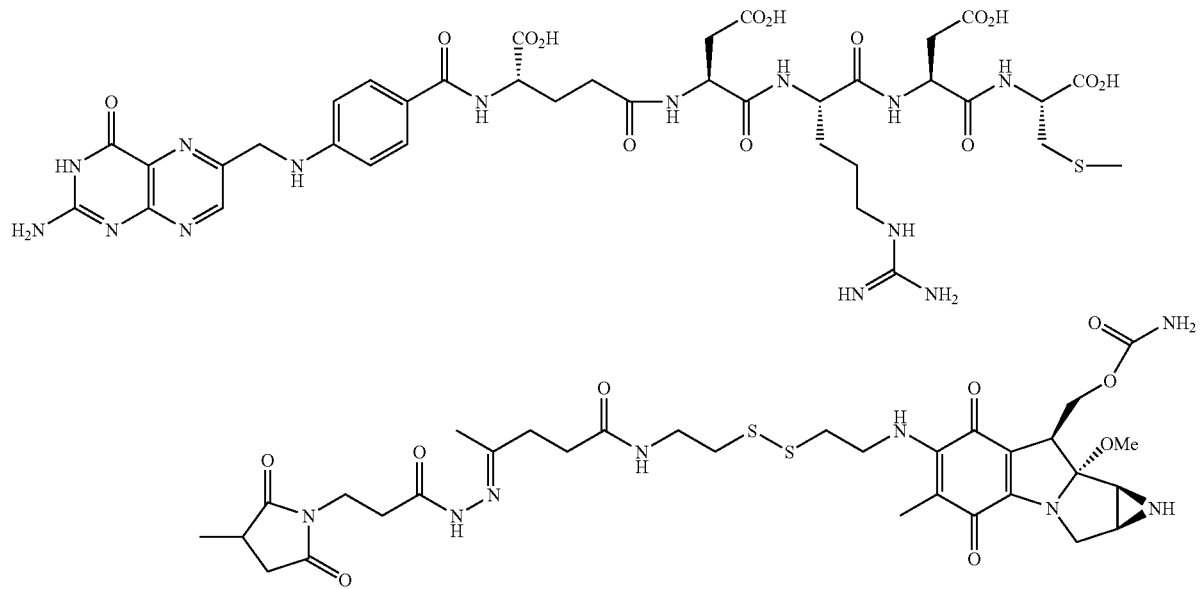

EXAMPLE 39

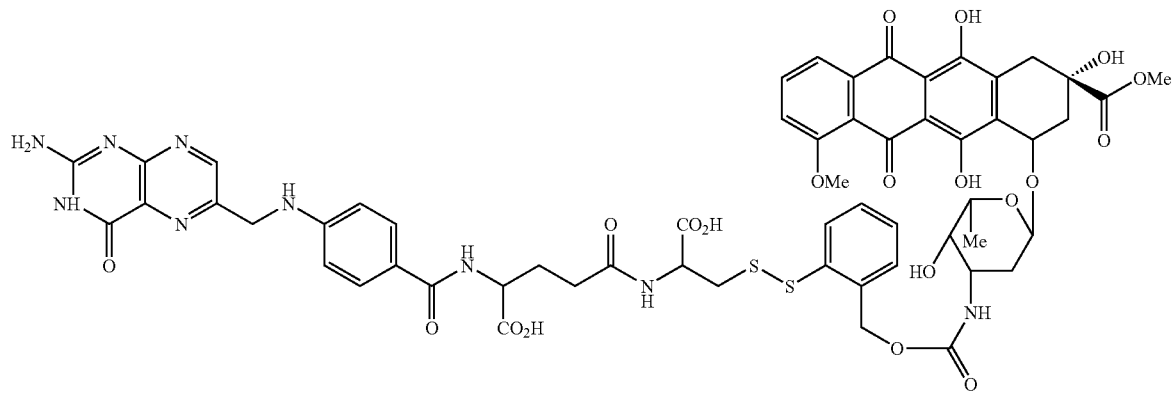

EXAMPLE 40

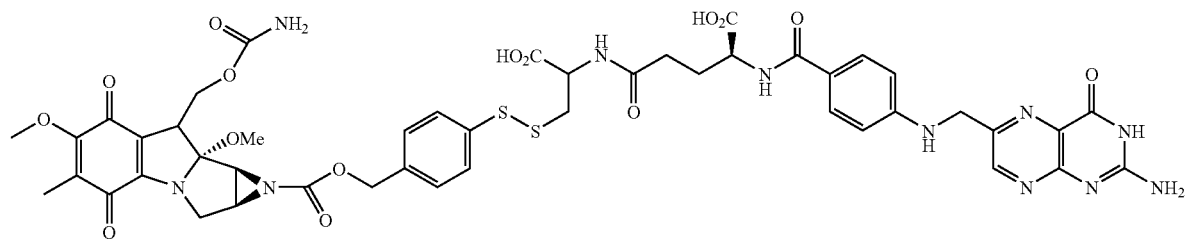

EXAMPLE 41

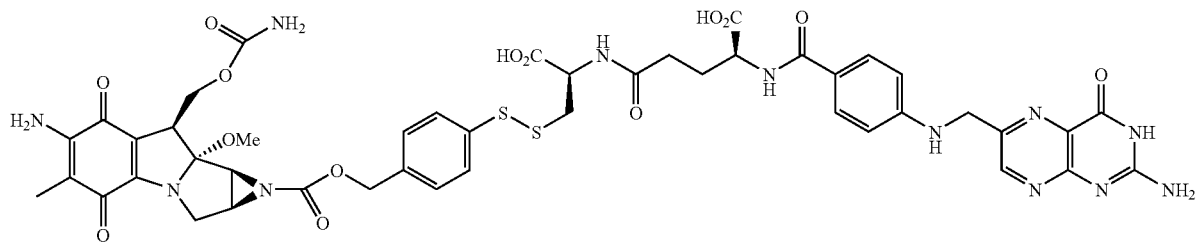

EXAMPLE 42

Inhibition of Tumor Growth in Mice Treated with EC112

The anti-tumor activity of the compounds of Examples 9b (EC111) and 9c (EC112), where the drug is daunorubicin, when administered intravenously (i.v.) to tumor-bearing animals, was evaluated in Balb/c mice bearing subcutaneous M109 tumors. Four days post tumor inoculation in the subcutis of the right axilla with $1\times10^6$ M109 cells, mice (5/group) were injected i.v. twice a week for 4 weeks with 2-10 μmol/kg of the compound of either Example 9b or Example 9c or with unconjugated daunorubicin or PBS. Tumor growth was measured using calipers at 3-day or 4-day intervals in each treatment group. Tumor volumes were calculated using the equation $V=a\times b^2/2$, where "a" is the length of the tumor and "b" is the width expressed in millimeters. Animal body weight was also determined at 3-day or 4-day intervals.

Figure 2:
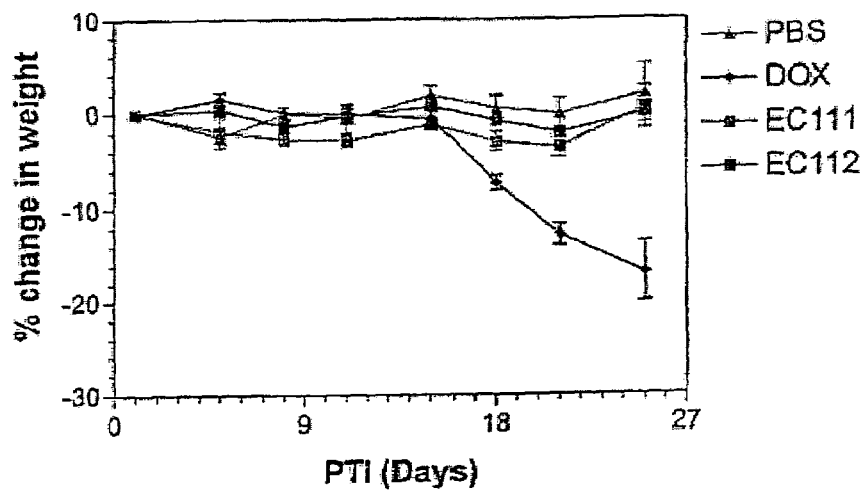
FIG. 2 shows the effect of EC112 (Example 9c) on animal body weights.

As shown in FIGS. 1 and 2, treatment with the compound of Example 9c was effective in delaying the growth of M109 tumors with no apparent toxicity (based on animal body weights). Unconjugated doxorubicin also provided an anti-tumor response, but with concomitant toxicity based on body weights.

EXAMPLE 43

Inhibition of Tumor Growth in Mice Treated with EC105

The protocol was as described in Example 42 except that the compound of Example 10a (EC105) was used, where the drug is bis-indolyl-seco-CBI. The compound of Example 10a was injected at a dose of 0.3 μmol/kg. Also, two subcutaneous tumor models were tested including the M109 model (folate receptor-positive) and the 4T1 model (folate receptor-negative), and in some animals a 67-fold excess of free folate (20 μmol/kg; FA) was coinjected with the conjugate (i.e., the compound of Example 10a).

Figure 3:
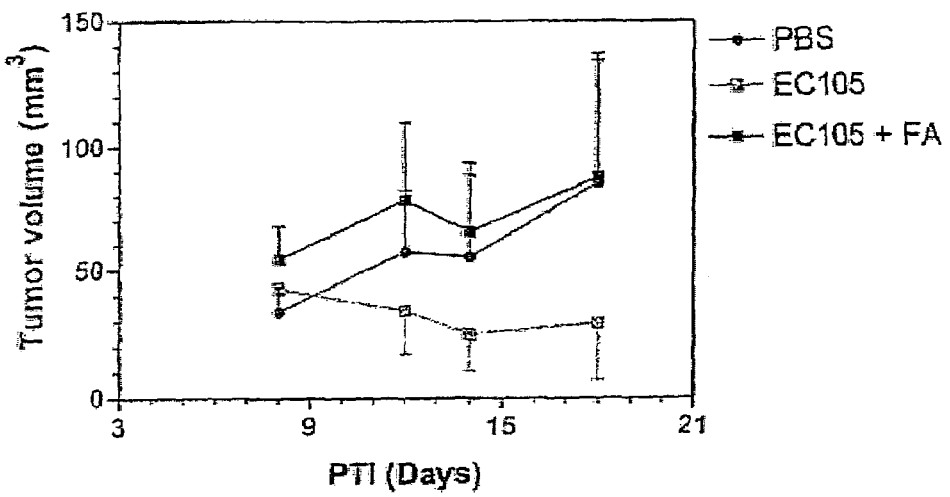
FIG. 3 shows the inhibition of M109 tumor growth by EC105 (Example 10a).
Figure 4:
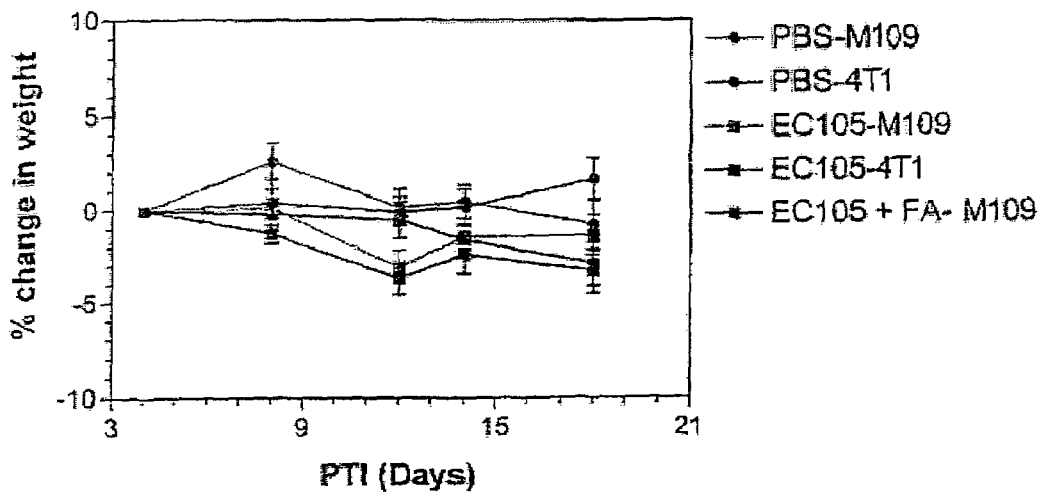
FIG. 4 shows the effect of EC105 (Example 10a) on animal body weights.
Figure 5:
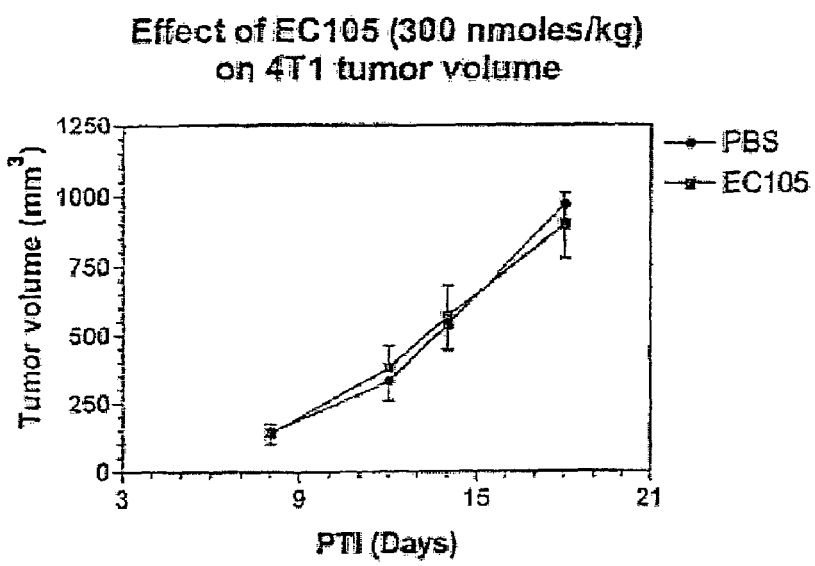
FIG. 5 shows the lack of inhibition of 4T1 tumor growth by EC105 (Example 10a).

A striking anti-tumor response was observed with the compound of Example 10a with no apparent toxicity based on animal body weights (see FIGS. 3 and 4). The anti-tumor response with the compound of Example 10a was blocked with excess free folate demonstrating the specificity of the response (see FIG. 3). As shown in FIG. 5, no anti-tumor activity was observed in the 4T1 model (folate receptor-negative) again demonstrating the specificity of the response.

EXAMPLE 44

Inhibition of Tumor Growth in Mice Treated with EC145

The anti-tumor activity of the compound of Example 16b (EC145), where the drug is deacetylvinblastine monohydrazide, when administered intravenously (i.v.) to tumor-bearing animals, was evaluated in Balb/c mice bearing subcutaneous M109 tumors. Approximately 11 days post tumor inoculation in the subcutis of the right axilla with $1 \times 10^6$ M109 cells (average tumor volume at $t_o$=60 mm$^3$), mice (5/group) were injected i.v. two times a week (BIW), for 3 weeks with 1500 nmol/kg of EC145 or with an equivalent dose volume of PBS (control). Tumor growth was measured using calipers at 2-day or 3-day intervals in each treatment group. Tumor volumes were calculated using the equation $V=a \times b^2/2$, where "a" is the length of the tumor and "b" is the width expressed in millimeters.

Figure 6:
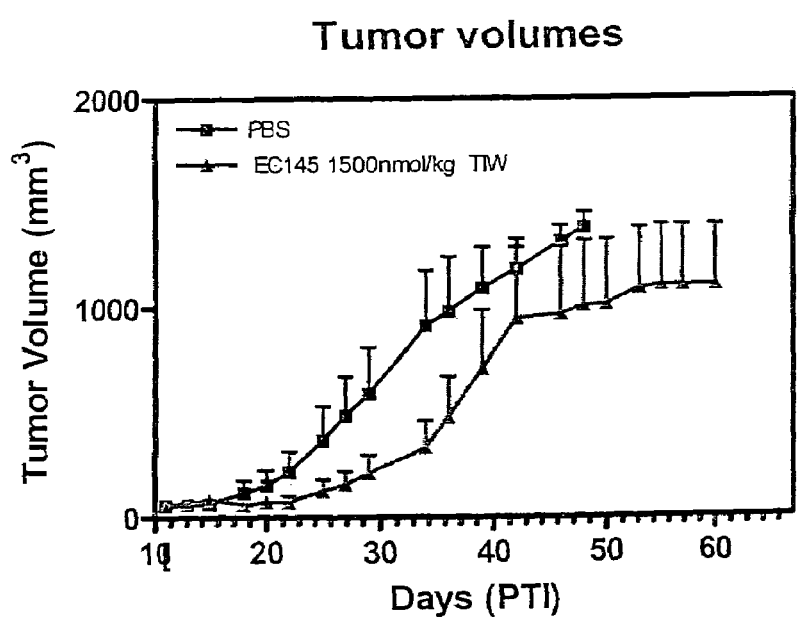
FIG. 6 shows the inhibition of M109 tumor growth by EC145 (Example 16b).

As shown in FIG. 6, treatment with EC145 was effective in delaying the growth of M109 tumors relative to growth of M109 with tumors in saline-treated animals.

EXAMPLE 45

Inhibition of Tumor Growth in Mice Treated with EC140

The anti-tumor activity of the compound of Example 17a (EC140), where the drug is deacetylvinblastine monohydrazide, when administered intravenously (i.v.) to tumor-bearing animals, was evaluated in Balb/c mice bearing subcutaneous M109 tumors. Approximately 11 days post tumor inoculation in the subcutis of the right axilla with $1 \times 10^{16}$ M09 cells (average tumor volume at $t_o$=60 mm$^3$), mice (5/group) were injected i.v. three times a week (TIW), for 3 weeks with 1500 nmol/kg of EC140 or with an equivalent dose volume of PBS (control). Tumor growth was measured using calipers at 2-day or 3-day intervals in each treatment group. Tumor volumes were calculated using the equation $V=a \times b^2/2$, where "a" is the length of the tumor and "b" is the width expressed in millimeters.

Figure 7:
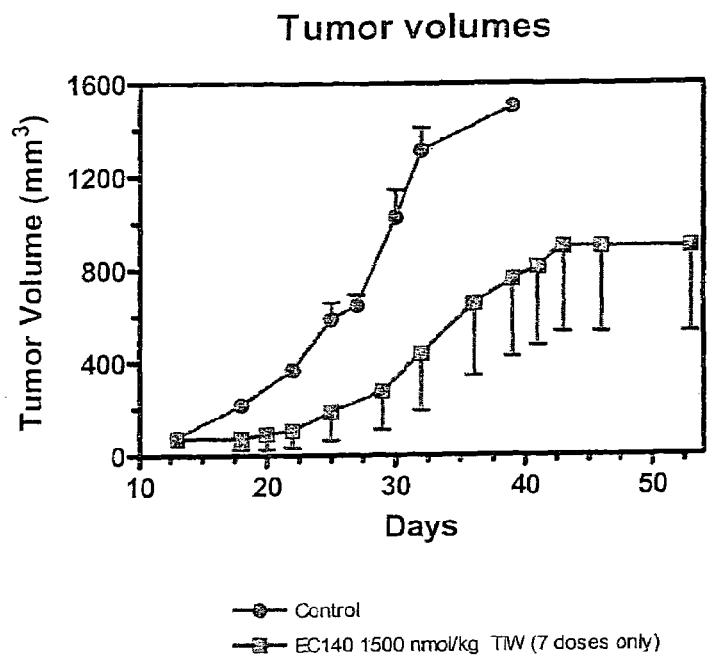
FIG. 7 shows the inhibition of M109 tumor growth by EC140 (Example 17a).

As shown in FIG. 7, treatment with EC140 was effective in delaying the growth of M109 tumors relative to growth of M109 with tumors in saline-treated animals.

EXAMPLE 46

Inhibition of Tumor Growth in Mice Treated with EC136

The anti-tumor activity of the compound of Example 10b (EC136), where the drug is CBI, when administered intravenously (i.v.) to tumor-bearing animals, was evaluated in DBA mice bearing subcutaneous L1210A tumors. Approximately 5 days post inoculation of $0.25 \times 10^5$ L1210A cells into the subcutis of the right axilla (average tumor volume at $t_o$~50 mm$^3$; mice 5/group) animals were injected i.v. three times a week (TIW) for 3 weeks with 400 nmol/kg of the EC136 or an equivalent dose volume of PBS alone (control). Tumor growth was measured using calipers at 2-day or 3-day intervals in each treatment group. Tumor volumes were calculated using the equation $V=a \times b^2/2$, where "a" is the length of the tumor and "b" is the width expressed in millimeters.

Figure 8:
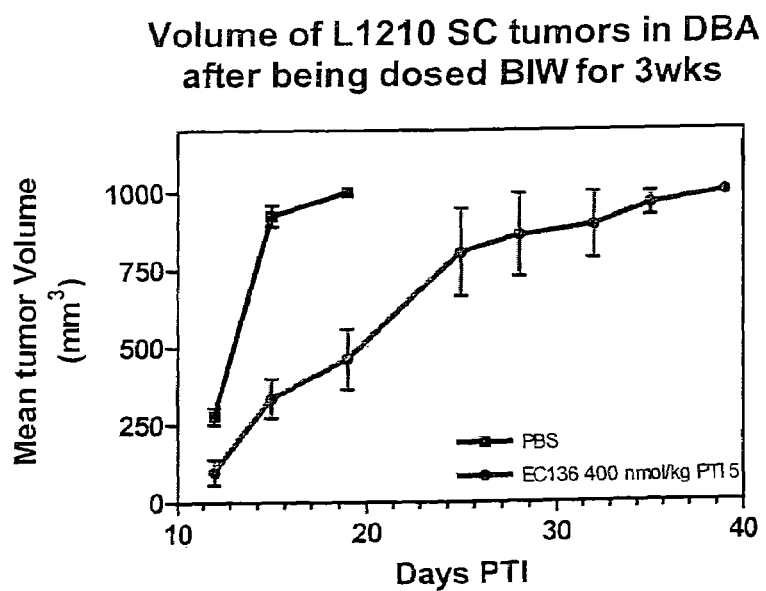
FIG. 8 shows the inhibition of L1210 tumor growth by EC136 (Example 10b).
Figure 9:
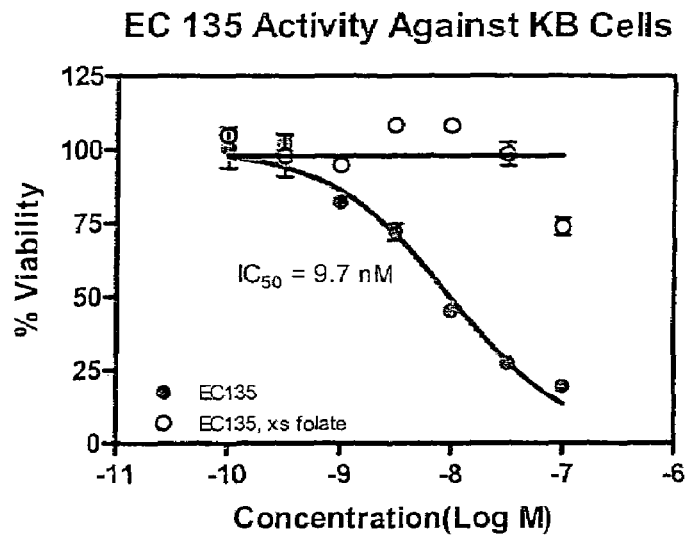
FIGS. 9-16 show the inhibition of cellular DNA synthesis by EC135, EC136, EC137, EC138, EC140, EC145, EC158, and EC159 (Examples 17b, 10b, 16a, 10c, 17a, 16b, 14e, and 15, respectively).
Figure 10:
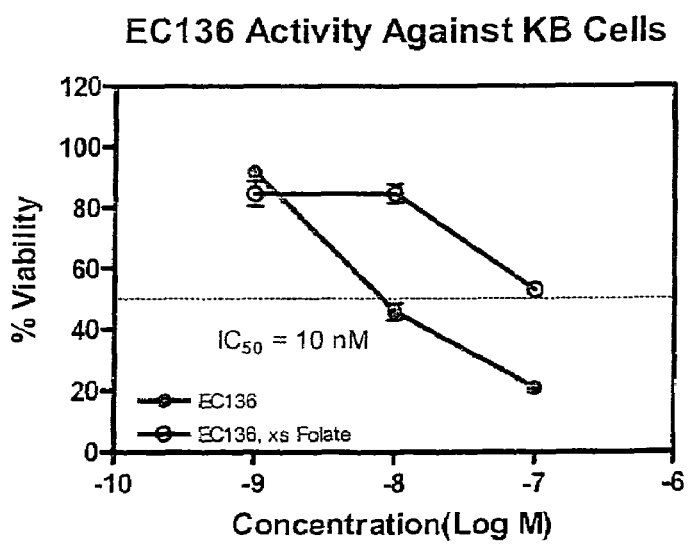
Figure 11:
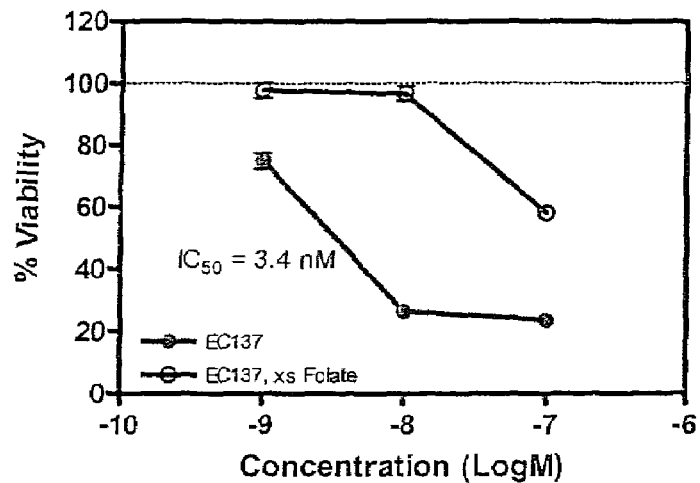
Figure 12:
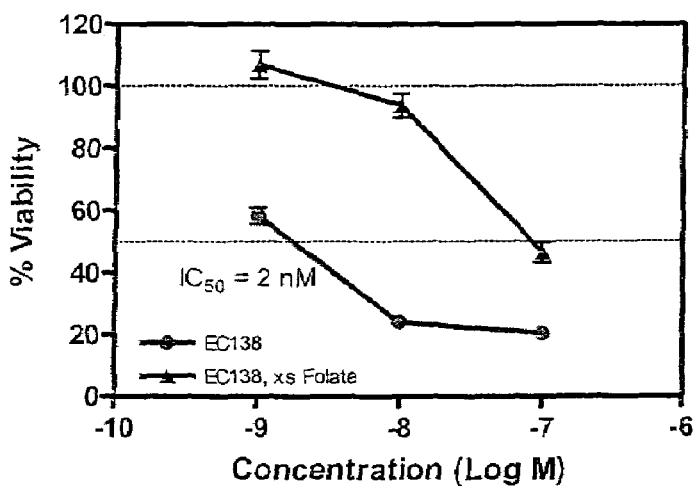
Figure 13:
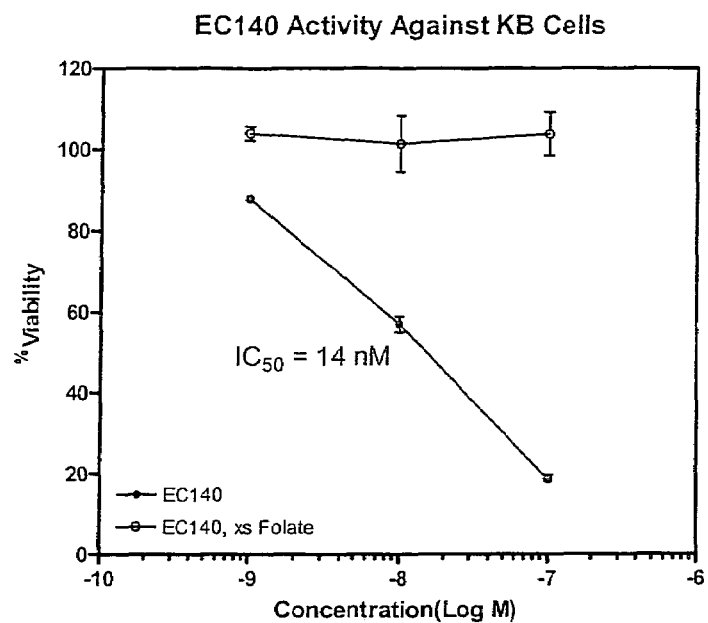
Figure 14:
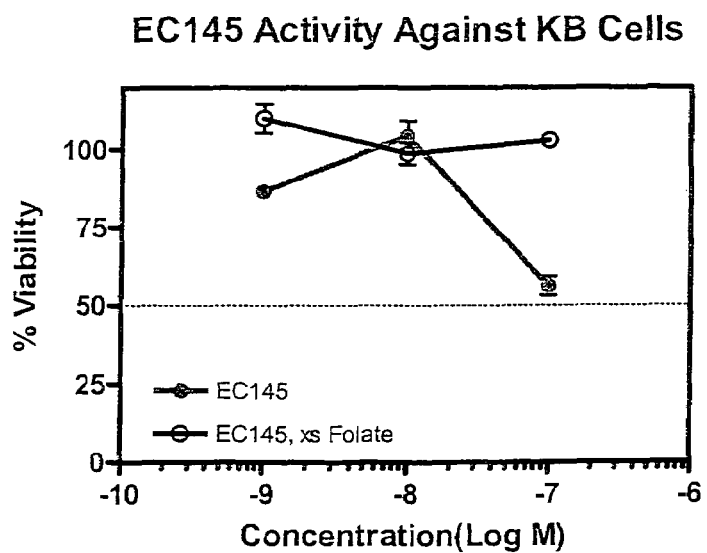
Figure 15:
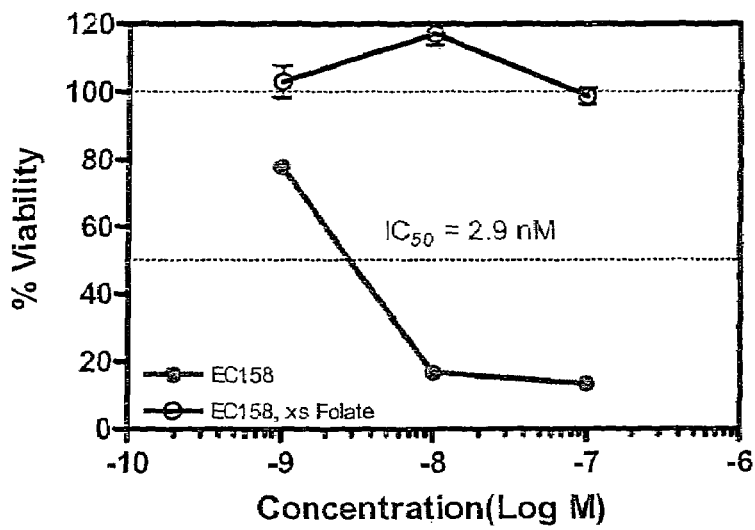
Figure 16:
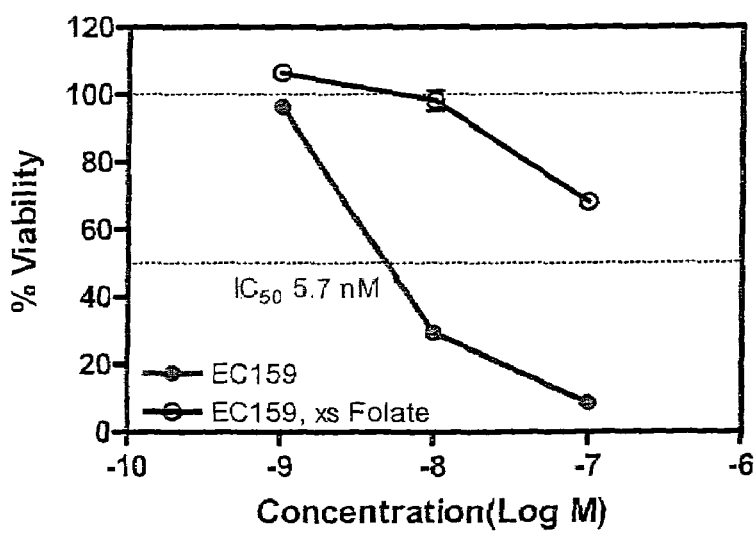

As shown in FIG. 8, treatment with EC136 was effective in delaying the growth of L1210A tumors, relative to growth of L1210A tumors in saline-treated animals.

EXAMPLE 47

Inhibition of Cellular DNA Synthesis by Various Folate-Drug Conjugates

The compounds of Examples 17b, 10b, 16a, 10c, 17a, 16b, 14e, and 15 (EC135, EC136, EC137, EC138, EC140, EC145, EC158, and EC159, respectively) were evaluated using an in vitro cytotoxicity assay that predicts the ability of the drug to inhibit the growth of folate receptor-positive KB cells. The compounds were comprised of folate linked to a respective chemotherapeutic drug, as prepared according to the protocols described herein. The KB cells were exposed for up to 7 h at 37 ° C. to the indicated concentrations of folate-drug conjugate (see x-axes of graphs shown in FIGS. 9-16) in the absence or presence of at least a 100-fold excess of folic acid. The cells were then rinsed once with fresh culture medium and incubated in fresh culture medium for 72 hours at 37° C. Cell viability was assessed using a $^3$H-thymidine incorporation assay.

As shown in FIGS. 9-16) dose-dependent cytotoxicity was measurable, and in most cases, the $IC_{50}$ values (concentration of drug conjugate required to reduce $^3$H-thymidine incorporation into newly synthesized DNA by 50%) were in the low nanomolar range. Furthermore, the cytotoxicities of these conjugates were reduced in the presence of excess free folic acid, indicating that the observed cell killing was mediated by binding to the folate receptor.

Similar results were obtained in this type of assay using EC158 and cell lines including IGROV (known cell line), A549-Clone-4 (A549 cells transfected with human folate receptor cDNA), New Line-01 (Line-01 cell mutant selected in vivo for folate receptor expression), M109, 4T1 Clone-2 (4T1 cells transfected with murine folate receptor cDNA), and HeLa cells.

What is claimed is:

1. A vitamin receptor binding drug delivery conjugate comprising:
   (a) a vitamin receptor binding moiety;
   (b) a bivalent linker; and
   (c) a drug, or an analog or derivative thereof;
   wherein the vitamin receptor binding moiety is covalently linked to the bivalent linker;
   the drug, or the analog or the derivative thereof, is covalently linked to the bivalent linker; and
   the bivalent linker comprises one or more components selected from the group consisting of spacer linkers, releasable linkers, and heteroatom linkers, and combinations thereof;
   providing that the bivalent linker includes at least one releasable linker that is not a disulfide; and
   providing that the compound is not selected from the group consisting of:

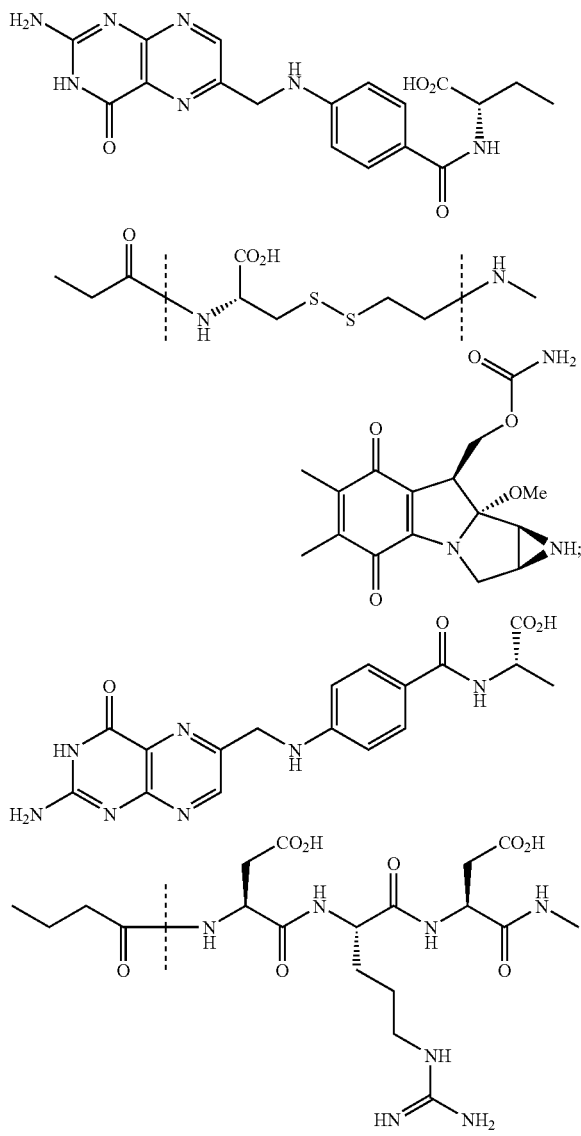

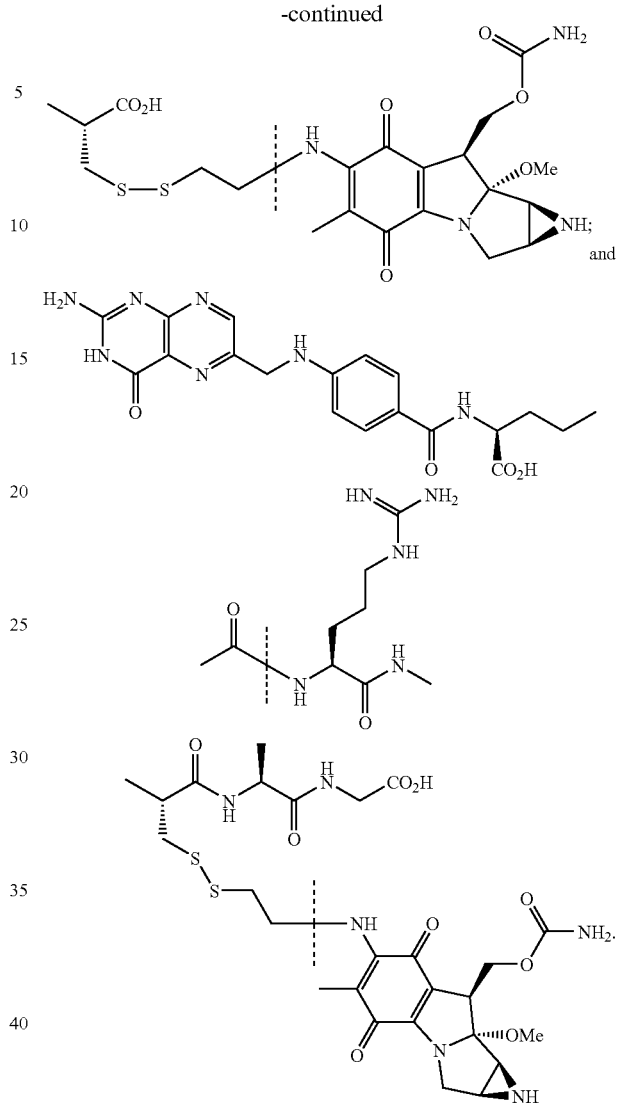

2. The drug delivery conjugate of claim 1 wherein the vitamin receptor binding moiety is selected from the group consisting of vitamins, and vitamin receptor binding analogs and derivatives thereof.

3. The drug delivery conjugate of claim 1 wherein the heteroatom linker is a nitrogen, oxygen, or sulfur atom, or is selected from the group of formulae consisting of —NHR$^1$NHR$^2$—, —SO—, —S(O)$_2$—, and —NR$^3$O—, wherein R$^1$, R$^2$, and R$^3$ are each independently selected from the group consisting of hydrogen, alkyl, aryl, arylalkyl, substituted aryl, substituted arylalkyl, heteroaryl, substituted heteroaryl, and alkoxyalkyl.

4. The drug delivery conjugate of claim 1 wherein the spacer linker is selected from the group consisting of carbonyl, thionocarbonyl, alkylene, cycloalkylene, alkylenecycloalkyl, alkylenecarbonyl, cycloalkylenecarbonyl, carbonylalkylcarbonyl, 1-alkylenesuccinimid -3-yl, 1-(carbonylalkyl)succinimid-3-yl, alkylenesulfoxyl, sulfonylalkyl, alkylenesulfoxylalkyl, alkylenesulfonylalkyl, carbonyltetrahydro-2H-pyranyl, carbonyltetrahydrofuranyl, 1-(carbonyltetrahydro-2H-pyranyl)succinimid-3-yl, and 1-(carbonyltetrahydrofuranyl)succinimid-3-yl, wherein each of said spacer linkers is optionally substituted with one or more substituents $X^1$;

wherein each substituent $X^1$ is independently selected from the group consisting of alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from the group consisting of an amino acid, an amino acid derivative, and a peptide, and wherein $R^6$ and $R^7$ are each independently selected from the group consisting of an amino acid, an amino acid derivative, and a peptide.

5. The drug delivery conjugate of claim 4 wherein the heteroatom linker is nitrogen, and wherein the substituent $X^1$ and the heteroatom linker are taken together with the spacer linker to which they are bound to form an heterocycle.

6. The drug delivery conjugate of claim 5 wherein the heterocycle is selected from the group consisting of pyrrolidines, piperidines, oxazolidines, isoxazolidines, thiazolidines, isothiazolidines, pyrrolidinones, piperidinones, oxazolidinones, isoxazolidinones, thiazolidinones, isothiazolidinones, and succinimides.

7. The drug delivery conjugate of claim 1 wherein the releasable linker is selected from the group consisting of methylene, 1-alkoxyalkylene, 1-alkoxycycloalkylene, 1-alkoxyalkylenecarbonyl, 1-alkoxycycloalkylenecarbonyl, carbonylarylcarbonyl, carbonyl(carboxyaryl)carbonyl, carbonyl(biscarboxyaryl)carbonyl, haloalkylenecarbonyl, alkylene(dialkylsilyl), alkylene(alkylarylsilyl), alkylene(diarylsilyl), (dialkylsilyl)aryl, (alkylarylsilyl)aryl, (diarylsilyl)aryl, oxycarbonyloxy, oxycarbonyloxyalkyl, sulfonylalkyl, iminoalkylidenyl, carbonylalkylideniminyl, iminocycloalkylidenyl, carbonylcycloalkylideniminyl, alkylenesulfonyl, alkylenethio, alkylenearylthio, and carbonylalkylthio, wherein each of said releasable linkers is optionally substituted with one or more substituents $X^2$;

wherein each substituent $X^2$ is independently selected from the group consisting of alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from the group consisting of an amino acid, an amino acid derivative, and a peptide, and wherein $R^6$ and $R^7$ are each independently selected from the group consisting of an amino acid, an amino acid derivative, and a peptide.

8. The drug delivery conjugate of claim 7 wherein the heteroatom linker is nitrogen, and wherein the substituent $X^2$ and the heteroatom linker are taken together with the releasable linker to which they are bound to form an heterocycle.

9. The drug delivery conjugate of claim 8 wherein the heterocycle is selected from the group consisting of pyrrolidines, piperidines, oxazolidines, isoxazolidines, thiazolidines, isothiazolidines, pyrrolidinones, piperidinones, oxazolidinones, isoxazolidinones, thiazolidinones, isothiazolidinones, and succinimides.

10. The drug delivery conjugate of claim 1 wherein the heteroatom linker is nitrogen, and wherein the releasable linker and the heteroatom linker are taken together to form a divalent radical comprising alkyleneaziridin-1-yl, alkylenecarbonylaziridin-1-yl, carbonylalkylaziridin-1-yl, alkylenesulfoxylaziridin-1-yl, sulfoxylalkylaziridin-1-yl, sulfonylalkylaziridin-1-yl, or alkylenesulfonylaziridin-1-yl, wherein each of said releasable linkers is optionally substituted with one or more substituents $X^2$;

wherein each substituent $X^2$ is independently selected from the group consisting of alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from the group consisting of an amino acid, an amino acid derivative, and a peptide, and wherein $R^6$ and $R^7$ are each independently selected from the group consisting of an amino acid, an amino acid derivative, and a peptide.

11. The drug delivery conjugate of claim 10 wherein the heteroatom linker is nitrogen, and the releasable linker and the heteroatom linker are taken together to form a divalent radical comprising alkyleneaziridin-1-yl, carbonylalkylaziridin-1-yl, sulfoxylalkylaziridin-1-yl, or sulfonylalkylaziridin-1-yl,.

12. The drug delivery conjugate of claim 11 wherein the spacer linker is selected from the group consisting of carbonyl, thionocarbonyl, alkylenecarbonyl, cycloalkylenecarbonyl, carbonylalkylcarbonyl, and 1-(carbonylalkyl)succinimid-3-yl, wherein each of said spacer linkers is optionally substituted with one or more substituents $X^1$;

wherein each substituent $X^1$ is independently selected from the group consisting of alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from the group consisting of an amino acid, an amino acid derivative, and a peptide, and wherein $R^6$ and $R^7$ are each independently selected from the group consisting of an amino acid, an amino acid derivative, and a peptide;

and wherein the spacer linker is bonded to the releasable linker to form an aziridine amide.

13. The drug delivery conjugate of claim 1 wherein the drug is a mitomycin, a mitomycin derivative, or a mitomycin analog, and the releasable linker is selected from the group consisting of carbonylalkylthio, carbonyltetrahydro-2H-pyranyl, carbonyltetrahydrofuranyl, 1-(carbonyltetrahydro-2H-pyranyl)succinimid-3-yl, and 1 - (carbonyltetrahydrofuranyl)succinimid-3-yl, wherein each of said releasable linkers is optionally substituted with one or more substituents $X^2$, wherein each substituent $X^2$ is independently selected from the group consisting of alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and R⁵ are each independently selected from the group consisting of an amino acid, an amino acid derivative, and a peptide, and wherein R⁶ and R⁷ are each independently selected from the group consisting of an amino acid, an amino acid derivative, and a peptide;

and wherein the aziridine of the mitomycin is bonded to the releasable linker to form an acylaziridine.

14. The drug delivery conjugate of claim 1 wherein the drug includes a double-bonded nitrogen atom, wherein the releasable linker is selected from the group consisting of alkylenecarbonylamino and 1-(alkylenecarbonylamino)succinimid-3-yl, and wherein the releasable linker is bonded to the drug nitrogen to form an hydrazone.

15. The drug delivery conjugate of claim 1 wherein the drug includes a sulfur atom, the releasable linker is selected from the group consisting of alkylenethio and carbonylalkylthio, and wherein the releasable linker is bonded to the drug sulfur to form a disulfide.

16. The drug delivery conjugate of claim 4 wherein the vitamin receptor binding moiety is folate which includes a nitrogen, and the spacer linker is selected from the group consisting of alkylenecarbonyl, cycloalkylenecarbonyl, carbonylalkylcarbonyl, and 1-(carbonylalkyl)succinimid-3-yl, wherein the spacer linker is bonded to the folate nitrogen to form an imide or an alkylamide.

17. The drug delivery conjugate of claim 16 wherein each substituent X¹ is independently selected from the group consisting of alkyl, hydroxyalkyl, amino, aminoalkyl, alkylaminoalkyl, dialkylaminoalkyl, sulfhydrylalkyl, alkylthioalkyl, aryl, substituted aryl, arylalkyl, substituted arylalkyl, carboxy, carboxyalkyl, guanidinoalkyl, R⁴-carbonyl, R⁵-carbonylalkyl, R⁶-acylamino, and R⁷-acylaminoalkyl, wherein R⁴ and R⁵ are each independently selected from the group consisting of an amino acid, an amino acid derivative, and a peptide, and wherein R⁶ and R⁷ are each independently selected from the group consisting of an amino acid, an amino acid derivative, and a peptide.

18. The drug delivery conjugate of claim 4 wherein the heteroatom linker is nitrogen, and the spacer linker is selected from the group consisting of alkylenecarbonyl, cycloalkylenecarbonyl, carbonylalkylcarbonyl, and 1-(carbonylalkyl)succinimid-3-yl, wherein each of said spacer linkers is optionally substituted with one or more substituents X¹ and the spacer linker is bonded to the nitrogen to form an amide.

19. The drug delivery conjugate of claim 4 wherein the heteroatom linker is sulfur, and the spacer linker is selected from the group consisting of alkylene and cycloalkylene, wherein each of said spacer linkers is optionally substituted with carboxy, and the spacer linker is bonded to the sulfur to form a thiol.

20. The drug delivery conjugate of claim 4 wherein the heteroatom linker is sulfur, and the spacer linker is selected from the group consisting of 1-alkylenesuccinimid-3-yl and 1-(carbonylalkyl)succinimid-3-yl, and the spacer linker is bonded to the sulfur to form a succinimid-3-ylthiol.

21. The drug delivery conjugate of claim 7 wherein the heteroatom linker is oxygen, and the releasable linker is selected from the group consisting of methylene, 1-alkoxyalkylene, 1-alkoxycycloalkylene, 1-alkoxyalkylenecarbonyl, and 1-alkoxycycloalkylenecarbonyl, wherein each of said releasable linkers is optionally substituted with one or more substituents X², and the releasable linker is bonded to the oxygen to form an acetal or ketal.

22. The drug delivery conjugate of claim 7 wherein the heteroatom linker is oxygen, and the releasable linker is methylene, wherein said methylene is substituted with an optionally-substituted aryl, and the releasable linker is bonded to the oxygen to form an acetal or ketal.

23. The drug delivery conjugate of claim 7 wherein the drug includes a nitrogen atom, the heteroatom linker is nitrogen, and the releasable linker is selected from the group consisting of carbonylarylcarbonyl, carbonyl(carboxyaryl)carbonyl, carbonyl(biscarboxyaryl)carbonyl, and the releasable linker is bonded to the heteroatom linker nitrogen to form an amide, and also bonded to the drug nitrogen to form an amide.

24. The drug delivery conjugate of claim 7 wherein the drug includes an oxygen atom, the heteroatom linker is nitrogen, and the releasable linker is selected from the group consisting of carbonylarylcarbonyl, carbonyl(carboxyaryl)carbonyl, carbonyl(biscarboxyaryl)carbonyl, and the releasable linker is bonded to the heteroatom linker nitrogen to form an amide, and also bonded to the drug oxygen to form an ester.

25. The drug delivery conjugate of claim 7 wherein the heteroatom linker is nitrogen, and the releasable linker is selected from the group consisting of iminoalkylidenyl, carbonylalkylideniminyl, iminocycloalkylidenyl, and carbonylcycloalkylideniminyl, wherein each of said releasable linkers is optionally substituted with one or more substituents X², and the releasable linker is bonded to the nitrogen to form an hydrazone.

26. The drug delivery conjugate of claim 7 wherein the heteroatom linker is oxygen, and the releasable linker is selected from the group consisting of alkylene(dialkylsilyl), alkylene(alkylarylsilyl), alkylene(diarylsilyl), (dialkylsilyl)aryl, (alkylarylsilyl)aryl, and (diarylsilyl)aryl, wherein each of said releasable linkers is optionally substituted with one or more substituents X², and the releasable linker is bonded to the oxygen to form a silanol.

27. The drug delivery conjugate of claim 1 wherein the drug includes a nitrogen atom, and the releasable linker is haloalkylenecarbonyl, optionally substituted with one or more substituents X²;

wherein each substituent X² is independently selected from the group consisting of alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, R⁴-carbonyl, R⁵-carbonylalkyl, R⁶-acylamino, and R⁷-acylaminoalkyl, wherein R⁴ and R⁵ are each independently selected from the group consisting of an amino acid, an amino acid derivative, and a peptide, and wherein R⁶ and R⁷ are each independently selected from the group consisting of an amino acid, an amino acid derivative, and a peptide;

and the releasable linker is bonded to the drug nitrogen to form an amide.

28. The drug delivery conjugate of claim 1 wherein the drug includes an oxygen atom, and the releasable linker is alkyleneoxycarbonyl or haloalkylenecarbonyl, optionally substituted with one or more substituents X²;

wherein each substituent X² is independently selected from the group consisting of alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, R⁴-carbonyl, R⁵-carbonylalkyl, R⁶-acylamino, and R⁷-acylaminoalkyl, wherein R⁴ and R⁵ are each independently selected from the group consisting of an amino acid, an amino acid derivative, and a peptide, and wherein $R^6$ and $R^7$ are each independently selected from the group consisting of an amino acid, an amino acid derivative, and a peptide;

and the releasable linker is bonded to the drug oxygen to form a carbonate or an ester.

29. The drug delivery conjugate of claim 1 wherein the heteroatom linker is oxygen, the spacer linker is 1-alkylenesuccinimid-3-yl, optionally substituted with one or more substituents $X^1$, and the releasable linker is selected from the group consisting of methylene, 1-alkoxyalkylene, 1-alkoxycycloalkylene, 1-alkoxyalkylenecarbonyl, 1-alkoxycycloalkylenecarbonyl, wherein each of said releasable linkers is optionally substituted with one or more substituents $X^2$;

wherein each substituent $X^2$ is independently selected from the group consisting of alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from the group consisting of an amino acid, an amino acid derivative, and a peptide, and wherein $R^6$ and $R^7$ are each independently selected from the group consisting of an amino acid, an amino acid derivative, and a peptide;

and wherein the spacer linker and the releasable linker are each bonded to the heteroatom linker to form a succinimid-1-ylalkyl acetal or ketal.

30. The drug delivery conjugate of claim 1 wherein the bivalent linker comprises an heteroatom linker, a spacer linker, and a releasable linker taken together to form 3-thiosuccinimid-1-ylalkyloxymethyloxy, where the methyl is optionally substituted with alkyl or substituted aryl.

31. The drug delivery conjugate of claim 1 wherein the bivalent linker comprises an heteroatom linker, a spacer linker, and a releasable linker taken together to form 3-thiosuccinimid-1-ylalkylcarbonyl, where the carbonyl forms an acylaziridine with the drug, or analog or derivative thereof.

32. The drug delivery conjugate of claim 1 wherein the bivalent linker comprises an heteroatom linker, a spacer linker, and a releasable linker taken together to form 1-alkoxycycloalkylenoxy.

33. The drug delivery conjugate of claim 1 wherein the bivalent linker comprises a spacer linker, an heteroatom linker, and a releasable linker taken together to form alkyleneaminocarbonyl(dicarboxylarylene)carboxylate.

34. The drug delivery conjugate of claim 1 wherein the bivalent linker comprises a releasable linker, a spacer linker, and a releasable linker taken together to form dithioalkylcarbonylhydrazide, where the hydrazide forms an hydrazone with the drug, or analog or derivative thereof.

35. The drug delivery conjugate of claim 1 wherein the bivalent linker comprises an heteroatom linker, a spacer linker, and a releasable linker taken together to form 3-thiosuccinimid-1-ylalkylcarbonylhydrazide, where the hydrazide forms an hydrazone with the drug, or analog or derivative thereof.

36. The drug delivery conjugate of claim 1 wherein the bivalent linker comprises an heteroatom linker, a spacer linker, an heteroatom linker, a spacer linker, and a releasable linker taken together to form 3-thioalkylsulfonylalkyl(disubstituted silyl)oxy, where the disubstituted silyl is substituted with alkyl or optionally substituted aryl.

37. The drug delivery conjugate of claim 1 wherein the bivalent linker comprises a plurality of spacer linkers selected from the group consisting of the naturally occurring amino acids and stereoisomers thereof.

38. The drug delivery conjugate of claim 1 wherein the bivalent linker comprises a releasable linker, a spacer linker, and a releasable linker taken together to form 3-dithioalkyloxycarbonyl, where the carbonyl forms a carbonate with the drug, or analog or derivative thereof.

39. The drug delivery conjugate of claim 1 wherein the bivalent linker comprises a releasable linker, a spacer linker, and a releasable linker taken together to form 3-dithioarylalkyloxycarbonyl, where the carbonyl forms a carbonate with the drug, or analog or derivative thereof, and the aryl is optionally substituted.

40. The drug delivery conjugate of claim 1 wherein the bivalent linker comprises an heteroatom linker, a spacer linker, a releasable linker, a spacer linker, and a releasable linker taken together to form 3-thiosuccinimid-1-ylalkyloxyalkyloxyalkylidene, where the alkylidene forms an hydrazone with the drug, or analog or derivative thereof, each alkyl is independently selected, and the oxyalkyloxy is optionally substituted with alkyl or optionally substituted aryl.

41. The drug delivery conjugate of claim 1 wherein the bivalent linker comprises a releasable linker, a spacer linker, and a releasable linker taken together to form 3-dithioalkyloxycarbonylhydrazide.

42. The drug delivery conjugate of claim 1 wherein the bivalent linker comprises a releasable linker, a spacer linker, and a releasable linker taken together to form 3-dithioalkylamino, where the amino forms a vinylogous amide with the drug, or analog or derivative thereof.

43. The drug delivery conjugate of claim 42 wherein the alkyl is ethyl.

44. The drug delivery conjugate of claim 1 wherein the bivalent linker comprises a releasable linker, a spacer linker, and a releasable linker taken together to form 3-dithioalkylaminocarbonyl, where the carbonyl forms a carbamate with the drug, or analog or derivative thereof.

45. The drug delivery conjugate of claim 44 wherein the alkyl is ethyl.

46. The drug delivery conjugate of claim 1 wherein the bivalent linker comprises a releasable linker, a spacer linker, and a releasable linker taken together to form 3-dithioarylalkyloxycarbonyl, where the carbonyl forms a carbamate or a carbamoylaziridine with the drug, or analog or derivative thereof.

47. A pharmaceutical composition comprising a drug delivery conjugate of claim 1, and a pharmaceutically acceptable carrier, diluent, or excipient therefor.

48. A method of eliminating a population of pathogenic cells in a host animal harboring the population of pathogenic cells wherein the members of the pathogenic cell population have an accessible binding site for a vitamin, or an analog or a derivative thereof, and wherein the binding site is uniquely expressed, overexpressed, or preferentially expressed by the pathogenic cells, said method comprising the step of administering to said host a drug delivery conjugate of claim 1, or a pharmaceutical composition thereof.

49. A vitamin receptor binding drug delivery conjugate intermediate comprising:
  (a) a vitamin receptor binding moiety;
  (b) a bivalent linker, having a first end and a second end; and
  (c) a coupling group;

wherein the coupling group is a nucleophile, an electrophile, or a precursor thereof, capable of forming a covalent bond with a drug, or an analog or derivative thereof;

the vitamin receptor binding moiety is covalently attached to the bivalent linker at the first end of the bivalent linker, and the coupling group is covalently attached to the bivalent linker at the second end of the bivalent linker; and the bivalent linker comprises one or more components selected from the group consisting of spacer linkers, releasable linkers, and heteroatom linkers, and combinations thereof; providing that the bivalent linker includes at least one releasable linker that is not a disulfide.

50. The intermediate of claim 49 wherein the vitamin receptor binding moiety is a vitamin, or a vitamin receptor binding analog or derivative thereof.

51. A vitamin receptor binding drug delivery conjugate having the formula:

V-L-D wherein L is selected from the group consisting of $(l_s)_a$, $(l_H)_b$, and $(l_r)_c$, and combinations thereof; where $(l_r)$ is a releasable linker, $(l_s)$ is a spacer linker, and $(l_H)$ is an heteroatom linker;

V is a vitamin receptor binding moiety, and D is a drug, or an analog or a derivative thereof; and a, b, and c are each independently 0, 1, 2, 3, or 4;

providing that L includes at least one $(l_r)$ that is not a disulfide.

52. A vitamin receptor binding drug delivery conjugate intermediate comprising:

(a) a bivalent linker, having a first end and a second end;

(b) a drug, or an analog or a derivative thereof; and (c) a coupling group;

wherein the bivalent linker comprises one or more components selected from the group consisting of spacer linkers, releasable linkers, and heteroatom linkers, and combinations thereof; providing that the bivalent linker includes at least one releasable linker that is not a disulfide;

the coupling group is a nucleophile, an electrophile, or a precursor thereof, capable of forming a covalent bond with a vitamin receptor binding moiety;

the coupling group is covalently attached to the bivalent linker at the first end of the bivalent linker, and the drug, or analog or derivative thereof is covalently attached to the bivalent linker at the second end of the bivalent linker.

53. The intermediate of claim 52 wherein the vitamin receptor binding moiety is a vitamin, or a vitamin receptor binding analog or derivative thereof; the coupling group is a Michael acceptor; and the bivalent linker includes a releasable linker having a formula selected from the group consisting of —C(O)NHN=, —NHC(O)NHN=, and —CH$_2$C(O)NHN=.

54. The intermediate of claim 52 wherein the bivalent linker comprises a first releasable linker, and a first spacer linker; and the first releasable linker, the first spacer linker, and the coupling group are taken together to form a compound having the formula:

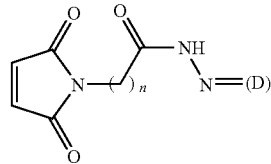

where D is the drug, or an analog or a derivative thereof, and n is an integer selected from the group consisting of 1, 2, 3, and 4.

55. The intermediate of claim 54 wherein the vitamin receptor binding moiety includes an alkylthiol nucleophile.

56. A process for preparing a compound having the formula:

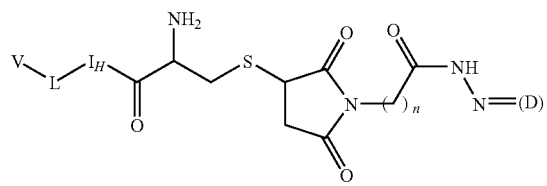

where V is a vitamin receptor binding moiety; L is selected from the group consisting of $(l_r)_c$, $(l_s)_a$, and $(l_H)_b$, and combinations thereof, where $(l_r)$ is a releasable linker, $(l_s)$ is a spacer linker, $(l_H)$ is an heteroatom linker, and a, b, and c are integers selected from the group consisting of 0, 1, 2, 3, and 4; and D is a drug, or an analog or a derivative thereof; comprising:

(a) reacting a compound having the formula:

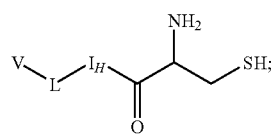

with a compound having the formula:

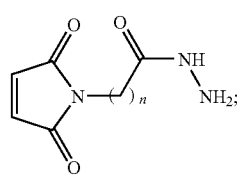

and (b) forming a hydrazone derivative of the drug, or the analog or derivative thereof.

57. A process for preparing a compound having the formula:

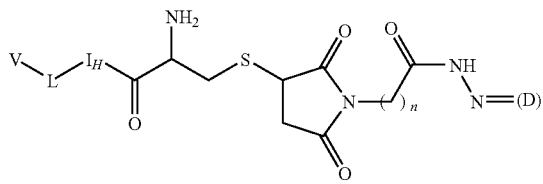

where V is a vitamin receptor binding moiety; L is selected from the group consisting of $(l_r)_c$, $(l_s)_a$, and $(l_H)_b$, and combinations thereof, where $(l_r)$ is a releasable linker, $(l_s)$ is a spacer linker, $(l_H)$ is an heteroatom linker, and a, b, and c are integers selected from the group consisting of 0, 1, 2, 3, and 4; and D is a drug, or an analog or a derivative thereof; comprising:

reacting a compound having the formula:

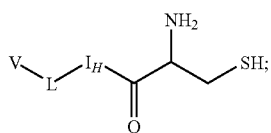

with a compound having the formula:

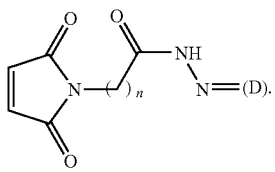

58. The process of claim 57 wherein the drug or the analog or derivative thereof is selected from the group consisting of daunomycins, daunomycinones, daunorubicins, aclamycins, taxols, chromomycins, and aurilic acids.

59. The drug delivery conjugate of claim 1 wherein the drug is a vinca alkaloid, or an analog or derivative thereof.

60. The drug delivery conjugate of claim 59 wherein the vinca alkaloid is selected from the group consisting of vinblastine, vincristine, and analogs and derivatives thereof.

61. The drug delivery conjugate of claim 1 wherein the bivalent linker comprises 3-thiosuccinimid-1-ylalkyloxy.

62. The drug delivery conjugate of claim 1 wherein the bivalent linker comprises 3-cysteinylsuccinimid-1-ylalkyloxy, where the cysteinyl is optically active or optically inactive.

63. The drug delivery conjugate of claim 1 wherein the bivalent linker comprises 3-thiosuccinimid-1-ylalkylcarbonyl bonded to a heteroatom linker at the carbonyl.

64. The drug delivery conjugate of claim 1 wherein the bivalent linker comprises 3-cysteinylsuccinimid-1-ylalkylcarbonyl bonded to a heteroatom linker at the carbonyl, where the cysteinyl is optically active or optically inactive.

65. The drug delivery conjugate of claim 1 wherein the bivalent linker comprises dithioethyloxycarbonyl bonded to a heteroatom linker at the carbonyl.

66. The drug delivery conjugate of claim 65 wherein the heteroatom linker is —NHNH—.

67. The drug delivery conjugate of claim 1 wherein the bivalent linker comprises cysteinylthioethyloxycarbonyl, or a stereoisomer thereof, bonded to a heteroatom linker at the carbonyl.

68. The drug delivery conjugate of claim 67 wherein the heteroatom linker is —NHNH—.

69. The drug delivery conjugate of claim 37 wherein the naturally occurring amino acids are selected from the group consisting of aspartic acid, arginine, beta-aminoalanine, and cysteine, and stereoisomers thereof.

70. The drug delivery conjugate of claim 1 wherein the bivalent linker comprises 4-dithiobenzyloxycarbonyl bonded to a heteroatom linker at the carbonyl.

71. The drug delivery conjugate of claim 1 wherein the bivalent linker comprises 4-oxy(2-alkoxy)benzyloxycarbonyl bonded to a heteroatom linker at the carbonyl.

72. The drug delivery conjugate of claim 1 wherein the a vitamin receptor binding moiety is folate.

73. The drug delivery conjugate of claim 1 wherein the drug is an epothilone.

* * * * *

UNITED STATES PATENT AND TRADEMARK OFFICE
CERTIFICATE OF CORRECTION

PATENT NO. : 7,601,332 B2 Page 1 of 1
APPLICATION NO. : 10/765336
DATED : October 13, 2009
INVENTOR(S) : Vlahov et al.

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by 478 days Delete the phrase "by 478 days" and insert -- by 1054 days --

Signed and Sealed this

Thirteenth Day of April, 2010

David J. Kappos
*Director of the United States Patent and Trademark Office*